(12) United States Patent
Nishitani et al.

(10) Patent No.: US 9,242,999 B2
(45) Date of Patent: Jan. 26, 2016

(54) CEPHEM COMPOUND HAVING PYRIDINIUM GROUP

(75) Inventors: Yasuhiro Nishitani, Toyonaka (JP); Toshiaki Aoki, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/129,631

(22) PCT Filed: Jun. 26, 2012

(86) PCT No.: PCT/JP2012/066270
§ 371 (c)(1),
(2), (4) Date: Dec. 27, 2013

(87) PCT Pub. No.: WO2013/002215
PCT Pub. Date: Jan. 3, 2013

(65) Prior Publication Data
US 2014/0114060 A1     Apr. 24, 2014

(30) Foreign Application Priority Data

Jun. 27, 2011   (JP) ................. 2011-142001

(51) Int. Cl.
C07D 501/36 (2006.01)
C07D 501/60 (2006.01)
C07D 505/00 (2006.01)

(52) U.S. Cl.
CPC ............ *C07D 501/60* (2013.01); *C07D 501/36* (2013.01); *C07D 505/00* (2013.01)

(58) Field of Classification Search
CPC ........................................................ C07D 501/60
See application file for complete search history.

(56) References Cited

U.S. PATENT DOCUMENTS

| | | |
|---|---|---|
| 3,966,719 A | 6/1976 | Barth |
| 4,032,521 A | 6/1977 | Christensen et al. |
| 4,039,532 A | 8/1977 | Barth |
| 4,110,327 A | 8/1978 | Saikawa et al. |
| 4,179,511 A | 12/1979 | Barth |
| 4,327,097 A | 4/1982 | Saikawa et al. |
| 4,410,522 A | 10/1983 | Saikawa et al. |
| 4,684,641 A | 8/1987 | Greengrass et al. |
| 5,134,138 A | 7/1992 | Onoue et al. |
| 5,143,910 A | 9/1992 | Onoue et al. |
| 5,262,411 A | 11/1993 | Shirasaka et al. |
| 5,275,816 A | 1/1994 | Branch et al. |
| 2011/0190254 A1 | 8/2011 | Nishitani et al. |
| 2013/0079319 A1 | 3/2013 | Yamawaki et al. |
| 2013/0096299 A1 | 4/2013 | Kusano et al. |
| 2013/0102583 A1 | 4/2013 | Hisakawa et al. |

FOREIGN PATENT DOCUMENTS

| | | |
|---|---|---|
| CN | 85 1 0579 A | 12/1986 |
| DE | 2519400 | 3/1976 |
| EP | 0114752 | 8/1984 |
| EP | 0168177 | 1/1986 |
| EP | 0207447 | 1/1987 |
| EP | 0211656 | 2/1987 |
| EP | 0305111 | 3/1989 |
| EP | 1489084 | 12/2004 |
| JP | 49-94697 | 9/1974 |
| JP | 50-121293 | 9/1975 |
| JP | 57-118588 | 7/1982 |
| JP | 61-018788 | 1/1986 |
| JP | 01-258684 | 10/1989 |
| JP | 02-015090 | 1/1990 |
| JP | 02-028185 | 1/1990 |
| JP | 02-028187 | 1/1990 |
| JP | 02-117678 | 5/1990 |
| JP | 03-128383 | 5/1991 |
| JP | 03-141287 | 6/1991 |
| JP | 03-173893 | 7/1991 |
| JP | 03-232892 | 10/1991 |
| JP | 04-221388 | 8/1992 |
| JP | 04-364189 | 12/1992 |
| JP | 05-213971 | 8/1993 |
| JP | 06-510523 | 11/1994 |

(Continued)

OTHER PUBLICATIONS

Wermuth, Camille. Molecular Variations Based on Isoteric Replacements. The Practice of Medicinal Chemistry. Academic Press, 1996. pp. 203-237.*

(Continued)

*Primary Examiner* — Golam M Shameem
*Assistant Examiner* — Laura Daniel
(74) *Attorney, Agent, or Firm* — Hamre, Schumann, Mueller & Larson, P.C.

(57) ABSTRACT

The present invention provides a novel compound which has a broad antibacterial spectrum and particularly exhibits a high antibacterial activity on β-lactamase-producing gram-negative bacteria. Specifically provided are: a compound represented by formula (I)

(I)

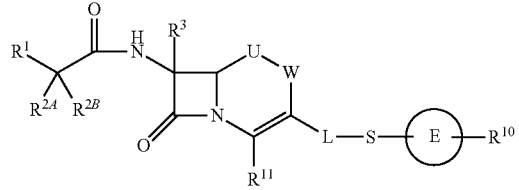

wherein the meaning of each symbol is as defined in the description, an amino-group-protected form of a type of the compound which has the amino group on a ring in a position-7 side chain, or a pharmaceutically acceptable salt of the compound or the amino-group-protected form; and a pharmaceutical composition containing the compound, the amino-group-protected form or the pharmaceutically acceptable salt.

21 Claims, No Drawings

(56) References Cited

FOREIGN PATENT DOCUMENTS

| WO | WO 92/21683 | 12/1992 |
|---|---|---|
| WO | WO 03/078440 | 9/2003 |
| WO | WO 2006/104141 | 10/2006 |
| WO | WO 2007/096740 | 8/2007 |
| WO | WO 2007/119511 | 10/2007 |
| WO | WO 2010/050468 | 5/2010 |
| WO | WO 2011/125966 | 10/2011 |
| WO | WO 2011/125967 | 10/2011 |
| WO | WO 2011/136268 | 11/2011 |

OTHER PUBLICATIONS

Yamano et al.: "Ferric iron transport system of *Pseudomonas aeruginosa* PA01 that functions as the uptake pathway of a novel catechol-substituted cephalosporin, S-9095"; Applied Microbiology and Biotechnology 1994, 40(6), pp. 892-897.

Takeda et al.: "In Vitro Antibacterial Activity of a New Cephalosporin, FR295389, against IMP-type Metallo-β-lactamase-producers"; The Journal of Antibiotics, 2008, 61(1), pp. 36-39.

Hashizume et al: "Comparison of Transport Pathways of Catechol-Substituted Cephalosporins, BO-1236 and BO-1341, Through the Outer Membrane of *Escherichia coli*"; The Journal of Antibiotics, 1990, 43, No. 12, pp. 1617-1620.

Weissberger et al.: "L-658,310, a New Injectable Cephalosporin I. In Vitro Antibacterial Propertis"; The Journal of Antibiotics, 1989, 21, No. 5, pp. 795-806.

Branch et al.: "Studies on Semi-Synthetic 7α-Formamidocephalosporins III. Synthesis and Antibacterial Activity of Some 7β-[D-2-(Aryl)-2-[(4-Ethyl-2,3-Dioxopiperazin-1-Yl)-Carbonylamino]Acetamido]-7α-Formamido-Ceph-3-Em-4-Carboxylate Derivatives"; The Journal of Antibiotics, 1987, 40, pp. 646-651.

Fletcher et al.: "A comparison of $\alpha_1$-Proteinase Inhibitor Methoxysuccinyl-Ala-Ala-Pro-Val-Chloromethylketone and Specific β-Lactam Inhibitors in an Acute Model of Human Polymorphonuclear Leukocyte Elastase-induced Lung Hemorrhage in the Hamster[1,2]"; American Review of Respiratory Disease 1990, 141(3), pp. 672-677.

Yoshida et al.: "Studies on Monocyclic β-Lactam Antibiotics III. Synthesis and Antibacterial Activity of N-(Aromatic Heterocyclic Substituted) Azetidin-2-Ones"; The Journal of Antibiotics 1986, 39, pp. 76-89.

\* cited by examiner

CEPHEM COMPOUND HAVING PYRIDINIUM GROUP

TECHNICAL FIELD

The compounds of the subject invention are related to Cephem compounds, which have a wide antimicrobial spectrum, in particular exhibit potent antimicrobial activity against beta-lactamase producing Gram negative bacteria, and pharmaceutical compositions comprising the same.

BACKGROUND ART

To date, a variety of beta-lactam drugs have been developed and beta-lactam drugs have become clinically extremely important antimicrobial drugs. However, there are increasing number of bacterial types which have obtained resistance against beta-lactam drugs by producing beta-lactamase, which degrade beta-lactam drugs.

According to the Ambler molecular classification, beta-lactamases are largely classified into four classes. Specifically, these are Class A (TEM type, SHV type, CTX-M type, KPC type and the like), Class B (IMP type, VIM type, L-1 type and the like), Class C (AmpC type) and Class D (OXA type and the like). Amongst these, Classes A, C and D types are largely classified into serine-beta-lactamase, on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to a number of beta-lactam drugs including Cephems and Carbapenems by producing Class A (ESBL) and D types serine-beta-lactamases which have an extended substrate spectrum, and Class B type metallo-beta-lactamase which have an extended substrate spectrum. Particularly, metallo-beta-lactamase is known to be one of the causes of obtaining multidrug-resistance in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular more effective against a variety of beta-lactamase producing Gram negative bacteria.

One of the known antimicrobials having high anti-Gram negative bactericidal activity is Cephem compounds having a catechol group intramolecularly (e.g., Non-patent Documents 2-4). The action thereof is that the catechol group forms a chelate with $Fe^{3+}$, thereby the compound is efficiently incorporated into the bacterial body through the $Fe^{3+}$ transportation system on the cellular membrane (tonB-dependent iron transport system). Therefore, research has been conducted on compounds having catechol or similar structure thereto, on the 3-side chain or 7-side chain moiety on the Cephem backbone.

Patent Documents 2-8 and Non-patent Document 5 describe compounds having a partial structure of the 7-side chain and a quaternary salt structure on the Cephem backbone. However, these documents merely describe a pyridinium structure, and merely disclose compounds having a formamide group at the 7-position in most cases. Furthermore, for example, most compounds disclosed in Patent Document 2 have a penicillin structure.

Non-patent document 1 and Patent Documents 8-12 and 15 describe catechol type derivatives having a catechol group on the 3-side chain moiety on the Cephem backbone. Patent Documents 10, 11, 13, and 14 describe pseudo-catechol type derivatives having a hydroxypyridone group on the 3-side chain moiety on the Cephem backbone. Patent Documents 16 and 17 disclose Cephem compounds having a quaternary ammonium group.

Moreover, in the above documents, which describe Cephem compounds having a catechol group in their structure, there is no description of Class B type metallo-beta-lactamase, and specific antimicrobial activity against a wide variety of Gram negative bacteria including Class B type.

Patent Document 22 discloses a compound having S-pyridinium on the 3-side chain of the Cephem backbone. However, this document does not disclose a compound having a bioisoster of carboxyl ion, such as tetrazoryl, on the 4-side chain of the Cephem backbone.

Additionally, Patent Document 7 describes that penicilin compounds having a tetrazolyl group at position 3 of the penicilin skeleton has superior stability against beta-lactamase. However, a Cephem compound having a tetrazolyl group at position 4 of the penicilin skeleton is not disclosed in this document.

Patent Documents 18, 19, 20 and Non-Patent Document 6 describe Cephem compounds having a tetrazolyl group at position 4 of the penicilin skeleton. However, a compound having a quaternary ammonium group at the 3-side chain is not disclosed in these documents.

On the other hand, Cephem compounds having catechol type substituents is disclosed by the present applicant (Patent Document 21). Furthermore, the present applicant has already disclosed an application relating to Cephem antimicrobial agent having potent antimicrobial activity against beta-lactamase producing Gram negative bacteria (Patent Documents 23-25). However, these documents do not disclose a compound having S-pyridinium at position 3 of the cephem skeleton.

PRIOR ART DOCUMENT

Patent Document

[Patent Document 1] International Publication No. 2007/119511 pamphlet
[Patent Document 2] German Patent Publication No. 2519400
[Patent Document 3] Japanese Laid-Open Publication No. 57-118588
[Patent Document 4] European Patent Application Publication No. 114752
[Patent Document 5] European Patent Application Publication No. 168177
[Patent Document 6] European Patent Application Publication No. 211656
[Patent Document 7] European Patent Application Publication No. 305111
[Patent Document 8] Japanese Laid-Open Publication No. 4-364189
[Patent Document 9] Japanese Laid-Open Publication No. 3-173893
[Patent Document 10] Japanese Laid-Open Publication No. 2-15090
[Patent Document 11] Japanese Laid-Open Publication No. 2-28187
[Patent Document 12] Japanese Laid-Open Publication No. 2-117678
[Patent Document 13] Japanese PCT National Phase Laid-Open Publication No. 6-510523

[Patent Document 14] Japanese Laid-Open Publication No. 5-213971
[Patent Document 15] Japanese Laid-Open Publication No. 2-28185
[Patent Document 16] International Publication No. 2007/096740 pamphlet
[Patent Document 17] International Publication No. 2003/078440 pamphlet
[Patent Document 18] U.S. Pat. No. 4,039,532
[Patent Document 19] U.S. Pat. No. 3,966,719
[Patent Document 20] European Patent Application Publication No. 207447
[Patent Document 21] International Publication No. 2010/050468 pamphlet
[Patent Document 22] Japanese Laid-Open Publication No. 3-128383
[Patent Document 23] International Publication No. 2011/125966 pamphlet
[Patent Document 24] International Publication No. 2011/125967 pamphlet
[Patent Document 25] International Publication No. 2011/136268 pamphlet Non-Patent Document

[Non-patent document 1] Applied Microbiology and Biotechnology (1994), 40(6), 892-7
[Non-patent document 2] The Journal of Antibiotics, vol. 61, pp. 36-39 (2008)
[Non-patent document 3] The Journal of Antibiotics, vol. 43, pp. 1617-1620 (1990)
[Non-patent document 4] The Journal of Antibiotics, vol. 42, pp. 795-806 (1989)
[Non-patent document 5] The Journal of Antibiotics, vol. 40, pp. 646-651 (1987)
[Non-patent document 6] American Review of Respiratory Disease (1990), 141(3), 672-7
[Non-patent document 7] The Journal of Antibiotics, Vol. 39, pp. 76-89 (1986)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria. The subject invention provides Cephem compounds which exhibit potent antimicrobial activity against beta-lactamase producing Gram negative bacteria. More particularly, the subject invention provides Cephem compounds which exhibit potent antimicrobial activity against multi-drug-resistant bacteria, in particular, Class B type metallo-beta-lactamase producing Gram negative bacteria. Still more particularly, the subject invention provides Cephem compounds which exhibit effective antimicrobial activity against extended-spectrum beta-lactamase (ESBL) producing bacteria. Furthermore, the subject invention provides Cephem compounds having antimicrobial activity against strains resistant to Cephem compounds having carboxyl group at position 4.

Means for Solving the Problem

The subject invention provides Cephem compounds which have solved the above-mentioned problems by having the following characteristics in structure:

(Item 1)
A compound of the formula:

[Formula 1]

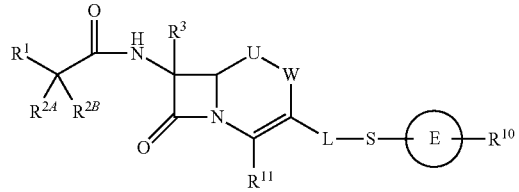

(I)

or an amino-protected compound when the amino group is present on the ring in the 7-side chain, or a pharmaceutically acceptable salt thereof,
wherein
W is —$CH_2$—, —S— or —O—;
  a) U is —$CH_2$—, —S—, —S(=O)— or —O— when W is —$CH_2$—; or
  b) U is —$CH_2$— when W is —S— or —O—;
L is a single bond, an optionally substituted lower alkylene group, an optionally substituted lower alkenylene group or an optionally substituted alkynylene group;
$R^1$ is an optionally substituted carbocyclic group or an optionally substituted heterocyclic group;
  with regard to $R^{2A}$ and $R^{2B}$,
  a) $R^{2A}$ is a hydrogen atom, an optionally substituted amino group, —$SO_3H$, an optionally substituted amino sulfonyl group, carboxyl group, an optionally substituted (lower alkyl) oxycarbonyl group, an optionally substituted carbamoyl group, hydroxyl group, or a substituted carbonyloxy group; and $R^{2B}$ is a hydrogen atom, or
  b) $R^{2A}$ and $R^{2B}$ are taken together to form an optionally substituted methylidene group or an optionally substituted hydroxyimino group;
$R^3$ is a hydrogen atom, —$OCH_3$ or —NH—CH(=O);
$R^{11}$ is a bioisoster of carboxyl ion;
ring E is an optionally substituted pyridinium ring or an optionally substituted fused ring containing pyridinium ring;
  1) when two hydroxyl groups bind to two adjacent carbon atoms respectively on an aromatic ring of the ring E, $R^{10}$ is —$R^{12}$ or a group represented by the formula:

[Formula 2]

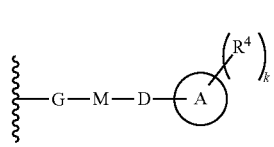

wherein
ring A is a benzene ring, or a 6-membered aromatic heterocyclic group having 1-3 nitrogen atoms;
k is an integer from 2 to 5;
each $R^4$ is independently a hydrogen atom, halogen, hydroxyl group, —CN, —C(=O)—$R^5$, —C(=O)—OH, —C(=O)—$OR^5$, or —$OR^5$;
$R^5$ is a lower alkyl group or halo(lower)alkyl group;
G is a single bond, an optionally substituted lower alkylene group, an optionally substituted alkenylene group or an optionally substituted alkynylene group;
M is a single bond or a 5- or 6-membered heterocyclic group containing at least 1-3 nitrogen atoms;

D is a single bond, —CO—, —O—CO—, —CO—O—, —NR$^6$—, —NR$^6$—CO—, —CO—NR$^6$—, —NR$^6$—CO—NR$^6$—, —O—, —S—, —SO—, —SO$_2$—NR$^6$—, —NR$^6$—SO$_2$—, —CH$_2$—NR$^6$—CO— or —SO$_2$—;

each R$^6$ is independently a hydrogen atom or an optionally substituted lower alkyl group;

2) In cases other than the case that two hydroxyl groups bind to two adjacent carbon atoms respectively on an aromatic ring of the ring E, R$^{10}$ is a group represented by the formula:

[Formula 3]

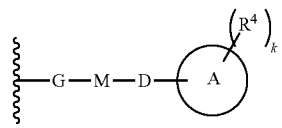

wherein each symbol is as defined above with the proviso that at least two R$^4$ are hydroxyl groups which bind respectively to adjacent carbon atoms on ring A;

R$^{12}$ is a hydrogen atom, halogen, hydroxyl group, —SO$_3$H, an optionally substituted amino group, an optionally substituted carboxyl group, an optionally substituted carbamoyl group, an optionally substituted acyl group, an optionally substituted amino sulfonyl group, an optionally substituted lower alkyl group, an optionally substituted lower alkenyl group, an optionally substituted lower alkynyl group, an optionally substituted non-aromatic carbocyclic group or an optionally substituted non-aromatic heterocyclic group.

(Item 2)

The compound or an amino-protected compound when the amino group is present on the ring in the 7-side chain, or a pharmaceutically acceptable salt thereof according to Item 1, wherein R$^{10}$ is a group represented by the formula:

[Formula 4]

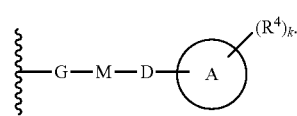

(Item 3)

The compound or an amino-protected compound when the amino group is present on the ring in the 7-side chain, or a pharmaceutically acceptable salt thereof according to Item 2, wherein G is a single bond, —CH$_2$—, —CH$_2$—CH$_2$—, —CH$_2$—CH$_2$—CH$_2$—, —CH=CH—, —CH=CH—CH$_2$—, —CH$_2$—CH=CH—, —CH$_2$—CH(CH$_3$)—, —CH$_2$—CH($^i$Pr)— or —CH$_2$—CH(Ph)- wherein $^i$Pr is isopropyl group and Ph is phenyl group.

(Item 4)

The compound or an amino-protected compound when the amino group is present on the ring in the 7-side chain, or a pharmaceutically acceptable salt thereof according to Item 2 or 3, wherein M is a single bond or a group represented by the formula:

[Formula 5]

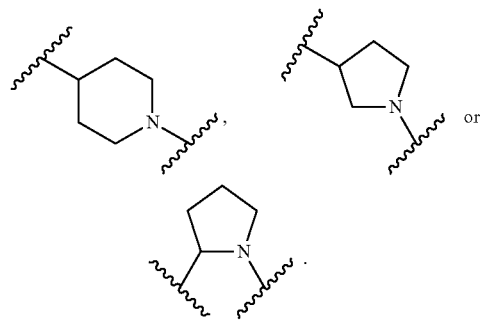

wherein the bond of the left side is attached to G and the bond of the right side is attached to D.

(Item 5)

The compound or an amino-protected compound when the amino group is present on the ring in the 7-side chain, or a pharmaceutically acceptable salt thereof according to any one of Items 2 to 4, wherein D is a single bond, —CO—, —O—CO—, —CO—O—, —NR$^6$—, —NR$^6$—CO—NR$^6$—, —NR$^6$—CO— or —CO—NR$^6$— wherein R$^6$ is as defined in Item 1.

(Item 6)

The compound or an amino-protected compound when the amino group is present on the ring in the 7-side chain, or a pharmaceutically acceptable salt thereof according to any one of Items 2 to 5, wherein the formula:

[Formula 6]

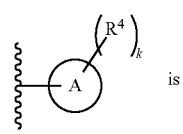 is

[Formula 7]

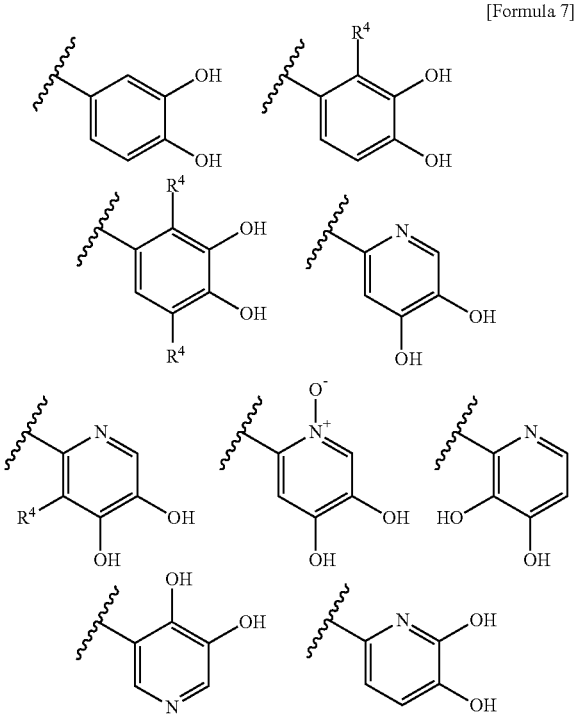

-continued

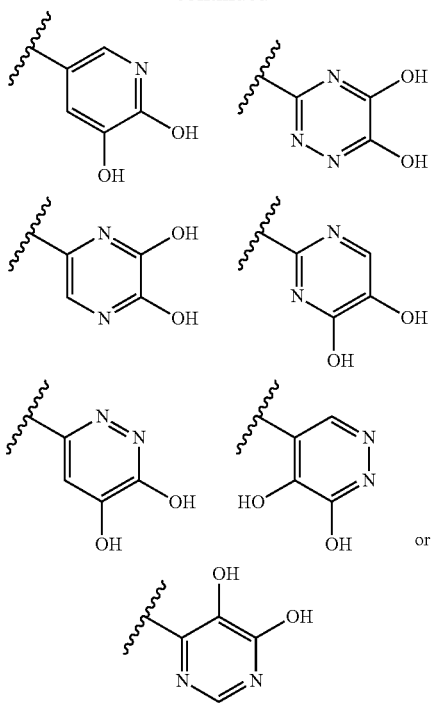

wherein each $R^4$ is independently hydrogen, halogen, hydroxyl group, —CN, —C(=O)—$R^5$, —C(=O)—OH, —C(=O)—$OR^5$ or —$OR^5$; and $R^5$ is as defined in Item 1.

(Item 7)

The compound or an amino-protected compound when the amino group is present on the ring in the 7-side chain, or a pharmaceutically acceptable salt thereof according to Item 6, wherein the formula:

[Formula 8]

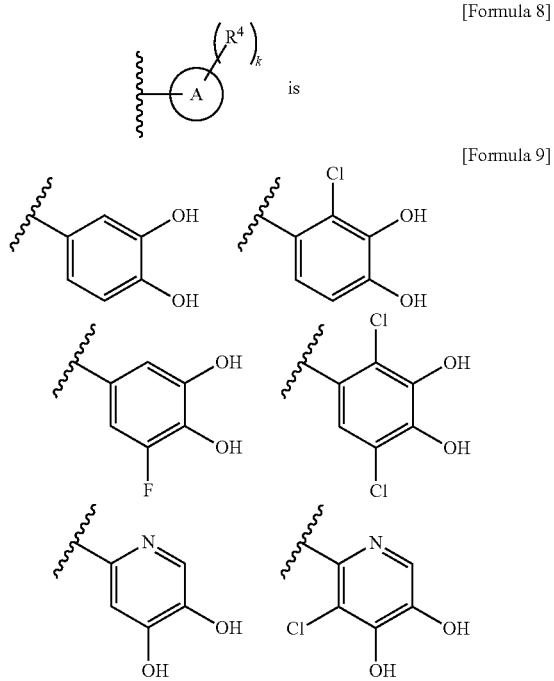

[Formula 9]

-continued

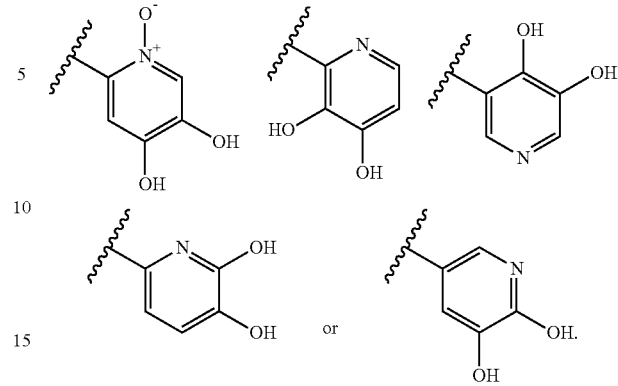

(Item 8)

The compound or an amino-protected compound when the amino group is present on the ring in the 7-side chain, or a pharmaceutically acceptable salt thereof according to Item 6, wherein the formula:

[Formula 10]

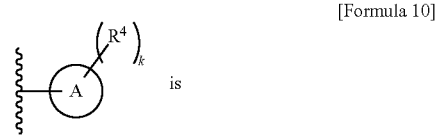

is

[Formula 11]

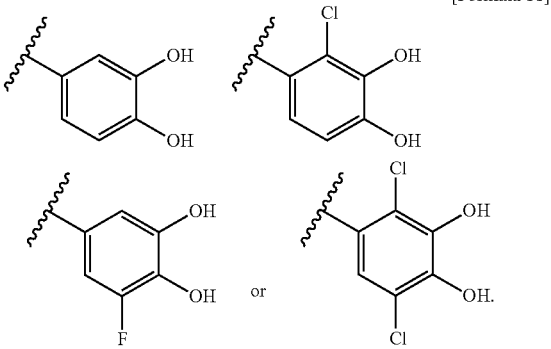

(Item 9)

The compound or an amino-protected compound when the amino group is present on the ring in the 7-side chain, or a pharmaceutically acceptable salt thereof according to any one of Items 1 to 8, wherein the formula:

[Formula 12]

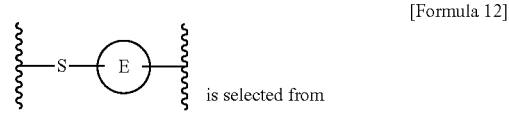

is selected from

[Formula 13]

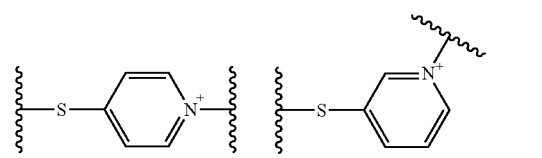

-continued

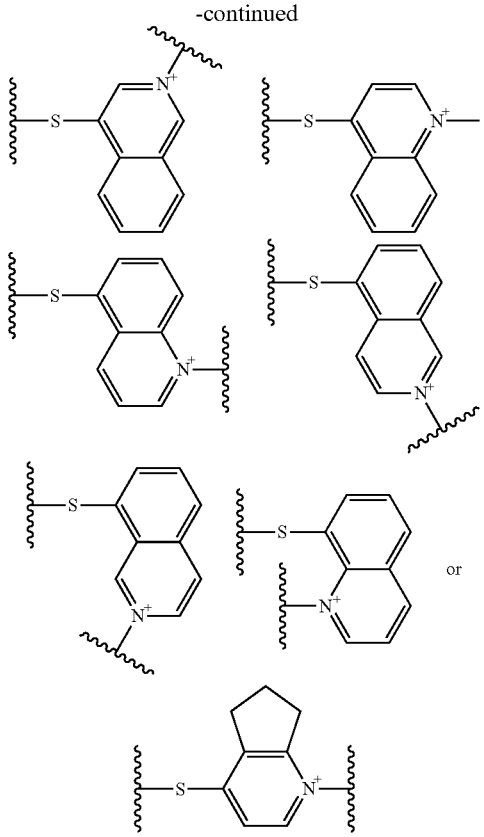

wherein the ring is optionally substituted.
(Item 10)
The compound or an amino-protected compound when the amino group is present on the ring in the 7-side chain, or a pharmaceutically acceptable salt thereof according to Item 9, wherein the formula:

[Formula 14]

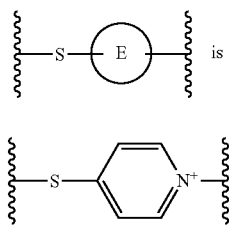

is selected from

[Formula 15]

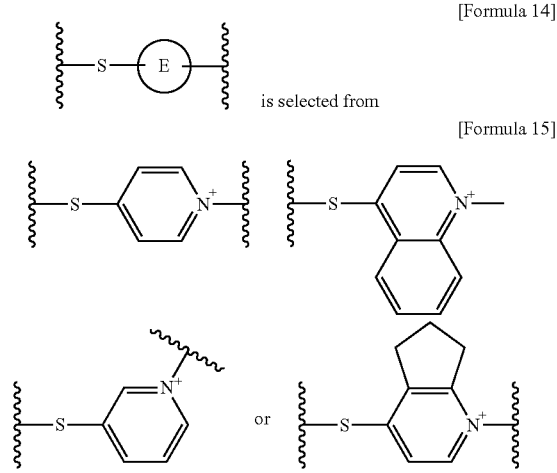

wherein the ring is optionally substituted.
(Item 11)
The compound or an amino-protected compound when the amino group is present on the ring in the 7-side chain, or a pharmaceutically acceptable salt thereof according to Item 9, wherein the formula:

[Formula 16]

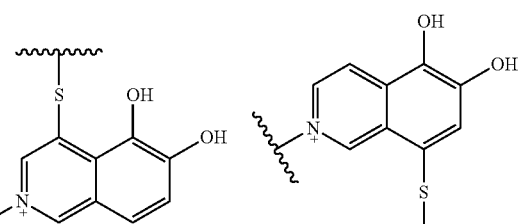

is

[Formula 17]

wherein the ring is optionally substituted.
(Item 12)
The compound or an amino-protected compound when the amino group is present on the ring in the 7-side chain, or a pharmaceutically acceptable salt thereof according to any one of Items 1 to 8, wherein the formula:

[Formula 18]

is selected from

[Formula 19]

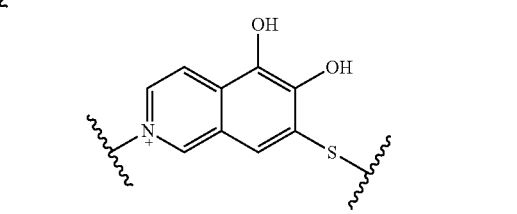

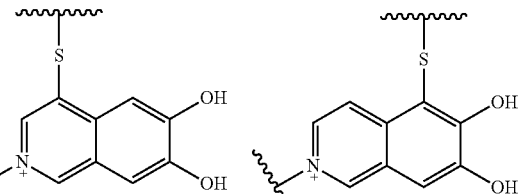

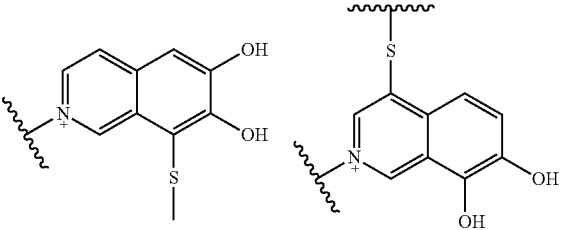

-continued
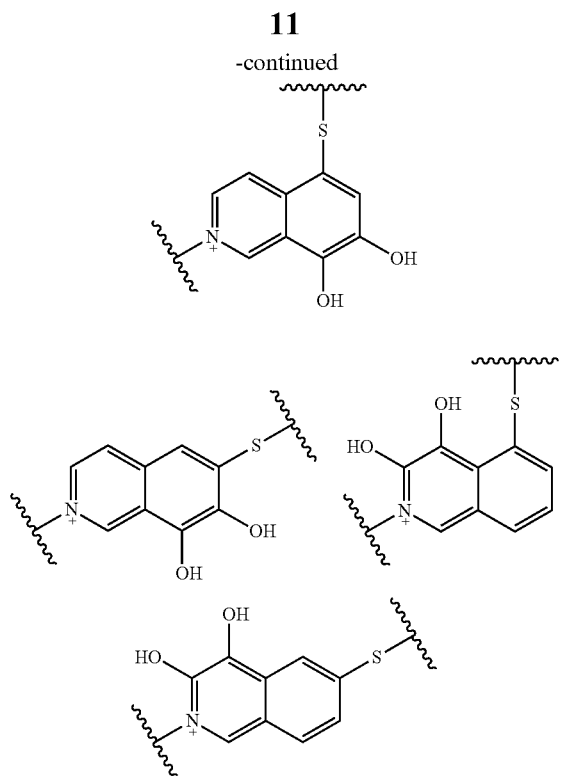
[Formula 20]
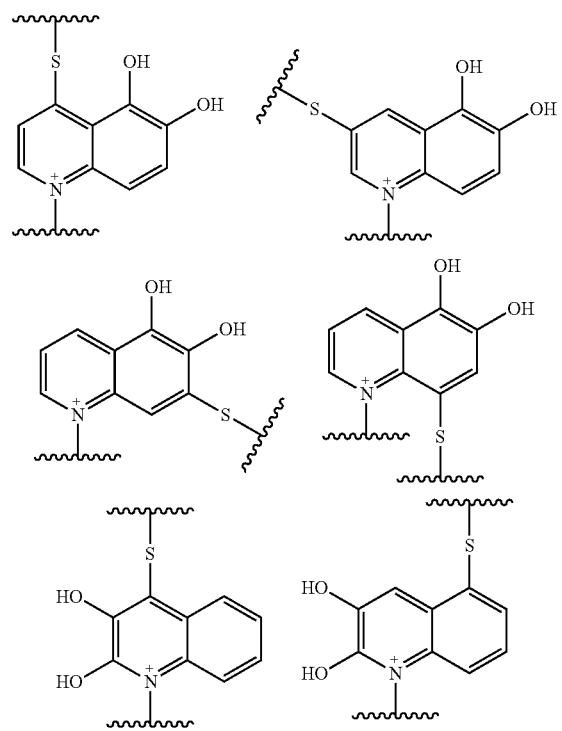
-continued
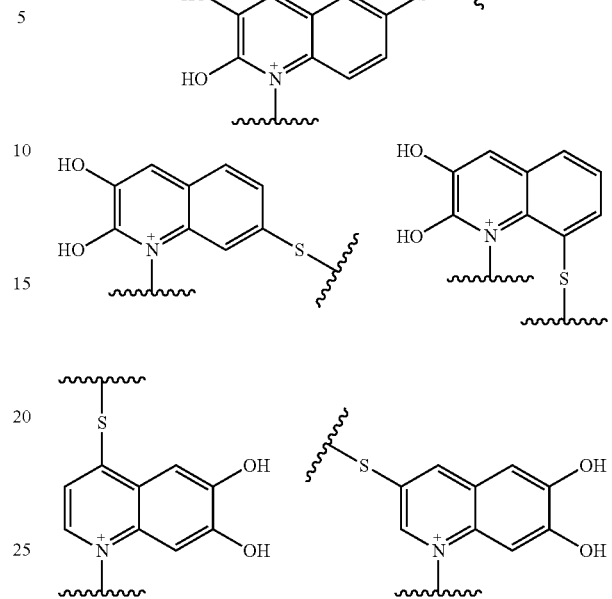
[Formula 21]
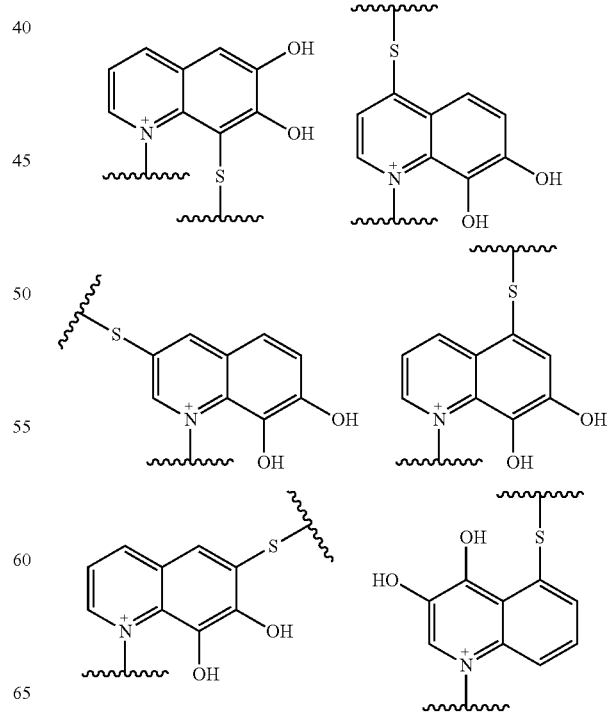

-continued
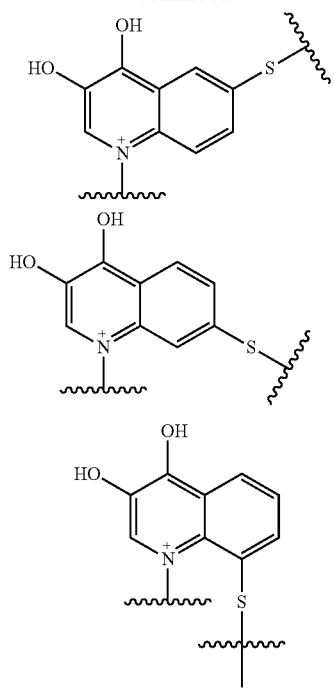
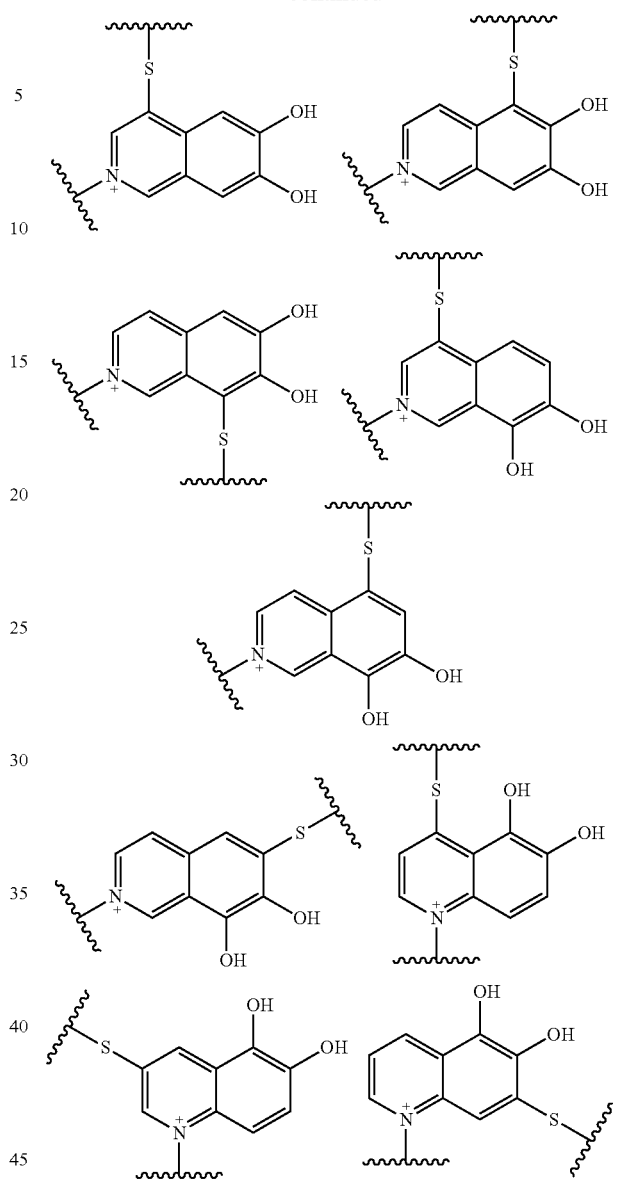
wherein the ring is optionally substituted.
(Item 13)
The compound or an amino-protected compound when the amino group is present on the ring in the 7-side chain, or a pharmaceutically acceptable salt thereof according to Item 12, wherein the formula:
[Formula 22]
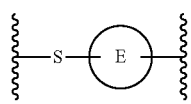
is selected from
[Formula 23]
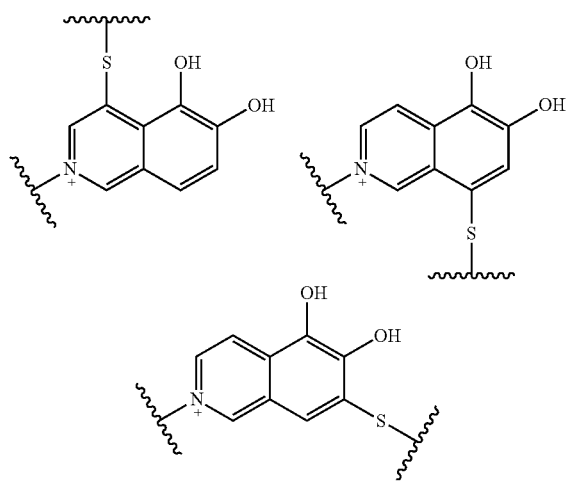
[Formula 24]
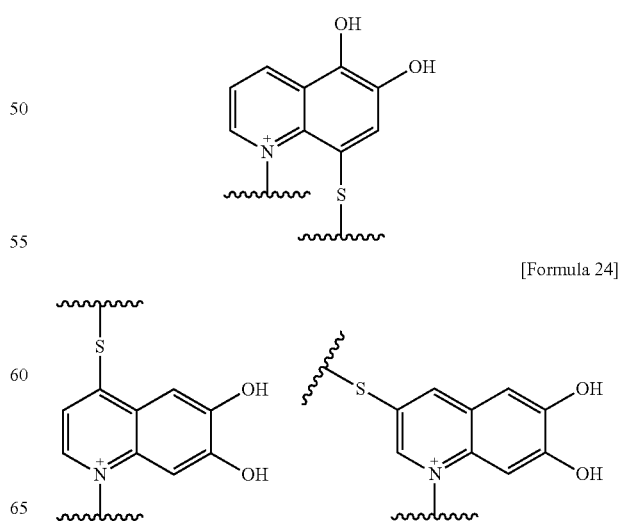

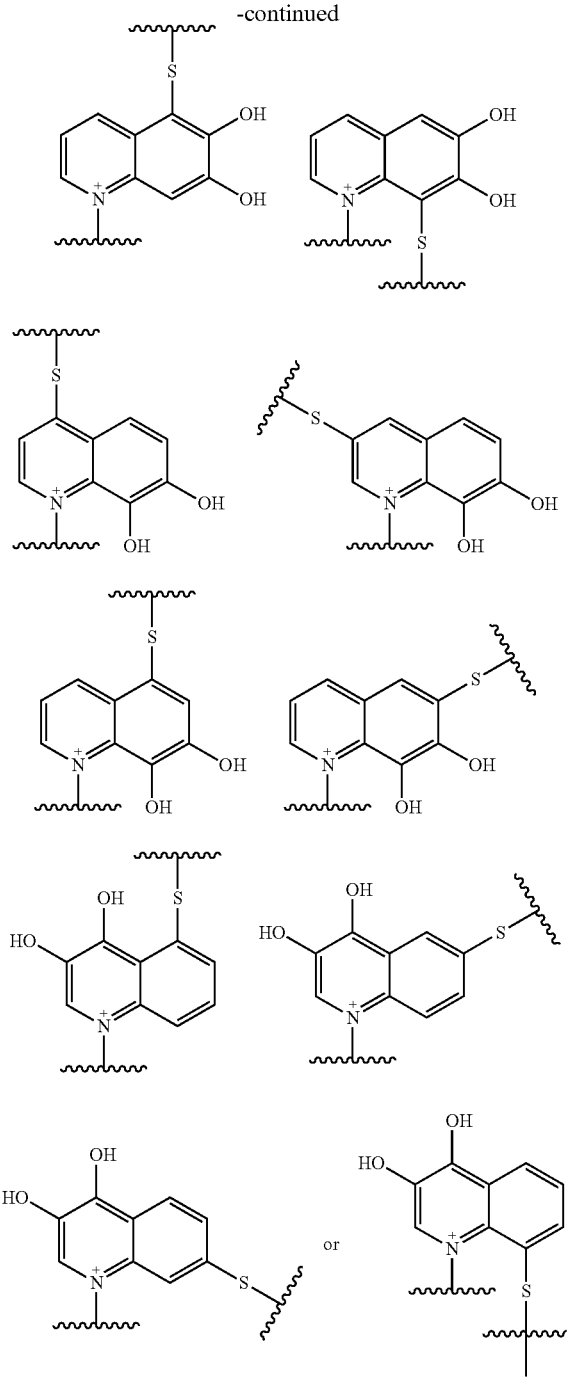

wherein the ring is optionally substituted.

(Item 14)

The compound or an amino-protected compound when the amino group is present on the ring in the 7-side chain, or a pharmaceutically acceptable salt thereof according to any one of Items 1 to 13, wherein the bioisoster of carboxyl ion is selected from —$SO_3^-$, —$SO_2$—$N^-$—$R^{13}$, —$PO^-$—($OR^{13}$), —$PO_2^-$—($OR^{13}$), —$N^-$—CO—$R^{13}$, —CO—$N^-$—$OR^{13}$, —CO—NH—$N^-$—$SO_2$—$R^{13}$, —CO—$N^-$—$SO_2$—$R^{13}$, —CO—CH=C($O^-$)—$R^{13}$, —$N^-$—$SO_2$—$R^{13}$, —CO—$N^-$—$SO_2$—$R^{13}$, —$N^-$—$SO_2$—$R^{13}$, —CO—$N^-$—CO—$R^{13}$, —CO—$N^-$—$SO_2$—$R^{13}$, —$N^-$—CO—$R^{13}$,

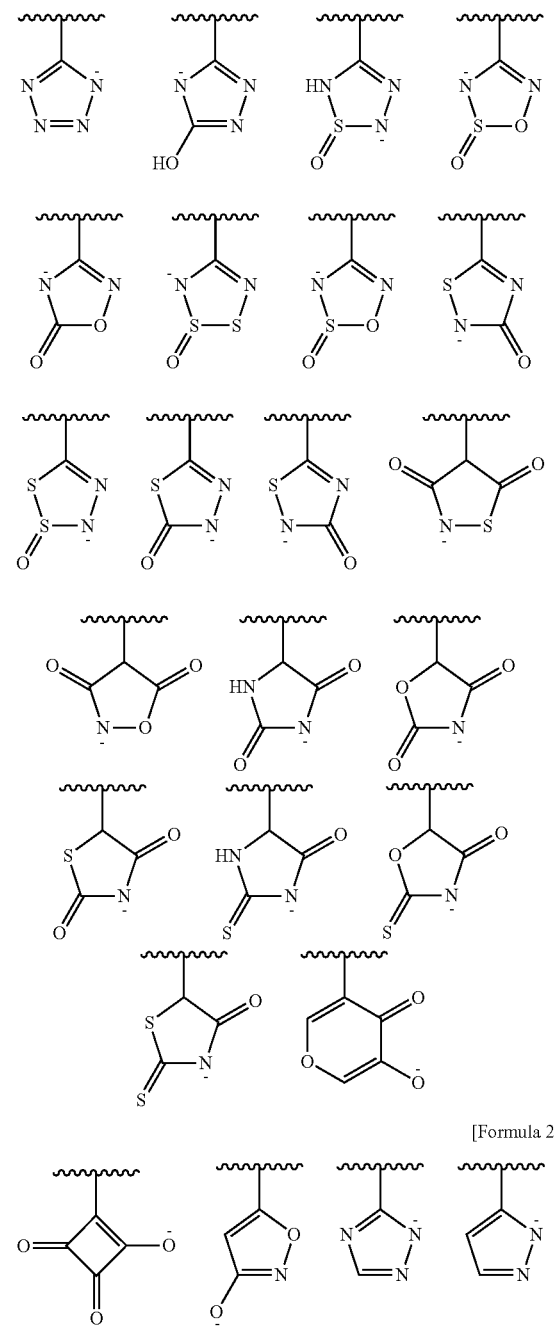

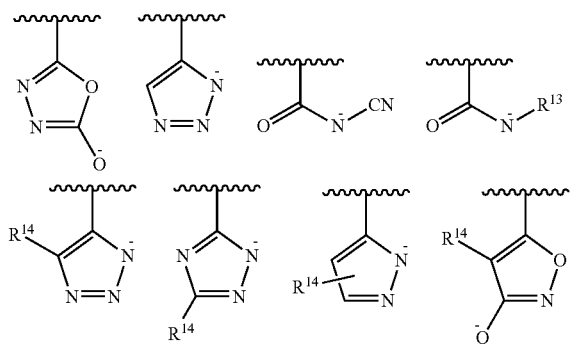

-continued

[Formula 27]

wherein R¹³ is selected from the group consisting of hydrogen, hydroxyl group, halogen, an optionally substituted lower alkyl group, an optionally substituted lower alkenyl group, an optionally substituted lower alkynyl group, an optionally substituted lower alkoxy group, an optionally substituted amino group, (lower alkenyl)oxy group, an optionally substituted aryloxy group, cyano, nitro, imino, mercapto, (lower alkyl) thio group, (lower alkyl)sulphonyl group, an optionally substituted carbocyclic group, an optionally substituted heterocyclic group and —CO₂R¹⁷ wherein R¹⁷ is hydrogen, lower alkyl group or lower alkenyl group; and R¹⁴ is an electron-withdrawing group.

(Item 15)

The compound or an amino-protected compound when the amino group is present on the ring in the 7-side chain, or a pharmaceutically acceptable salt thereof according to Item 14, wherein the bioisoster of carboxyl ion is

[Formula 28]

(Item 16)

The compound or an amino-protected compound when the amino group is present on the ring in the 7-side chain, or a pharmaceutically acceptable salt thereof according to any one of Items 1 to 15, wherein U is —S—.

(Item 17)

The compound or an amino-protected compound when the amino group is present on the ring in the 7-side chain, or a pharmaceutically acceptable salt thereof according to any one of Items 1 to 16, wherein R³ is a hydrogen atom or —OCH₃.

(Item 18)

The compound or an amino-protected compound when the amino group is present on the ring in the 7-side chain, or a pharmaceutically acceptable salt thereof according to any one of Items 1 to 17, wherein R¹ is an optionally substituted phenyl.

(Item 19)

The compound or an amino-protected compound when the amino group is present on the ring in the 7-side chain, or a pharmaceutically acceptable salt thereof according to any one of Items 1 to 17, wherein R¹ is represented by the formula:

[Formula 29]

wherein X is N, C(—H) or C(—Cl).

(Item 20)

The compound or an amino-protected compound when the amino group is present on the ring in the 7-side chain, or a pharmaceutically acceptable salt thereof according to Item 19, wherein X is N.

(Item 21)

The compound or an amino-protected compound when the amino group is present on the ring in the 7-side chain, or a pharmaceutically acceptable salt thereof according to Item 19, wherein X is C(—H) or C(—Cl).

(Item 22)

The compound or an amino-protected compound when the amino group is present on the ring in the 7-side chain, or a pharmaceutically acceptable salt thereof according to any one of Items 1 to 21, wherein with regard to $R^{2A}$ and $R^{2B}$, a) $R^{2A}$ is a hydrogen atom, an optionally substituted amino group, —SO₃H, an optionally substituted amino sulphonyl group, carboxyl group, an optionally substituted carbamoyl group, hydroxyl group, or substituted carbonyloxy group, and $R^{2B}$ is a hydrogen atom.

(Item 23)

The compound or an amino-protected compound when the amino group is present on the ring in the 7-side chain, or a pharmaceutically acceptable salt thereof according to Item 22, wherein $R^{2A}$ is a substituted amino group shown below:

[Formula 30]

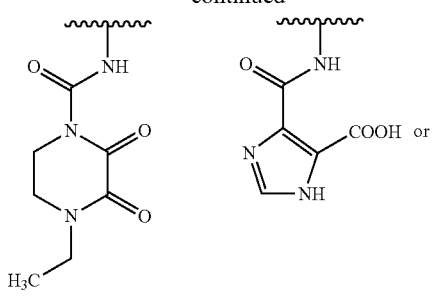

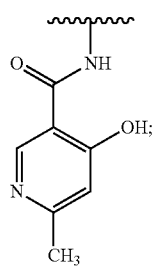

a substituted amino sulfonyl group shown below:

[Formula 31]

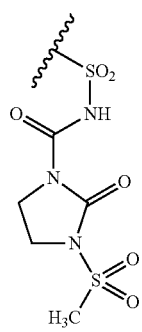 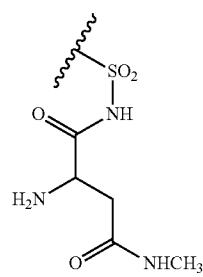

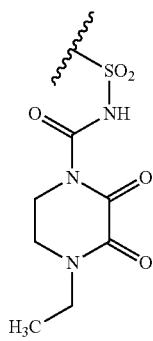 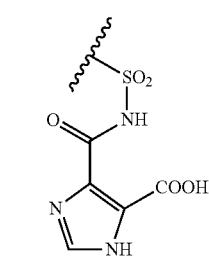

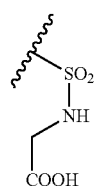 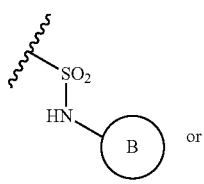 or

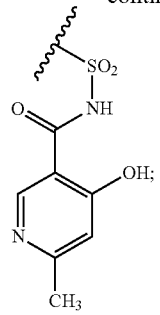

wherein ring B represents an optionally substituted heterocyclic group;

a substituted carbamoyl group shown below:

[Formula 32]

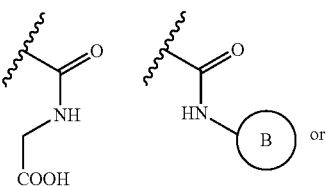 or

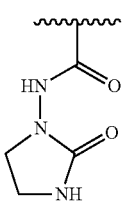

wherein ring B represents an optionally substituted heterocyclic group; or a substituted carbonyloxy group shown below:

[Formula 33]

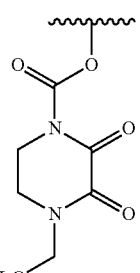 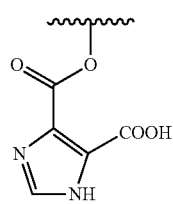

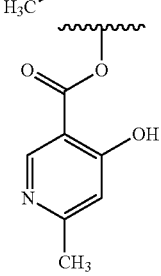 or 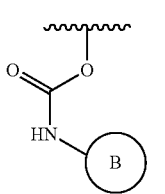

wherein ring B represents an optionally substituted heterocyclic group.

(Item 24)

The compound or an amino-protected compound when the amino group is present on the ring in the 7-side chain, or a pharmaceutically acceptable salt thereof according to any one of Items 1 to 21, wherein with regard to $R^{2A}$ and $R^{2B}$, b) $R^{2A}$ and $R^{2B}$ are taken together to form a substituted methylidene group shown below:

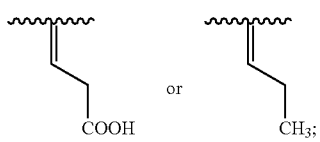
[Formula 34]

or
a substituted hydroxyimino group shown below:

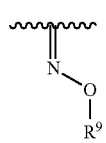
[Formula 35]

wherein $R^9$ is an optionally substituted lower alkyl group.
(Item 25)

The compound or an amino-protected compound when the amino group is present on the ring in the 7-side chain, or a pharmaceutically acceptable salt thereof according to any one of Items 1 to 21, wherein with regard to $R^{2A}$ and $R^{2B}$, b) $R^{2A}$ and $R^{2B}$ are taken together to form a substituted hydroxyimino group shown below:

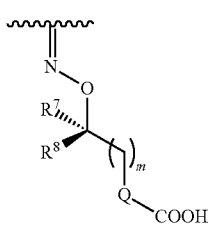
[Formula 36]

wherein $R^7$ and $R^8$ are each independently a hydrogen atom, halogen, hydroxyl group, carboxyl group, an optionally substituted lower alkyl group, an optionally substituted carbocyclic group, or an optionally substituted heterocyclic group, or $R^7$ and $R^8$ may be taken together with a neighboring atom to form an optionally substituted carbocyclic group or an optionally substituted heterocyclic group;
Q is a single bond, an optionally substituted carbocyclic group or an optionally substituted heterocyclic group; and
m is an integer from 0 to 3.
(Item 26)

The compound or an amino-protected compound when the amino group is present on the ring in the 7-side chain, or a pharmaceutically acceptable salt thereof according to any one of Items 1 to 25, wherein L is a single bond, —$CH_2$—, —CH═CH— or —CH═CH—$CH_2$—.
(Item 27)

The compound or an amino-protected compound when the amino group is present on the ring in the 7-side chain, or a pharmaceutically acceptable salt thereof according to any one of Items 1 to 26, wherein L is a single bond or —$CH_2$—.
(Item 28)

The compound or an amino-protected compound when the amino group is present on the ring in the 7-side chain, or a pharmaceutically acceptable salt thereof according to any one of Items 1 to 27, wherein W is —$CH_2$—.
(Item 29)

A pharmaceutical composition, which comprises a compound or an amino-protected compound when the amino group is present on the ring in the 7-side chain, or a pharmaceutically acceptable salt thereof according to any one of Items 1 to 28.
(Item 30)

A antibacterial agent, which comprises a compound or an amino-protected compound when the amino group is present on the ring in the 7-side chain, or a pharmaceutically acceptable salt thereof according to any one of Items 1 to 28.

Effects of the Invention

The compounds of the subject invention are useful as a pharmaceutical product in that the compounds have at least one of the following features:
1) The compounds exhibit potent antimicrobial spectrum against a variety of bacteria including Gram negative bacteria and/or Gram positive bacteria;
2) the compounds exhibit potent antimicrobial activity against beta-lactamase producing Gram negative bacteria;
3) the compounds exhibit potent antimicrobial activity against multidrug-resistant bacteria, in particular, Class B type metallo-beta-lactamase producing Gram negative bacteria;
4) the compounds exhibit potent antimicrobial activity against extended-spectrum beta-lactamase (ESBL) producing bacteria;
5) the compounds do not exhibit cross resistance with known Cephem drugs and/or Carbapenem drugs; and
6) the compounds do not exhibit side effects such as fever after administration into the body.

EMBODIMENTS FOR CARRYING OUT THE INVENTION

Hereinafter, the subject invention is described with showing embodiments. It should be understood that, throughout the present specification, the expression of a singular form (for example, in the English language, "a", "an", "the", and the like; and in other languages, corresponding articles, adjectives, and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the subject invention pertains. If there is a contradiction, the present specification (including definitions) precedes. Each specific definition of terms specifically used herein is described below.

Each term in the present specification is used alone or in combination with another word, and defined as below.

"Halogen" includes fluorine, chlorine, bromine and iodine. Preferably, halogen is fluorine or chlorine, and more preferably is chlorine.

"Lower alkyl group" includes linear or branched alkyl group having 1-8 carbons, preferably 1-6 carbons, and more preferably 1-4 carbons, and includes, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like.

"Lower alkylene group" includes linear alkylene group having 1-8 carbons, preferably 1-6 carbons, more preferably 1-4 carbons, and most preferably one or two carbons, and includes, for example, methylene, ethylene, n-propylene, n-butylene, n-pentylene, n-hexylene, and the like.

"Lower alkenylene group" includes linear alkenylene group having 2-8 carbons, preferably 2-6 carbons, more preferably 2-4 carbons, and at least one double bond at any position, and includes, for example, vinylene, allylene, propenylene, butenylene, prenylene, butadienylene, pentenylene, pentadienylene, hexenylene, hexadienylene, and the like.

"Lower alkynylene group" includes linear alkynylene group having 2-8 carbons, preferably 2-6 carbons, more preferably 2-4 carbons, and at least one triple bond at any position, and includes, for example, ethynylene, propynylene, buthynylene, pentynylene, hexynylene, and the like.

"Halo(lower)alkyl group" refers to a group in which at least one position of said "lower alkyl group" is substituted with the above "halogen", and includes, for example, monofluoromethyl, difluoromethyl, trifluoromethyl, monochloromethyl, dichloromethyl, trichloromethyl, monobromomethyl, monofluoroethyl, monochloroethyl, chlorodifluoromethyl, and the like. Preferably, halo(lower)alkyl group is trifluoromethyl, or trichloromethyl.

Substituents of an "optionally substituted amino group" or "optionally substituted carbamoyl group" include optionally substituted lower alkyl (e.g., methyl, ethyl, isopropyl, benzyl, carbamoylalkyl (e.g., carbamoylmethyl), mono- or di-(lower)alkylcarbamoyl(lower)alkyl (e.g., dimethylcarbamoylethyl), hydroxy(lower)alkyl, heterocycle(lower)alkyl (e.g., morpholinoethyl, tetrahydropyranylethyl), alkoxycarbonyl(lower)alkyl (e.g., ethoxycarbonylmethyl, ethoxycarbonylethyl), mono- or di-(lower)alkylamino(lower)alkyl (e.g., dimethylaminoethyl)), (lower)alkoxy(lower)alkyl (e.g., methoxyethyl, ethoxymethyl, ethoxyethyl, isopropoxyethyl, and the like), acyl (e.g., formyl, optionally substituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl, alkoxycarbonylacetyl (e.g., ethoxycarbonylmethylcarbonyl), (lower)alkoxy(lower)alkylcarbonyl (e.g., methoxyethylcarbonyl), (lower)alkylcarbamoyl(lower)alkylcarbonyl (e.g., methylcarbamoylethylcarbonyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally having a lower alkyl or halogen as a substituent (e.g., benzenesulfonyl, toluenesulfonyl, 4-fluorobenzenesulfonyl), cycloalkyl (e.g., cyclopropyl), aryl optionally having a lower alkyl as a substituent (e.g., phenyl, tolyl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino), and the like, and the amino group and carbamoyl group may be mono-substituted or di-substituted with these groups.

"Lower alkenyl group" refers to a linear or branched alkenyl having 2 to 8 carbons and having one or more double bonds on said "lower alkyl group". Examples thereof include vinyl, 1-propenyl, 2-propenyl, 1-butenyl, 2-butenyl, 3-butenyl, 1,3-butadienyl, 3-methyl-2-butenyl, and the like. Preferred is alkenyl having 2 to 6 carbons, more preferably 2 to 4 carbons.

With regard to an amino group of an "optionally substituted amino group" or "optionally substituted carbamoyl group", two substituents of the amino group may be taken together with the adjacent nitrogen atom to form a nitrogen-containing heterocycle which optionally includes a sulfur atom and/or an oxygen atom in the ring (preferably, the heterocycle is a 5- to 7-membered ring, and is preferably saturated). The heterocycle is optionally substituted with oxo or hydroxy. When a sulfur atom forms the heterocycle, said sulfur atom may be substituted with oxo. Examples thereof include 5- or 6-membered rings such as piperazinyl, piperidino, morpholino, pyrrolidino, 2-oxopiperidino, 2-oxopyrrolidino, 4-hydroxymorpholino, and the like.

Substituents of an "optionally substituted lower alkyl group" include at least one group selected from the following Substituent Group Alpha. When substitutions are carried out with a plurality of substituent group, these substituent groups may be the same or different.

Substituents of an "optionally substituted lower alkylene group", an "optionally substituted lower alkenylene group" and an "optionally substituted lower alkynylene group" include at least one group selected from the following Substituent Group Alpha. When substitutions are carried out with a plurality of substituent group, these substituents may be the same or different.

Substituents of an "optionally substituted aminosulfonyl group" include a substituted lower alkyl and at least one group selected from the following Substituent Group Alpha.

Substituents of an "optionally substituted lower alkyloxycarbonyl group" include optionally substituted lower alkyl and at least one group selected from Substituent Group Alpha.

Substituents of a "substituted carbonyloxy group" meaning "—O—C(=O)-substituent" include an optionally substituted lower alkyl, an optionally substituted lower alkenyl, an optionally substituted lower alkynyl, an optionally substituted carbocyclic group, an optionally substituted heterocyclic group, an amino having a heterocyclic group as a substituent, and at least one group selected from the following Substituent Group Alpha.

Substituents of a "optionally substituted carboxyl group" include an optionally substituted lower alkyl, an optionally substituted lower alkenyl, an optionally substituted lower alkynyl, an optionally substituted carbocyclic group, an optionally substituted heterocyclic group.

"Optionally substituted acyl group" means a carbonyl group optionally substituted with an optionally substituted lower alkyl, an optionally substituted lower alkenyl, an optionally substituted lower alkynyl, an optionally substituted carbocyclic group, an optionally substituted heterocyclic group.

Substituents of an "optionally substituted, saturated or unsaturated, monocyclic or fused cyclic quaternary ammonium group" include an optionally substituted lower alkyl, at least one group selected from the following Substituent Group Alpha, or two or more substituents that are taken together to form a carbocyclic group or heterocyclic group.

Here, "Substituent Group Alpha" is a group consisting of halogen, hydroxy, lower alkoxy, hydroxy(lower)alkoxy, (lower)alkoxy(lower)alkoxy, carboxy, amino, acylamino, lower(alkyl)amino, imino, hydroxyimino, lower(alkoxy) imino, lower(alkyl)thio, carbamoyl, lower(alkyl)carbamoyl, hydroxy(lower)alkylcarbamoyl, sulfamoyl, lower(alkyl)sulfamoyl, lower(alkyl)sulfinyl, cyano, nitro, a carbocyclic group, and a heterocyclic group.

The lower alkyl moiety in "lower alkoxy group", "hydroxy (lower)alkoxy group", "(lower)alkoxy(lower)alkoxy group", "lower(alkyl)amino group", "lower(alkoxy)imino group", "lower(alkyl)thio group", "lower(alkyl)carbamoyl group", "hydroxy(lower)alkylcarbamoyl group", and "lower (alkyl) sulfamoyl group", "lower(alkyl)sulfinyl group", "lower (alkyl)oxycarbonyl group", "lower(alkyl)sulfonyl group", is defined the same as the above "lower alkyl group".

The lower alkenyl moiety in "lower(alkenyl)oxy group", is defined the same as the above "lower alkenyl group".

The aryl moiety in "aryloxy group", is defined the same as "aryl" defined below.

Preferred embodiments of substituents in an "optionally substituted lower alkyl" include a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "optionally substituted lower alkyl" include methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, phenethyl, 4-hydroxybenzyl, 4-methoxybenzyl, 4-carboxybenzyl, and the like.

"Carbocyclic group" includes cycloalkyl, cycloalkenyl, aryl and non-aromatic fused carbocyclic groups, and the like.

"Cycloalkyl" is a carbocyclic group having 3-10 carbons, preferably 3-8 carbons, more preferably 4-8 carbons, and includes, for example, cyclopropyl, cyclobutyl, cyclopentyl, cyclohexyl, cycloheptyl, cyclooctyl, cyclononyl, cyclodecyl, and the like.

"Cycloalkenyl" includes those in which the ring of the cycloalkyl has at least one double bond at any position(s), and specifically includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like, and in particular, phenyl is preferable.

"Aromatic carbocycle" means a ring derived from aryl as described above.

"Aromatic heterocycle" means a aromatic ring, which is monocyclic or bicyclic or more, having same or different one or more hetero atom selected independently from O, S or N.

"Non-aromatic carbocyclic group" includes those selected from the above "cycloalkyl", "cycloalkenyl" and "aryl" and specifically includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptynyl, cyclooctynyl, and cyclohexadienyl, phenyl, naphthyl, anthryl and phenanthryl and the like.

"Non-aromatic fused carbocyclic group" includes a group in which two or more cyclic groups selected from the "cycloalkyl", "cycloalkenyl," and "aryl" are fused, and specifically includes, for example, indanyl, indenyl, tetrahydronaphthyl, and fluorenyl, and the like.

"Heterocyclic group" includes heterocyclic groups having at least one hetero atom arbitrarily selected from O, S, and N, in the ring thereof, and specifically includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, triazolyl, thiadiazolyl, furyl, thienyl, and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dibenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihydrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, heterocyclic group is a 5- or 6-membered heteroaryl or non-aromatic heterocyclic group, and more preferably, a 5- or 6-membered heteroaryl.

Substituents of an "optionally substituted carbocyclic group" and an "optionally substituted heterocyclic group", an "optionally substituted non-aromatic carbocyclic group", an "optionally substituted non-aromatic heterocyclic group" include optionally substituted lower alkyl, and at least one group selected from the above Substituent Group Alpha.

Preferred embodiments of substituents in an "optionally substituted carbocyclic group" and an "optionally substituted heterocyclic group" include methyl, ethyl-isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Examples or embodiments of each site of Formula (I) are provided below. However, the scope of the subject invention is not limited to those described below.

"W" is —$CH_2$—, —S— or —O—. Preferably "W" is —$CH_2$—.

"U" is —$CH_2$—, —S—, —S(=O)— or —O— when "W" is —$CH_2$—, and preferably, "U" is —S—.

"U" is —$CH_2$— when "W" is —S— or —O—.

"L" is a single bond, an optionally substituted lower alkylene, an optionally substituted lower alkenylene, an optionally substituted lower alkynylene. Preferably, "L" is a single bond, —$CH_2$—, —CH=CH— or —CH=CH—$CH_2$—.

More preferably, "L" is a single bond or —CH$_2$—. Binding pattern of double bond between carbon atoms in L may be cis or trans, or mixture thereof.

Examples of an "optionally substituted carbocyclic group or optionally substituted heterocyclic group" of R$^1$ include phenyl and hydroxyphenyl; phenyl and hydroxyphenyl which have a halogen as a substituent; aminothiazole; aminothiazole which have a halogen as a substituent; aminothiadiazole; thiophene; furan; benzothiazole; pyridine; pyrimidine; pyridazine; aminopyridine; and the like. Preferred Examples includes the groups as follows:

[Formula 37]

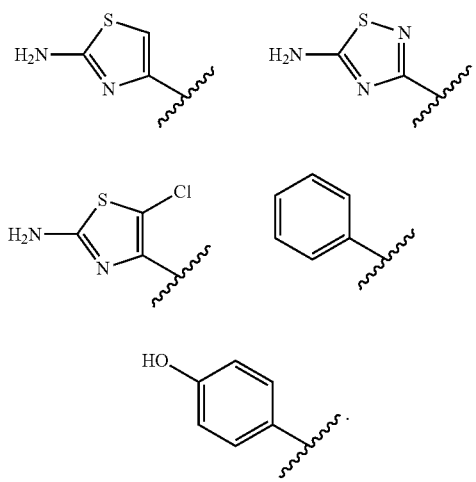

When R$^{2B}$ is hydrogen atom, examples of R$^{2A}$ include hydrogen atom, optionally substituted amino group, —COOH, —SO$_3$H, optionally substituted aminosulfonyl group, carboxyl group, optionally substituted carbamoyl group, hydroxyl group, or substituted carbonyloxy group, and the like. For example, preferred examples of

[Formula 38]

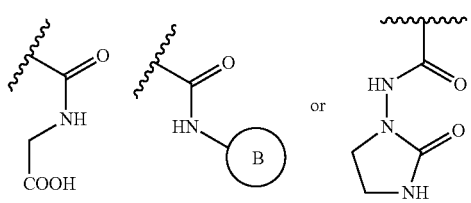

include a substituted amino group shown below:

[Formula 39]

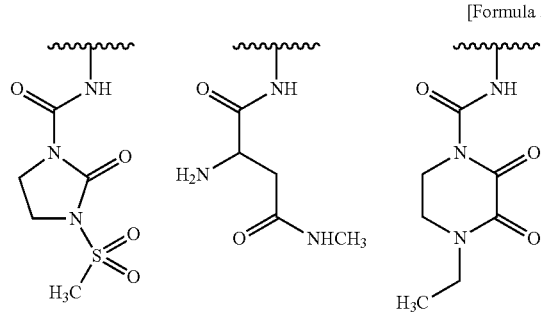

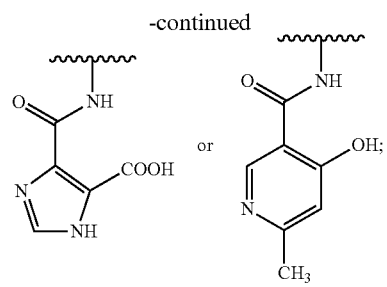

a substituted aminosulfonyl group shown below:

[Formula 40]

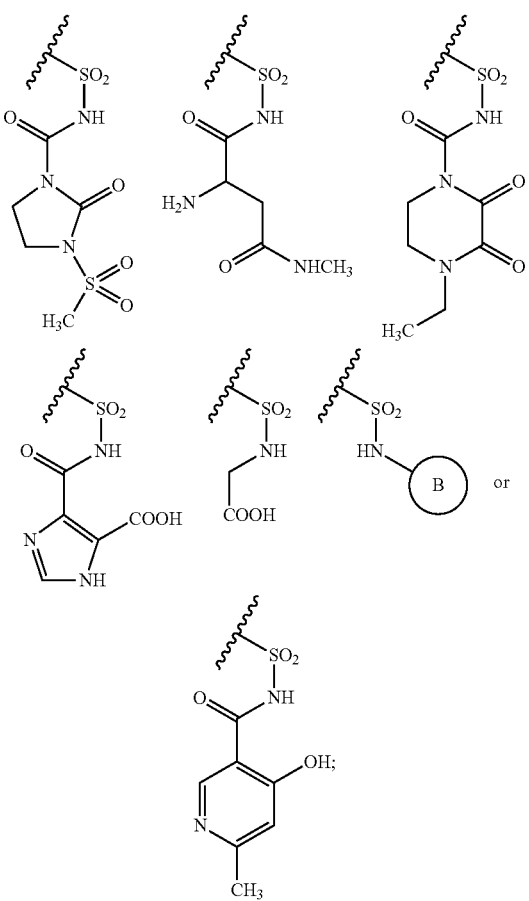

(wherein ring B represents an optionally substituted heterocyclic group);

a substituted carbamoyl group shown below:

[Formula 41]

(wherein ring B represents an optionally substituted heterocyclic group); or a substituted carbonyloxy group shown below:

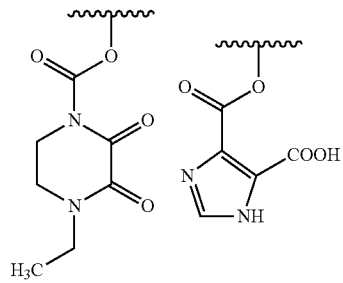

[Formula 42]

(wherein ring B represents an optionally substituted.)

Alternatively, $R^{2A}$ and $R^{2B}$ may be taken together to form a substituted methylidene group shown below:

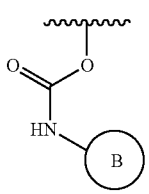

[Formula 43]

(wherein $R^9$ is an optionally substituted lower alkyl.), preferably, it is the radical shown below.

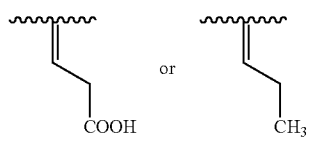

[Formula 44]

Also, $R^{2A}$ and $R^{2B}$ may be taken together to form an optionally substituted hydroxyimino group shown below:

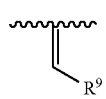

[Formula 45]

(wherein $R^9$ is as defined above.), Preferably it is the group shown below.

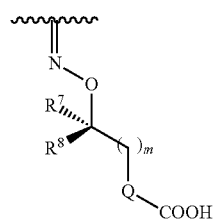

[Formula 46]

(wherein each symbol is as defined above.)

Examples of "$R^7$ and $R^8$" includes a hydrogen atom, a fluorine atom, a chlorine atom, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, phenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, triazolyl, thiadiazolyl, furyl, thienyl, and the like.

Preferred combinations of $R^7$ and $R^8$ include, as ($R^7$, $R^8$), (a hydrogen atom, a hydrogen atom), (methyl, a hydrogen atom), (a hydrogen atom, methyl), (methyl, methyl), (ethyl, a hydrogen atom), (a hydrogen atom, ethyl), (ethyl, ethyl), (phenyl, a hydrogen atom), (a hydrogen atom, phenyl), (carboxymethyl, a hydrogen atom), (a hydrogen atom, carboxymethyl), (carboxyethyl, a hydrogen atom), (a hydrogen atom, carboxyethyl), (hydroxyethyl, a hydrogen atom), (a hydrogen atom, hydroxylethyl), (carbamoylmethyl, a hydrogen atom), (a hydrogen atom, carbamoylmethyl), (trifluoromethyl, a hydrogen atom), (carboxy, a hydrogen atom), (carbamoylethyl, a hydrogen atom), (benzyl, a hydrogen atom), (4-hydroxybenzyl, a hydrogen atom), and the like.

Preferred examples of the above hydroxyimino group include groups shown below:

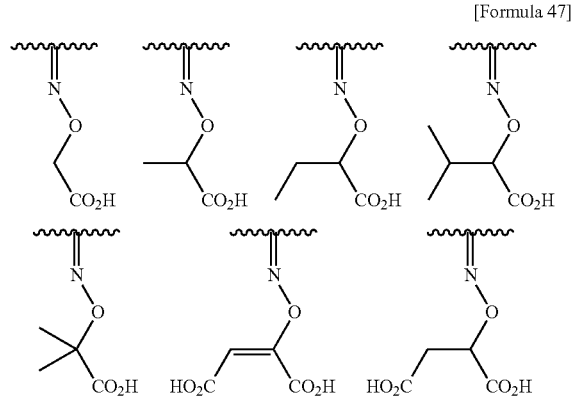

[Formula 47]

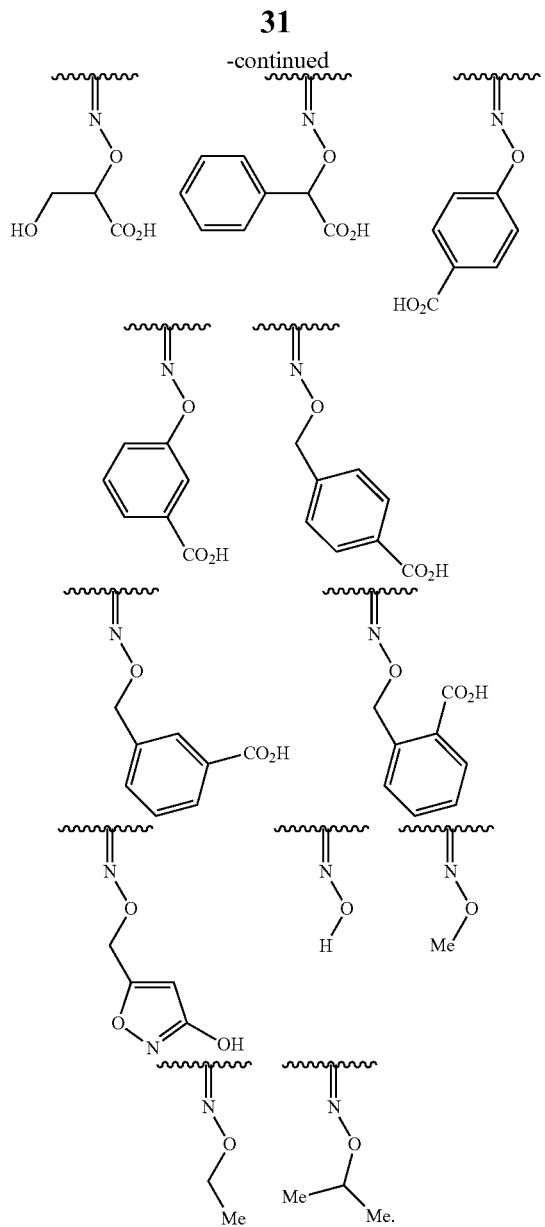

In the case where "R⁷ and R⁸ may be taken together with a neighboring atom to form an optionally substituted carbocyclic group or an optionally substituted heterocyclic group", R⁷ and R⁸ in the formula:

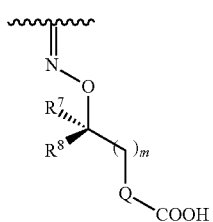

[Formula 48]

wherein each symbol is as defined above is preferred, may form cycloalkane, cycloalkene, or a non-aromatic heterocycle optionally substituted on the ring with a group selected from the above Substituent Group Alpha. For example,

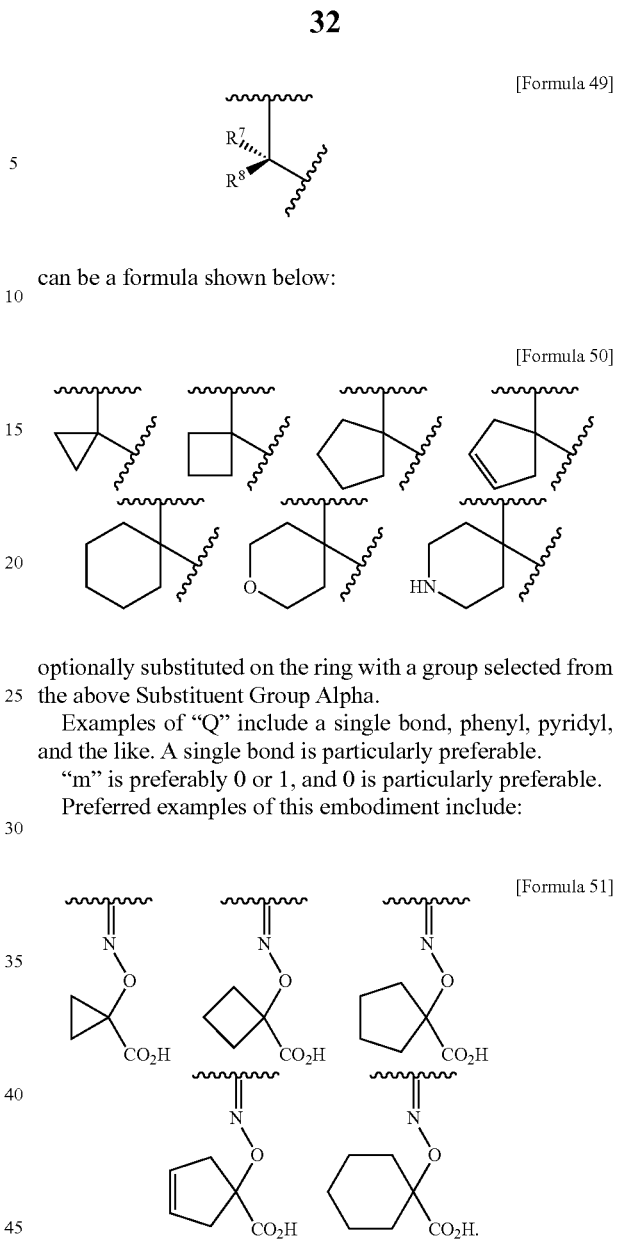

can be a formula shown below:

optionally substituted on the ring with a group selected from the above Substituent Group Alpha.

Examples of "Q" include a single bond, phenyl, pyridyl, and the like. A single bond is particularly preferable.

"m" is preferably 0 or 1, and 0 is particularly preferable.

Preferred examples of this embodiment include:

"R³" is preferably a hydrogen atom or —OCH₃, and more preferably a hydrogen atom.

The term "bioisoster" as used herein refers to a group having chemical and physical similarities that provides similar biological properties. Accordingly, "a bioisoster of carboxyl ion" of the subject invention refers to any group that provides biological properties similar to those provided by carboxyl ion, specifically refers to a group that is comparatively similar to carboxyl ion (—COO⁻) in its chemical structure, that is expected for physical properties, such as acidity, water solubility and/or disposition, equivalent to those of carboxyl ion, and that has an acidic proton. Said acidic proton moiety may form a salt, such as an alkali metal salt (e.g., sodium salt). Examples can be found in literatures, such as J. Med. Chem. 1992, 35, 1176-1183, J. Med. Chem. 1993, 36, 2485-2493, J. Med. Chem. 1992, 35, 3691-3698, J. Med. Chem. 1995, 38, 617-628, Med. Res. Rev. 1983, 3, 91-118, J. Med. Chem. 2001, 44, 1560-1563, Bioorganic & Medicinal Chemistry Letters, Vol. 4, No. 1, 41-44, 1994. Preferably, it is selected from —SO₃⁻, —SO₂—N⁻—R¹³, —PO⁻—(OR¹³), —PO$_2^-$—(OR$^{13}$), —N$^-$—CO—R$^{13}$, —CO—N$^-$—OR$^{13}$, —CO—NH—N$^-$—SO$_2$—R$^{13}$, —CO—N$^-$—SO$_2$—R$^{13}$, —CO—CH=C(O$^-$)—R$^{13}$, —N$^-$—SO$_2$—R$^{13}$, —CO—N$^-$—SO$_2$—R$^{13}$, —N$^-$—SO$_2$—R$^{13}$, —CO—N$^-$—CO—R$^{13}$, —CO—N$^-$—SO$_2$—R$^{13}$, —N$^-$—CO—R$^{13}$

[Formula 52]

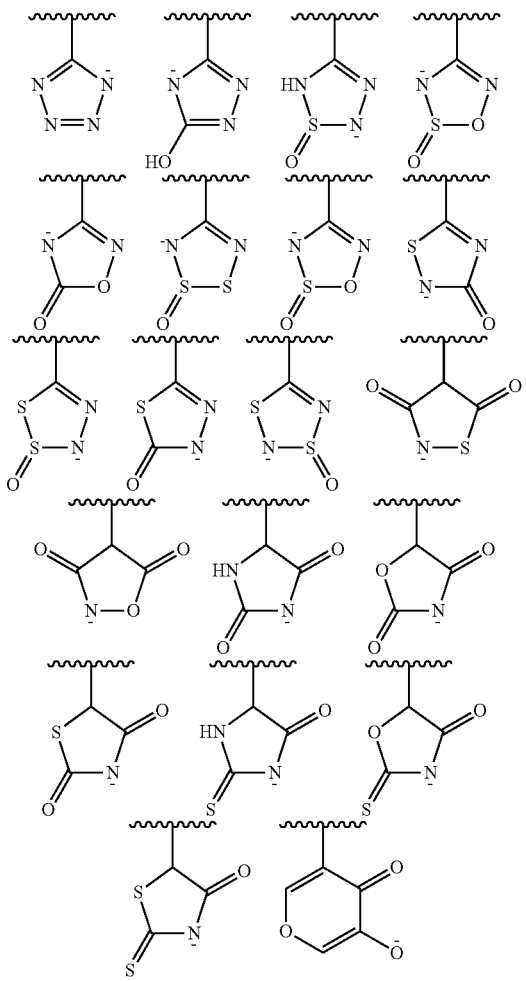

[Formula 53]

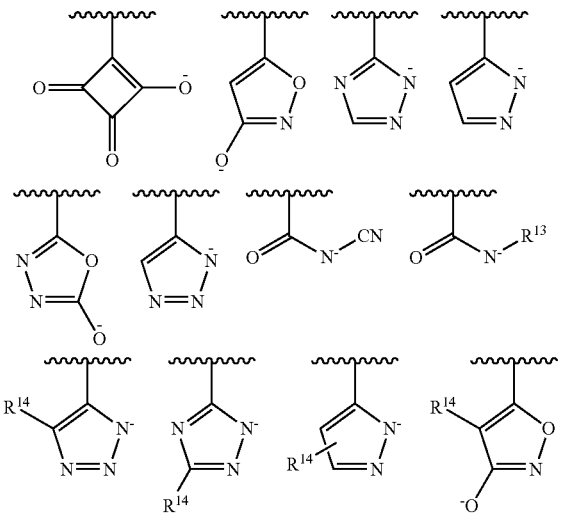

[Formula 54]

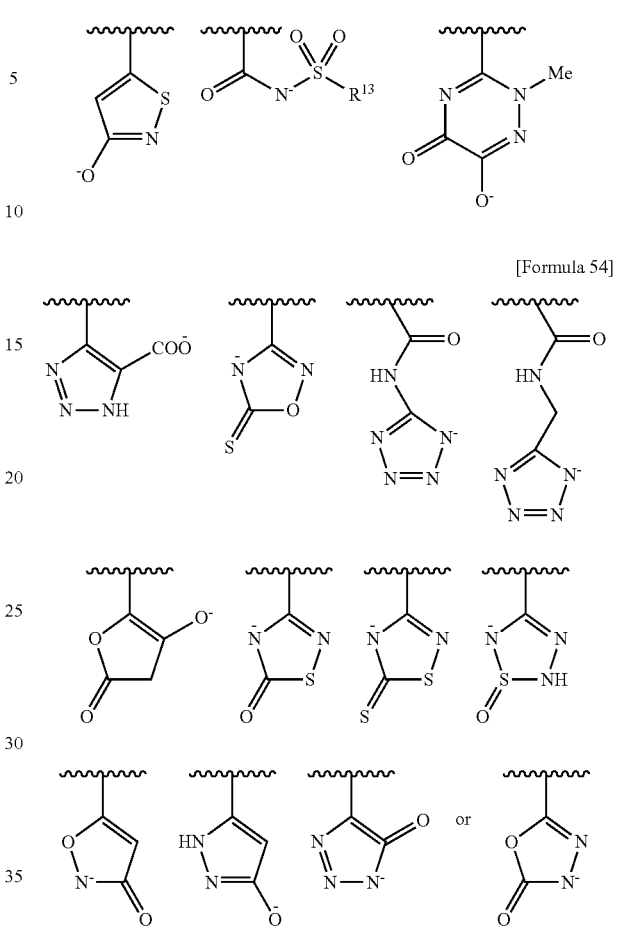

wherein R$^{13}$ is selected from the group consisting of hydrogen, hydroxyl group, halogen, an optionally substituted lower alkyl group, an optionally substituted lower alkenyl group, an optionally substituted lower alkynyl group, an optionally substituted lower alkoxy group, an optionally substituted amino group, (lower alkenyl)oxy group, an optionally substituted aryloxy group, cyano, nitro, imino, mercapto, (lower alkyl)thio group, (lower alkyl)sulphonyl group, an optionally substituted carbocyclic group, an optionally substituted heterocyclic group and —CO$_2$R$^{17}$ wherein R$^{17}$ is hydrogen, lower alkyl group or lower alkenyl group; and R$^{14}$ is an electron-withdrawing group.

[Formula 55]

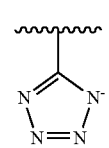

is more preferable.

R$^{14}$ is not limited so long as it is a electron-withdrawing group. Preferred examples of R$^{14}$ include fluorine, —CHF$_2$, —CF$_3$, —CONH$_2$, —CN, —C=N—OH, —SO$_2$CH$_3$ or —SO$_2$NH$_2$.

The group of the formula:

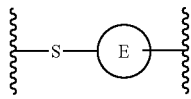
[Formula 56]

is preferably selected from the formulae:

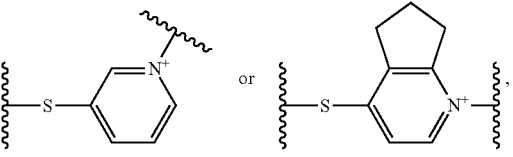

and most preferably is

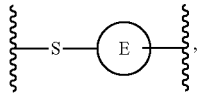
[Formula 59]

[Formula 57]

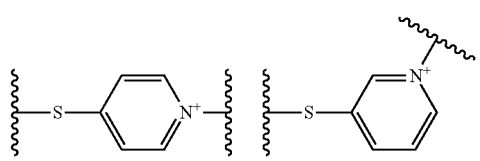

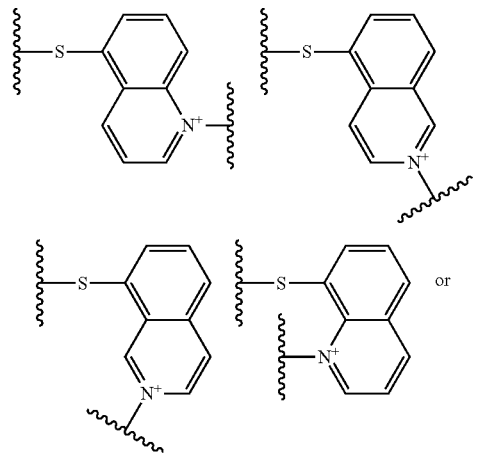

or

"Optionally substituted on the ring" means that a hydrogen atom on the carbon atom in the cyclic group may be replaced with an optionally substituted lower alkyl or with same or different one or more group selected from the above Substituent Group Alpha. Preferred embodiments of such substitutent include methyl, ethyl, isopropyl, tert-butyl, fluorine atom, chlorine atom, bromine atom, hydroxyl, carboxyl, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, (lower) alkylsulfamoyl, cyano, nitro, phenyl, cyclopropyl, cyclobutyl, cyclohexyl, pyridyl, morpholinyl, and the like. More Preferred embodiments include a ring unsubstituted or mono- or di-substituted with a hydroxyl group. Such ring mono- or di-substituted with a hydroxyl group may be substituted additionally with another substituent.

In one embodiment of the invention, the group of the formula:

[Formula 60]

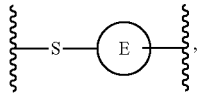

has a hydroxyl group that binds to each of two adjacent carbon atoms on an aromatic ring of the ring E. Preferred examples include the formulae shown below:

which is optionally substituted on the ring, and more preferably selected from the formulae:

[Formula 61]

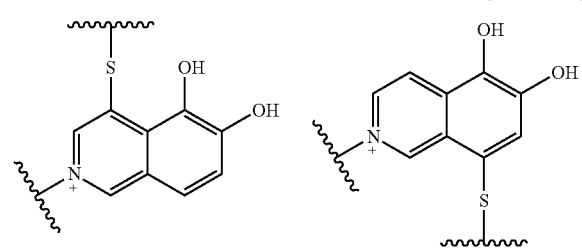

[Formula 58]

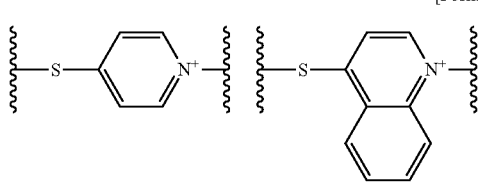

-continued
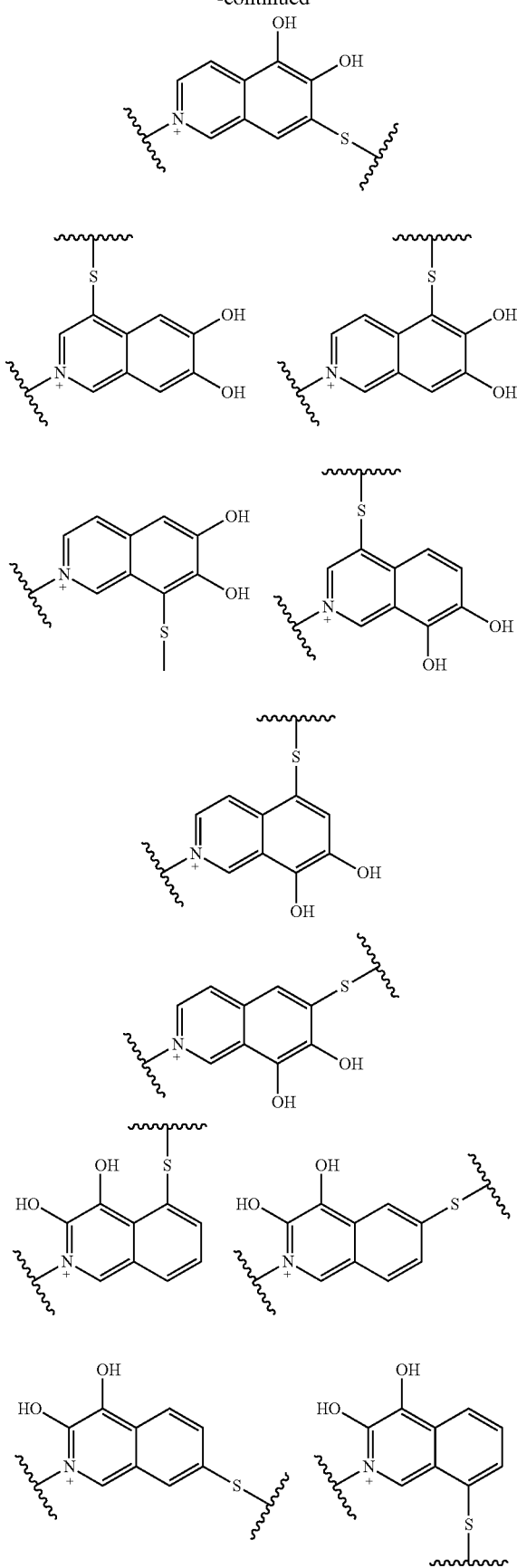
-continued
[Formula 62]
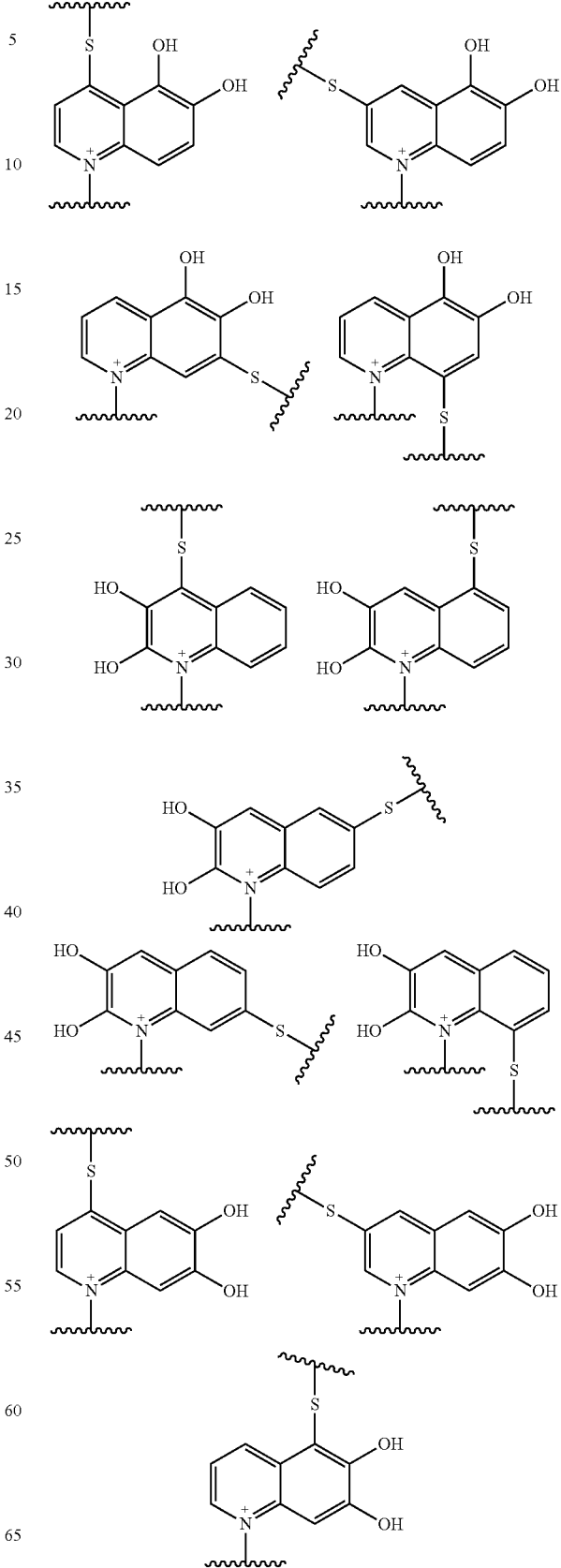

-continued

[Formula 63]

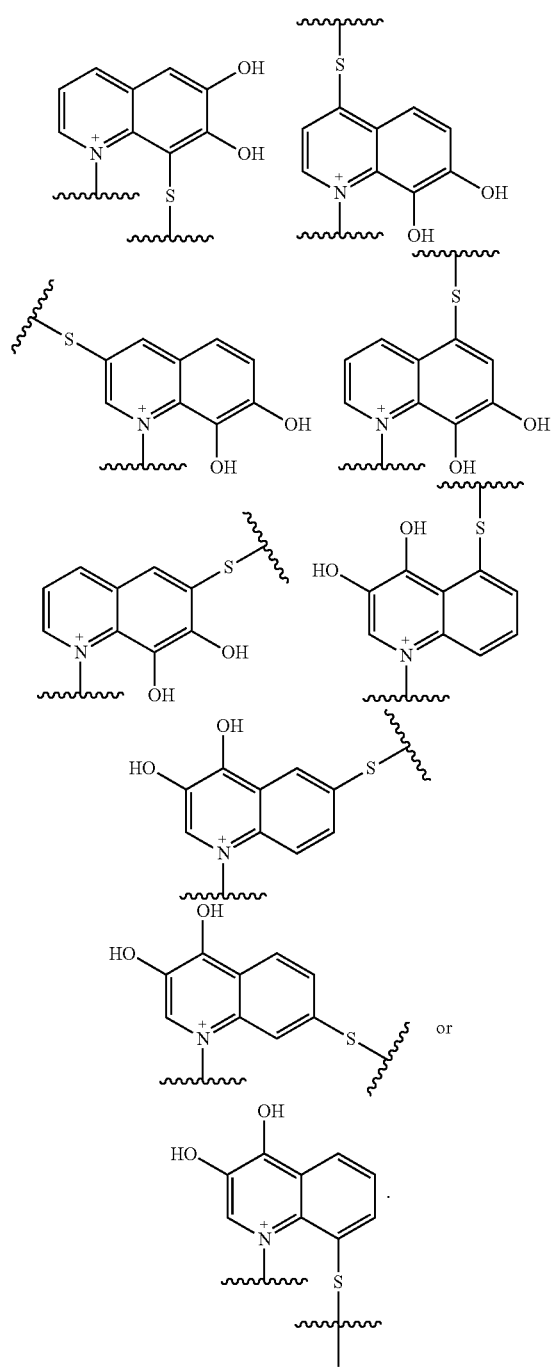

In the formula (I), examples of $R^{10}$ when $R^{10}$ is —$R^{12}$ include hydrogen atom, halogen, hydroxyl group, —$SO_3H$, an optionally substituted amino group, an optionally substituted carboxyl group, an optionally substituted carbamoyl group, an optionally substituted acyl group, an optionally substituted amino sulfonyl group, an optionally substituted alkyl group, an optionally substituted alkenyl group, an optionally substituted alkynyl group, an optionally substituted non-aromatic carbocyclic group or an optionally substituted non-aromatic heterocyclic group. Preferably, $R^{12}$ is hydrogen atom or an optionally substituted alkyl group.

Preferred embodiments wherein $R^{10}$ is a group represented by the formula:

[Formula 64]

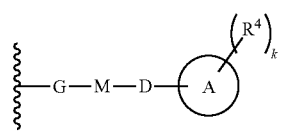

are provided below.

G is preferably a single bond or an optionally substituted lower alkylene group, and more preferably methylene or ethylene.

M is preferably a single bond or a group represented by the formula:

[Formula 65]

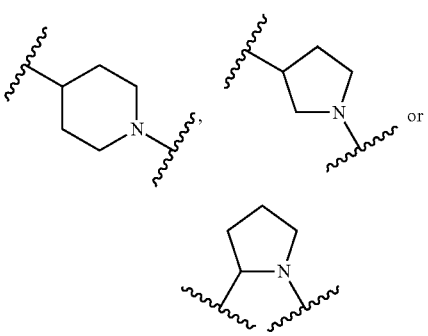

wherein the bond of the left side is attached to G and the bond of the right side is attached to D.

D is preferably a single bond, —CO—, —O—CO—, —CO—O—, —NH—, —NH—CO—, —CO—NH—, —NH—CO—NH—, —O—, —S—, —SO—, —$SO_2$—NH—, —NH—$SO_2$—, —$CH_2$—NH—CO— or —$SO_2$—, and more preferably a single bond, —CO— or —NH—CO—.

Preferable examples of "-G-M-D-" include the below cases:

(1) G is lower alkylene, M is single bond, and D is —CO— or —CO—NH—, (2) G, M, and D are all single bonds.

Preferable examples of "-ring E-G-M-D-" include the formulae as shown below:

[Formula 66]

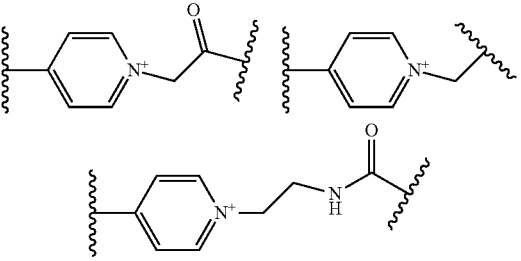

-continued

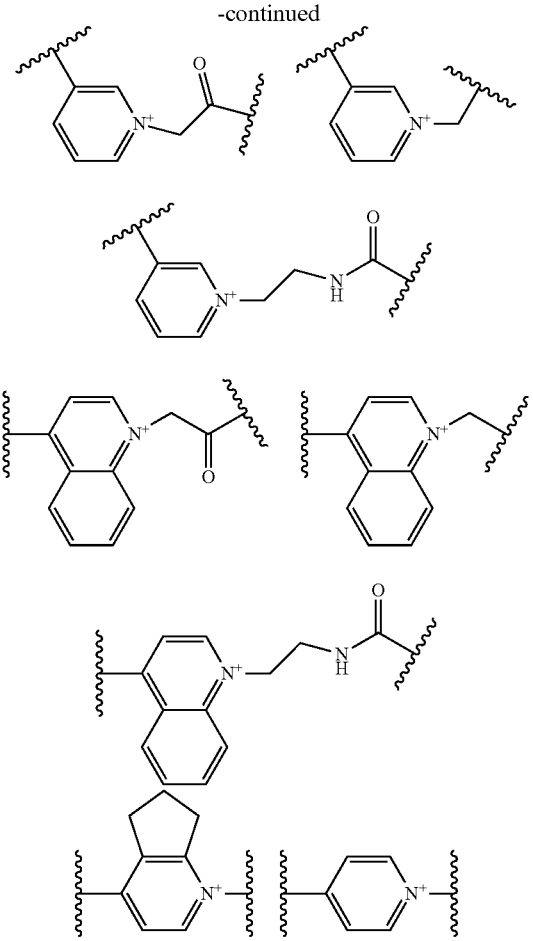

(wherein the bond of the left side is attached to L and the bond of the right side is attached to ring A.

Examples of "$R^4$" include hydrogen atom, chlorine atom, fluorine atom, bromine atom, cyano, hydroxyl, acetyl, methoxy, ethoxy, trifluoromethyl, and the like. Preferably, a hydroxyl groups cannot be bind to two adjacent carbon atoms on ring A when a hydroxyl group binds to each of two adjacent carbon atoms on an aromatic ring of the ring E. Preferably, $R^4$ is a hydrogen atom, hydroxy, methoxy, fluorine atom, trifluoromethyl, or chlorine atom. At least two $R^4$ are hydroxyl groups that bind respectively to adjacent carbon atoms on ring A when cases other than a hydroxyl group bind to each of two adjacent carbon atoms on an aromatic ring of the ring E.

"k" is an integer of 2 to 5. As ring A is a benzene ring or a 6-membered aromatic heterocyclic group having 1-3 nitrogen atoms, k is 5 when the ring A is a benzene ring, and k is 2 when the ring A is a 6-membered aromatic heterocyclic group having 3 nitrogen atoms.

When at least two $R^4$ are hydroxyl groups which bind respectively to adjacent carbon atoms on ring A, examples of the group of the formula:

[Formula 67]

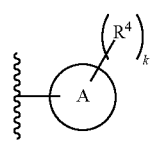

include the formulae shown below:

[Formula 68]

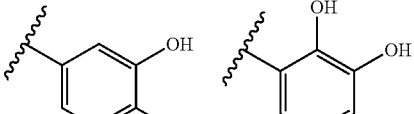
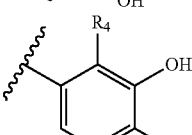
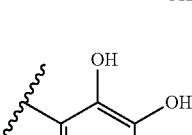
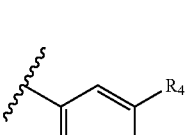
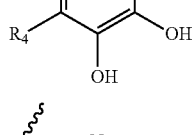
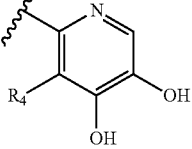
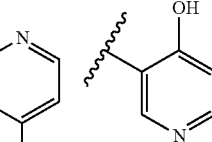
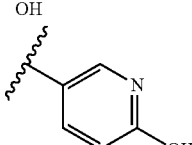
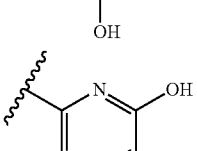
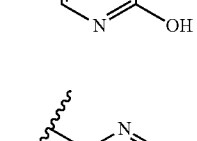
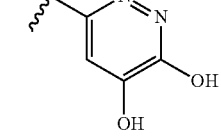

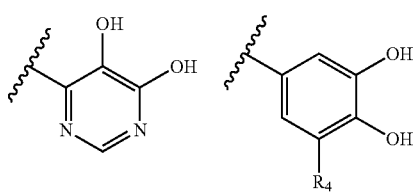

wherein R⁴ is independently halogen, hydroxyl group, —CN, —C(=O)—R⁵, —C(=O)—OH, —C(=O)—OR⁵ or —OR % preferably, selected from the formulae shown below:

[Formula 69]

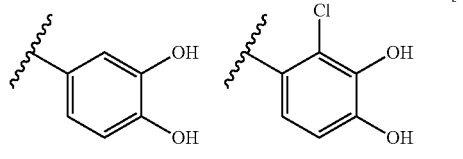

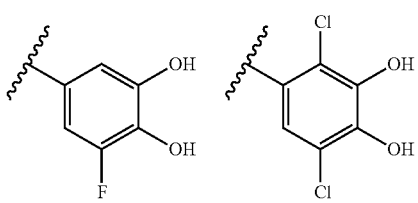

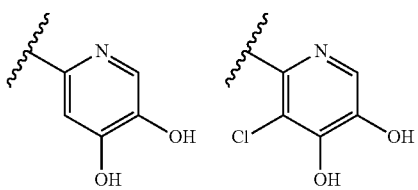

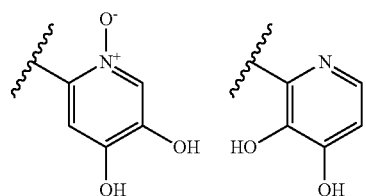

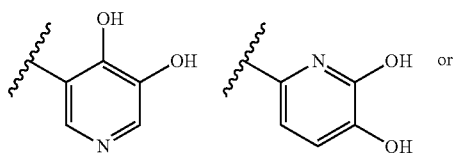

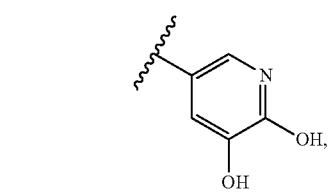

and more preferably, selected from the formulae shown below:

[Formula 70]

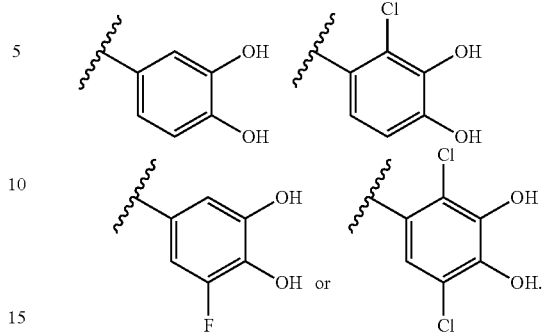

The nomenclature of the substitution position on the Cephem skeleton of Formula (I) is as follows. As used herein, 3-side chain, 4-side chain and 7-side chain respectively refer to groups binding to the 3-position, 4-position and the 7-position of the Cephem skeleton as shown below

[Formula 71]

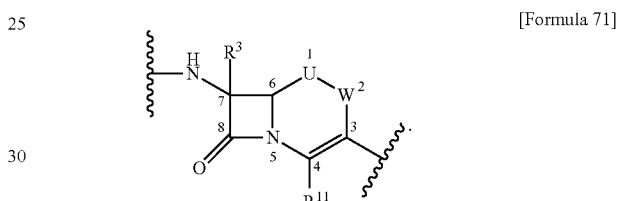

Esters of Formula (I) preferably include those esters at the 7-side chain. Esters at the carboxyl group on the 7-side chain include compounds having a structure in which the carboxyl group of an optionally substituted amino group, optionally substituted aminosulfonyl group, carboxyl group, optionally substituted (lower)alkyloxycarbonyl group, optionally substituted carbamoyl group, substituted carbonyloxy group, or the like at the terminal of R¹, R²ᴬ or R²ᴮ shown in the formula:

[Formula 72]

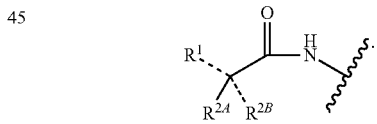

wherein each symbol is as defined above, is esterified (for example, in the case of carboxyl (—COOH), such esters are represented by the structural formula —COORᵃ, which is shown with Rᵃ representing an ester residue such as a carboxyl-protecting group or the like); and the like. Such esters include those esters that are easily metabolized in the body to form a carboxylic state.

The aforementioned protecting groups for a carboxyl group or the like may be of any group as long as it can be protected and/or deprotected by a method described in Protective Groups in Organic Synthesis, written by T. W. Greene, John Wiley & Sons Inc. (1991), or the like. Examples thereof include lower alkyl (e.g., methyl, ethyl, t-butyl), (lower)alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

Amino-protected compounds at the amino on the 7-side chain of Formula (I) refer to the structures in which the amino on the ring has been protected, as shown in the formula:

[Formula 73]

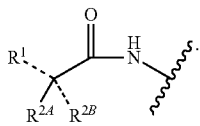

wherein each symbol is as defined above; and when $R^1$ and/or $R^{2A}$ has an amino group, the protected compound is represented by the formula —$NHR^c$ wherein $R^c$ represents an amino-protecting group. Such amino-protecting groups include those groups that are readily metabolized in the body to form amino. The aforementioned amino-protecting groups may be of any group as long as it can be protected and/or deprotected by a method described in Protective Groups in Organic Synthesis, written by T. W. Greene, John Wiley & Sons Inc. (1991), or the like. Examples thereof include (lower)alkoxycarbonyl (e.g., t-butoxycarbonyl, benzyloxycarbonyl, p-nitrobenzyloxycarbonyl), optionally substituted aralkanoyl (e.g., benzoyl, p-nitrobenzoyl), acyl (e.g., formyl, chloroacetyl), and the like.

The Compound (I) of the subject invention is not limited to particular isomers, but includes any possible isomers (e.g., keto-enol isomer, imine-enamine isomer, diastereoisomer, optical isomer, rotamer, etc.), racemates and a mixture thereof.

For example,

[Formula 74]

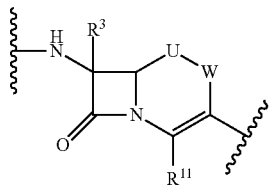

in Formula (I) includes

[Formula 75]

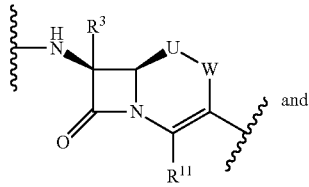

and

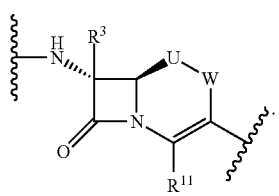

The compound (I) of the subject invention can form a zwitter ion between a quaternary ammonium ion on the group "E" and a substituent on the 4-side chain (i.e., a bioisoster of carboxyl ion). For example, when the substituent at the 4-position is tetrazolyl group:

[Formula 76]

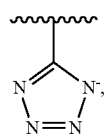

which is negatively charged, but it may take the structure

[Formula 77]

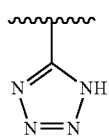

by receiving a proton from another moiety in Formula (I), and such structure should be included in the compound (I) of the subject invention. The same is true in another bioisoster of carboxyl ion.

For example, the formula:

[Formula 78]

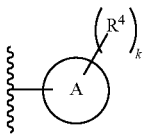

wherein each symbol is as defined above, in Formula (I) includes the following resonance structures:

[Formula 79]

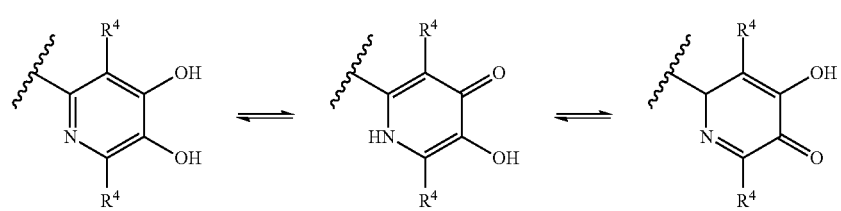

-continued

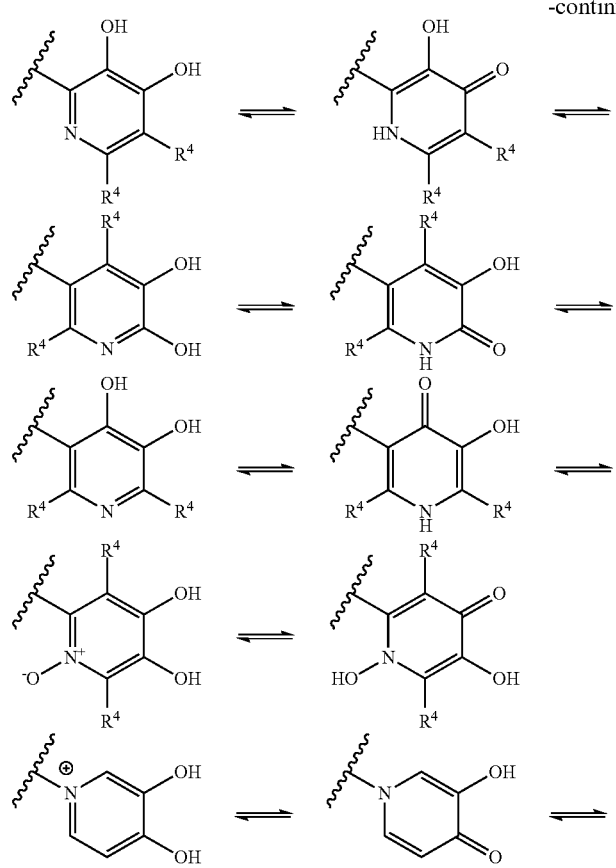
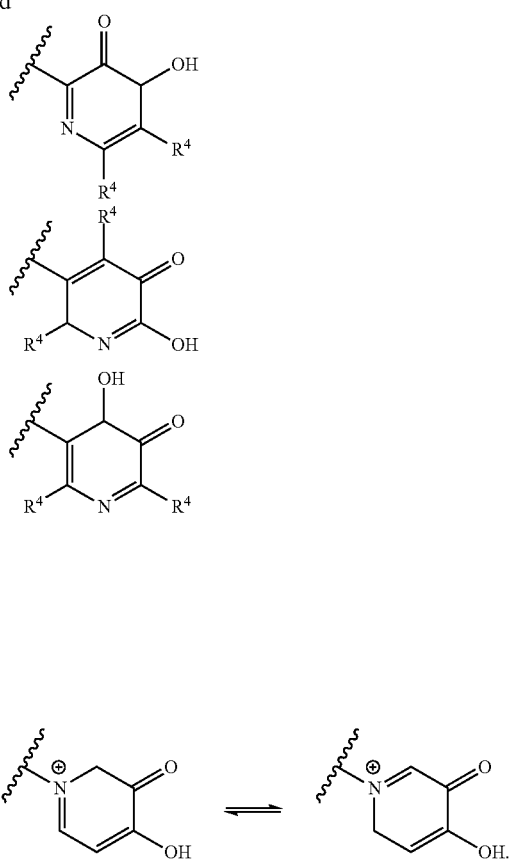

wherein R⁴ is as defined above.

At least one hydrogen atom, carbon atom and/or another atom may be replaced with an isotope of said hydrogen atom, carbon atom and/or another atom. Examples of such isotope include hydrogen, carbon, nitrogen, oxygen, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound of Formula (I) include compounds having an atom replaced with such isotope. Such compound replaced with an isotope are useful as a pharmaceutical product, and such compound include all of radiolabeled compound of Formula (I). Also, the subject invention includes any method of radioactive labeling for the production of such radiolabeled compound, and thus, it is useful in a research for metabolic pharmacokinetics, binding assay and/or as a diagnostic tool.

A radiolabeled compound of Formula (I) may be prepared according to the technique well known in the art. For example, tritium can be introduced into a specific compound of Formula (I) by catalytic dehalogenation using tritium to prepare a tritium-labeled compound of Formula (I). This method comprises reaction of a precursor which is a compound of Formula (I) appropriately halogenated with tritium gas in the presence of appropriate catalyst, such as Pd/C, in the presence or absence of a base. For another method for the preparation of a tritium-labeled compound, see the literature, Isotopes in the Physical and Biomedical Sciences, Vol. 1, Labeled Compounds (Part A), Chapter 6 (1987). $^{14}C$-labeled compound can be prepared using a starting material having $^{14}C$.

Salts of a compound of Formula (I) include those formed with an inorganic or organic acid by a carboxyl group in the 7-side chain and/or an amino group in the 7-side chain; and those formed with a counter anion by a quaternary amine moiety in the 3-side chain.

Pharmaceutically acceptable salts of a compound of Formula (I) include, for example, salts formed with alkali metal (e.g. lithium, sodium, potassium, etc.), alkaline earth metal (e.g. calcium, barium, etc.), magnesium, transition metal (e.g. zinc, ferrum, etc.), ammonia, organic base (e.g. trimethylamine, triethylamine, dicyclohexylamine, ethanolamine, diethanolamine, triethanolamine, meglumine, diethanolamine, ethylenediamine, pyrydine, picoline, quinoline, etc.) and amino acid, or salts formed with inorganic acid (e.g. hydrochloric acid, sulphuric acid, nitric acid, carbonic acid, hydrobromic acid, phosphoric acid, hydroiodic acid, etc.), and organic acid (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulphonic acid, p-toluenesulfonic acid, methanesulphonic acid, ethanesulphonic acid, etc, particularly, salts formed with hydrochloric acid, sulphuric acid, phosphoric acid, tartaric acid, methanesulphonic acid. These salts can be formed according to the conventional method.

The compound of Formula (I) or pharmaceutically acceptable salts thereof may form a solvate (e.g., hydrate) and/or a crystalline polymorphism, and the subject invention also includes such solvates and crystalline polymorphisms. In such "solvate", any number of solvent molecules (e.g., water molecule, etc.) may be coordinated to the compound of Formula (I). By leaving the compound of Formula (I) or pharmaceutically acceptable salt thereof in the atmosphere, it may absorb moisture to adhere with absorbed water or form a hydrate thereof. Also, a crystalline polymorphism of the compound of Formula (I) or pharmaceutically acceptable salt thereof can be formed by recrystallization.

The compound of Formula (I) or pharmaceutically acceptable salt thereof may form a prodrug, and the subject invention includes such prodrug. Prodrug is a derivative of the compound of the invention having a group chemically- or metabolically-degradable to be transformed into a pharamacologically active compound by solvolysis or under physiological condition in vivo. Prodrug includes compounds which can be transformed into the compound of Formula (I) by enzymatically oxidization, reduction or hydrolysis under physiological condition in vivo, or transformed into the compound of Formula (I) by hydrolysis with gastric acid, etc. Methods for selection and production of appropriate prodrug derivative can be found, for example, in Design of Prodrugs, Elsevier, Amsterdam 1985.

Prodrug may be active compound in itself.

When the compound of Formula (I) or pharmaceutically acceptable salt thereof has a hydroxyl group, acyloxy derivatives or sulfonyloxy derivatives can be prepared as a prodrug. For example, such compound having a hydroxyl group may be reacted with an appropriate acyl halide, acid anhydrate or an appropriate sulfonyl chloride, sulfonyl anhydrate, mixed anhydrate, etc., or may be reacted using a coupling agent, such as for examples, those having $CH_3COO\text{—}$, $C_2H_5COO\text{—}$, $t\text{-}BuCOO\text{—}$, $C_{15}H_{31}COO\text{—}$, $PhCOO\text{—}$, $(m\text{-}NaOOCPh)COO\text{—}$, $NaOOCCH_2CH_2COO\text{—}$, $CH_3CH(NH_2)COO\text{—}$, $CH_2N(CH_3)_2COO\text{—}$, $CH_3SO_3\text{—}$, $CH_3CH_2SO_3\text{—}$, $CF_3SO_3\text{—}$, $CH_2FSO_3\text{—}$, $CF_3CH_2SO_3\text{—}$, $p\text{-}CH_3\text{—}O\text{-}PhSO_3\text{—}$, $PhSO_3\text{—}$, $p\text{-}CH_3PhSO_3\text{—}$.

(General Synthetic Method)

As disclosed in the following general synthetic method and Examples, the present compound of the formula (I) may be obtained by binding a side chain moiety on the 3-, 4- and 7-positions on the Cephem backbone. The present compound may be synthesized, for example, by the following general synthetic method.

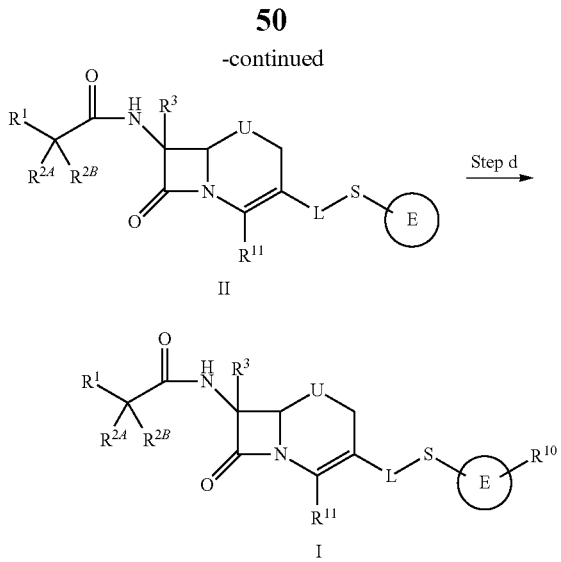

wherein U, L, Ring E, $R^1$, $R^{2A}$, $R^{2B}$, $R^3$, $R^{10}$ and $R^{11}$ are as defined above, Y is a leaving group (e.g., hydroxy, a halogen (Cl, Br, I), an optionally substituted carbamoyloxy, acyloxy, methanesulfonyloxy, toluenesulfonyloxy, etc.), $R^a$ is a hydrogen atom or an amino-protecting group, $R^b$ is a hydrogen atom or a carboxy-protecting group.

1) Step a

The compound (V) may be obtained by reacting the compound (VII), which is commercially available one or prepared according the method disclosed in the literatures (e.g., JP-A-60-231684, JP-A-62-149682, etc.) and a tertiary amine corresponding to the structure: —S-Ring E- (Ring E is the same as defined above). In this case, $R^b$ is preferably a carboxy-protecting group. In preferred embodiment, a structure: —S-Ring E- is S-pyridinium group, and the compound (V) may be prepared according to the following procedures.

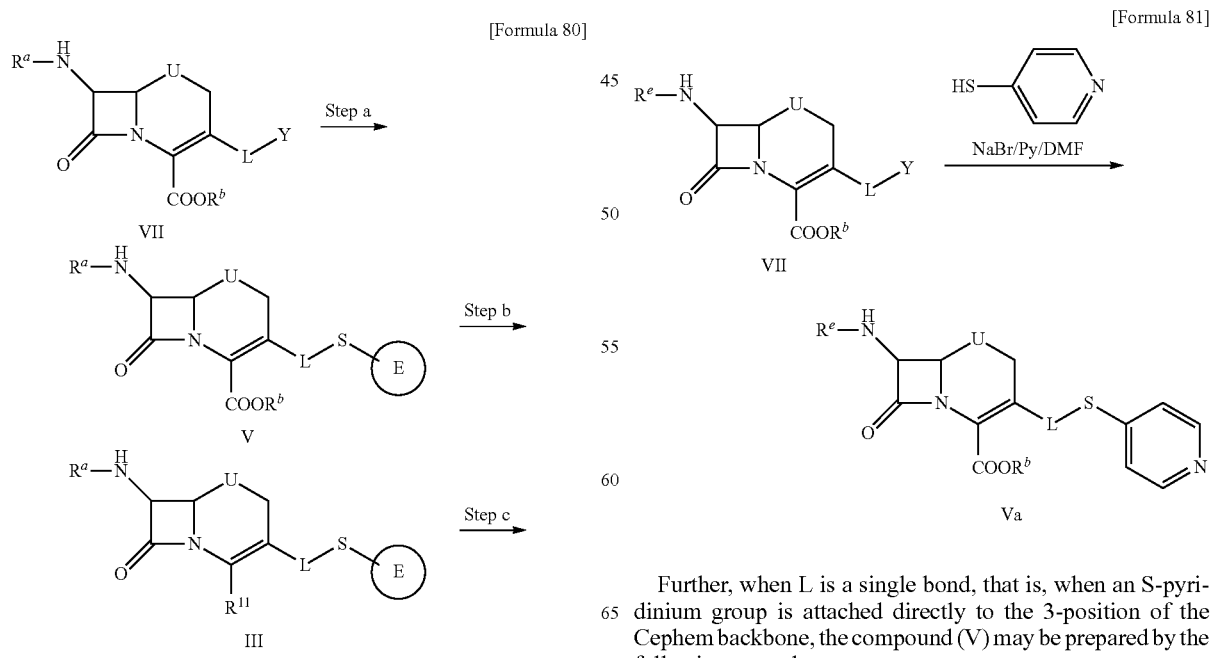

Further, when L is a single bond, that is, when an S-pyridinium group is attached directly to the 3-position of the Cephem backbone, the compound (V) may be prepared by the following procedures.

[Formula 82]

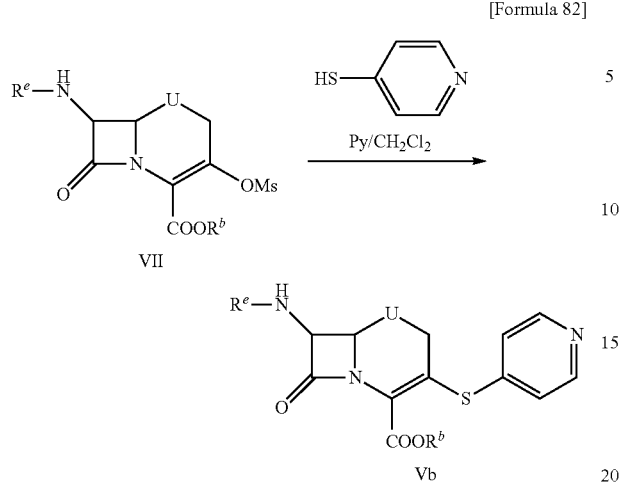

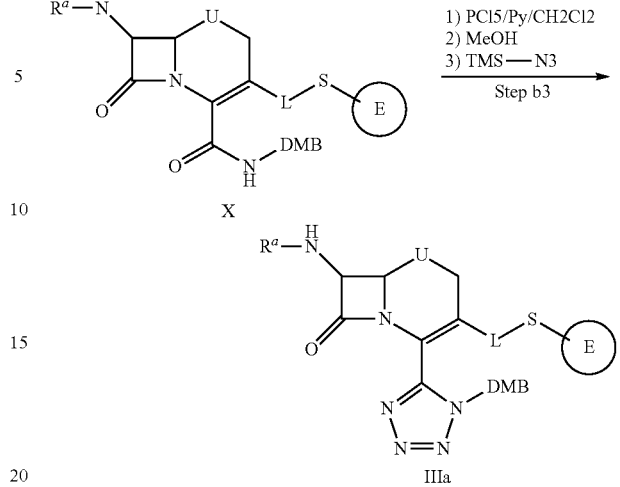

The above corresponding tertiary amine is usually used in an amount of 1 to 5 moles, preferably in an amount of 1 to 2 moles, to 1 mole of the compound (VII).

The reaction solvent includes, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., acetonitrile (MeCN), propionitrile), dimethylsulfoxide, water, or a mixed solvent of these solvents.

The reaction temperature is usually in the range of from −20° C. to 60° C., preferably in the range of from −10° C. to 40° C., more preferably in the range of from 0° C. to 20° C.

2) Step b

By a conventional method well known to one skilled in the art, the compound (III) is obtained by converting the 4-carboxyl group of the compound (V) into a desired bioisoster. In preferred embodiment, the 4-side chain (i.e., $R^{11}$) is a tetrazolyl group, and the compound (III) may be obtained, for example, by the following procedures.

[Formula 83]

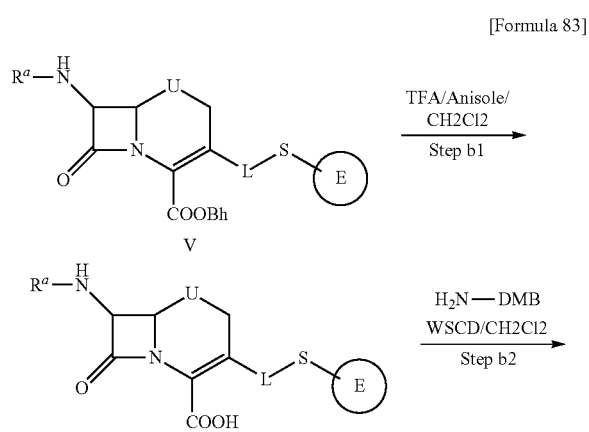

As shown in the above, the compound (X) is obtained by deprotecting the 4-carboxy-protecting group of the compound (V) by a conventional method (Step b1), followed by aminating said carboxyl group by a conventional method (Step b2). This amination reaction may be carried out, as shown in the above, by using an amine compound which is previously protected by a protecting group such as dimethoxybenzyl (DMB) group, etc., or alternatively, the 4-side chain amino group may be protected after the amination reaction. The preferred protecting group includes aminoprotecting groups as exemplified below. The reaction solvent includes, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, etc., or a mixed solvent of these solvents.

The reaction temperature is usually in the range of from about

−100 to 100° C., preferably in the range of from about −80 to 50° C., more preferably in the range of from about −80 to −40° C. The reaction temperature may vary according to the reagents, solvents or reaction temperature to be employed, but the reaction is usually carried out for 0.5-24 hours.

The compound (IIIa) is obtained by reacting the compound (X) with hydrogen azide, trimethylsilyl azide (TMSN$_3$), hydrazoates (e.g., sodium azide, tetra-n-butyl ammonium azide, tetramethylguanidium azide), etc. to form a tetrazole ring (Step b3).

Trimethylsilyl azide is usually used in an amount of about 1 to 100 moles, preferably in an amount of 1 to 30 moles, to 1 mole of the compound (X). The reaction solvent includes, for example, water, alcohols (e.g., methanol, ethanol, etc.), carboxylic acids (e.g., acetic acid, etc.). The reaction temperature is usually in the range of from about 0 to 100° C., preferably in the range of from about 10 to 90° C., more preferably in the range of from about 10 to 50° C. The reaction period may vary according to the reagents, solvents or reaction temperature to be employed, but the reaction is usually carried out for 0.5-24 hours.

3) Step c

The compound (II) may be obtained by reaction the compound (III) with a compound of the formula:

[Formula 84]

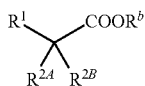

XI (wherein $R^b$ is a hydrogen atom or a carboxy-protecting group, and the other symbols are as defined above), which corresponds to a desired 7-side chain. The compound of the formula (XI) may be a commercially available one and/or may be obtained by a conventional method.

The compound (XI) is usually used in an amount of about 1 to 5 moles, preferably in an amount of 1 to 2 moles, to 1 mole of the compound (III).

The reaction solvent includes, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, etc., or a mixed solvent thereof.

The reaction temperature is usually in the range of from about −40 to 80° C., preferably in the range of from about −20 to 50° C., more preferably in the range of from about −10 to 30° C.

4) Step d

The compound (I) may be obtained by adding a side chain corresponding to $R^{10}$ on the quaternary ammonium at the 3-position of the compound (II) by a conventional method.

The compound (I) wherein the 3-side chain of the cephem backbone contains the structure: —S-pyridinium-benzene ring may be prepared, for example, by the following synthetic pathway. Step e, Step f and Step g may be carried out in a similar manner to the above-mentioned Steps b, a, c, respectively.

[Formula 85]

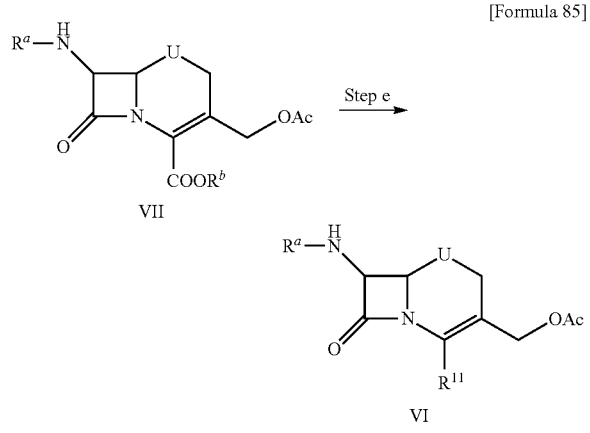

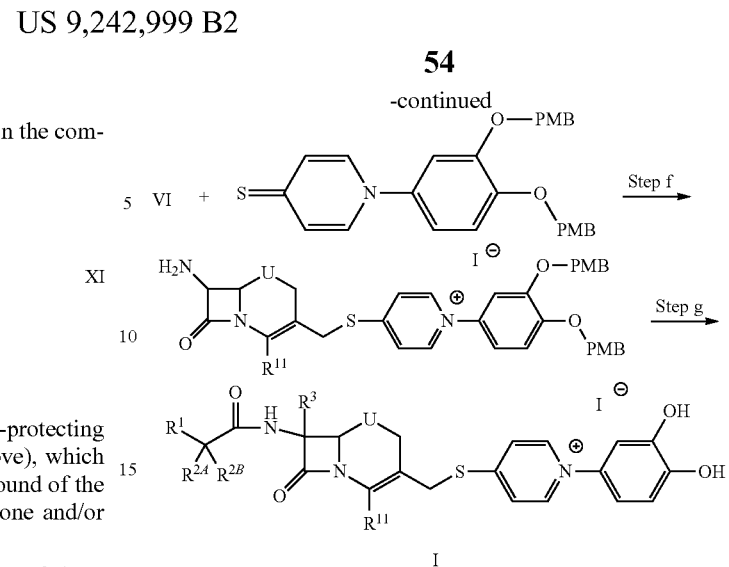

The protecting group to be used in the above reaction such as amino-protecting groups, hydroxy-protecting groups, etc. includes, for example, protecting groups described in Protective Groups in Organic Synthesis, written by T. W. Greene, John Wiley & Sons Inc. (1991), etc. Methods for the introduction and removal of a protecting group are methods commonly used in synthetic organic chemistry (see, for example, methods described in Protective Groups in Organic Synthesis, written by T. W. Greene, John Wiley & Sons Inc. (1991)), etc., or can be obtained by a modified method thereof. Furthermore, a functional group included in each substituent can be converted by a known method (e.g., those described in Comprehensive Organic Transformations, written by R. C. Larock (1989), etc.) in addition to the above production methods. Some of the compounds of the present invention can be used as a synthetic intermediate, leading to a new derivative. Intermediates and desired compounds produced in each of the above production methods can be isolated and purified by a purification method commonly used in synthetic organic chemistry, for example, neutralization, filtration, extraction, washing, drying, concentration, recrystallization, any kind of chromatography, etc. Furthermore, intermediates can be subjected to a next reaction without any purification.

For example, phthalimide, a lower alkoxycarbonyl (butoxycarbonyl (Boc) etc.), a lower alkenyloxycarbonyl (allyloxycarbonyl (Alloc), etc.), benzyloxycarbonyl, p-nitrobenzyloxycarbonyl, (substituted) aralkanoyl (p-nitrobenzoyl, etc.), an acyl (formyl, chloroacetyl, etc.), (substituted) aralkyl (trityl, etc.), benzhydryl (BH), etc. are exemplified as an amino-protecting group.

For example, a lower alkoxycarbonyl such as a $C_1$-$C_4$ alkoxycarbonyl (e.g., t-butyloxycarbonyl), a halogenated lower alkoxycarbonyl such as a halogenated ($C_1$-$C_3$) alkoxycarbonyl (e.g., 2-iodo ethyloxycarbonyl, 2,2,2-trichloroethyloxycarbonyl), an aryl-(lower) alkoxycarbonyl such as a phenyl-($C_1$-$C_4$) alkoxycarbonyl having optionally a substituent(s) on the benzene ring (benzyloxycarbonyl, o-nitrobenzyloxycarbonyl, p-nitrobenzyloxycarbonyl, p-methoxybenzyloxycarbonyl), p-methoxybenzyl (PMB), a tri-lower alkylsilyl such as a tri-($C_1$-$C_4$) alkylsilyl (e.g., trimethylsilyl, t-butyldimethylsilyl), a substituted methyl such as a $C_1$-$C_4$ alkoxymethyl (e.g., methoxymethyl), a $C_1$-$C_4$ alkoxy-($C_1$-$C_4$) alkoxymethyl (e.g., 2-methoxyethoxymethyl), a $C_1$-$C_4$ alkylthiomethyl (e.g., methylthiomethyl), tetrahydropyranyl, etc. may be exemplified as a hydroxy-protecting group.

The above-mentioned deprotecting reaction is carried out in a solvent such as tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, or a mixed solvent thereof, using a Lewis acid (e.g., $AlCl_3$, $SnCl_4$, $TiCl_4$), a protonic acid (e.g., HCl, HBr, $H_2SO_4$, HCOOH), etc.

The obtained compound is further chemically modified, and thereby an ester, or a compound of which an amino on the thiazole ring at the 7-position thereof is protected, or a pharmaceutically acceptable salt, or a solvate thereof can be synthesized.

The compounds of the present invention have a wide antimicrobial activity spectrum, and may be used for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection, etc.

The compounds of the present invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus*, etc.), Gram negative bacteria colonized in respiratory system (*Haemophilus, Moraxella*, etc.), and Gram negative bacteria of glucose non fermentation (*Pseudomonas aeruginosa, Pseudomonas* other than *P. aeruginosa, Stenotrophomonas, Burkholderia, Acinetobacter*, etc.). The compounds of the present invention are stable against beta-lactamase belonging to Classes A, B, C and D which is produced by these Gram negative bacteria, and have high antimicrobial activity against a variety of beta-lactam drug resistant Gram negative bacteria, such as ESBL producing bacteria, etc. The compounds of the present invention are extremely stable against metallo-beta-lactamase belonging to Class B including in particular IMP type, VIM type, L-1 type, etc. Thus, these are effective against a variety of beta-lactam drug resistant Gram negative bacteria including Cephem and Carbapenem. Moreover, the compounds of the present invention have antimicrobial activity against Gram positive bacteria including methicillin-resistant *Staphylococcus aureus* (MRSA), penicillin-resistant *Streptococcus pneumoniae* (PRSP), etc. Still more preferable compounds have features regarding kinetics in the body, such as high blood concentration, long duration of effects, and/or significant tissue migration. Preferable compounds of the present invention are safe in terms of side effects. Also, preferable compounds of the present invention have high water solubility, and thus preferable as an injecting drug, in particular.

The compounds of the present invention can be administered either orally or parenterally. The compounds of the present invention, when administered orally, can be used in any dosage form of normal formulations, for example, solid drug such as tablet, powder, granule, capsule, etc.; solution drug; oleaginous suspension drug; or liquid drug such as syrup or elixir. The compounds of the present invention, when administered parenterally, can be used as an aqueous or oleaginous suspended injecting agent, or nasal drops. In preparation thereof, a conventional excipient, binder, lubricant, aqueous solvent, oleaginous solvent, emulsifier, suspending agent, preservative, stabilizer, etc. can be optionally used. A formulation of the present invention is produced by combining (for example, mixing) a therapeutically effective amount of a compound of the present invention with a pharmaceutically acceptable carrier or diluent.

The compounds of the present invention may be administered either parenterally or orally as an injecting agent, capsules, tablets, and granules, and preferably administered as an injecting agent. The dosage of the present compound may usually be, per 1 kg of body weight of a patient or animal, about 0.1 to 100 mg/day, preferably, about 0.5 to 50 mg/day, if desired, divided into 2-4 times per day. Carriers when used in an injecting agent are, for example, distilled water, saline, etc., and a base and the like may be used for pH adjustment. When used as capsules, granules, or tablets, carriers may be known excipients (e.g., starch, lactose, sucrose, calcium carbonate, calcium phosphate, etc.), binders (e.g., starch, acacia gum, carboxymethyl cellulose, hydroxypropyl cellulose, crystalline cellulose, etc.), lubricants (e.g., magnesium stearate, talc, etc.), etc.

EXAMPLES

Hereinafter, the present invention is described in more details with Examples, Experiments and Formulation Example. However, the present invention is not construed to be limited thereto.

In Examples, the meaning of each abbreviation is as described below.

Ac: Acetyl
Alloc: Allyloxycarbonyl
BH: Benzhydryl
Boc: tert-Butoxycarbonyl
Bzh: Benzhydryl
BSA: N,O-bis(trimethylsilyl)acetamide
DMF: N,N-Dimethylformamide
Me: Methyl
ODS: Octadecylsilyl
PMB: p-Methoxybenzyl
t-Bu: tert-Butyl
TFA: Trifluoroacetic acid
WSCD: N-Ethyl-N'-(3-dimethylaminopropyl)carbodiimide Preparation 1: Production of Compound 1h

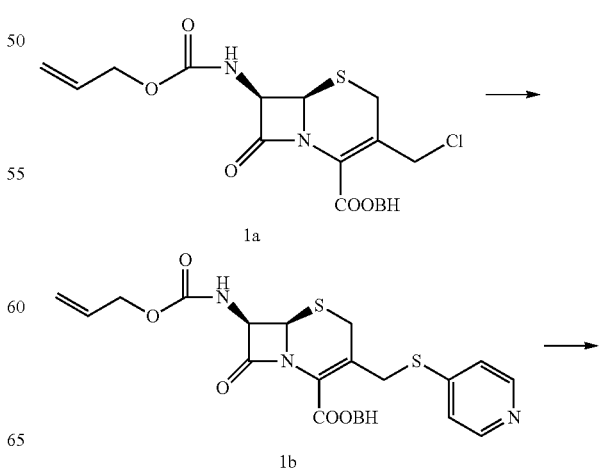

[Formula 86]

-continued

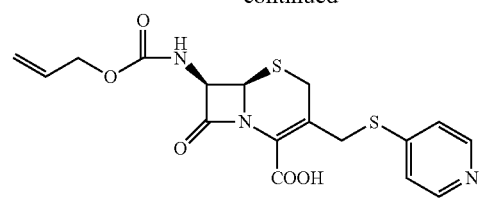
1c

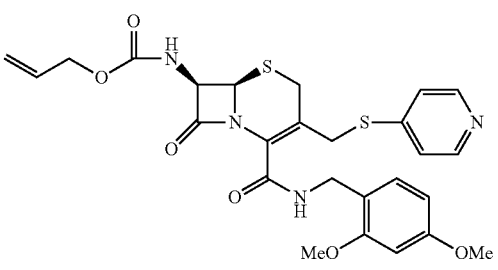
1d

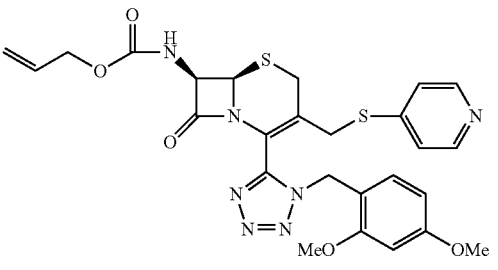
1e

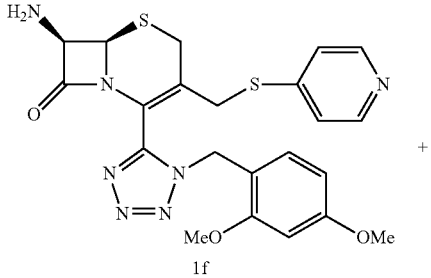
1f

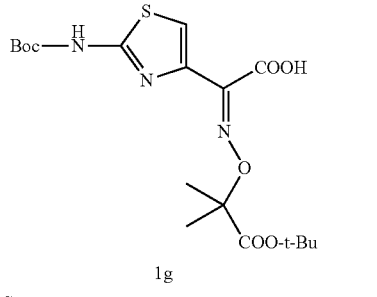
1g

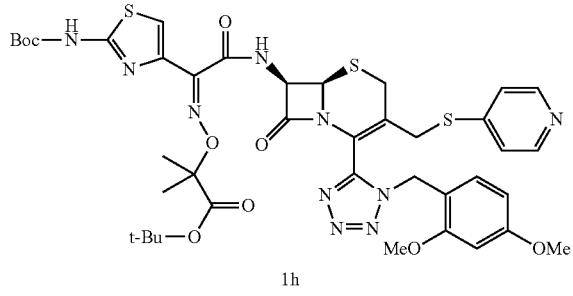
1h

Compound 1a→Compound 1b

To a solution of Compound 1a (39.92 g) in DMF (150 ml) were added successively mercaptopyridine (10.66 g), pyridine (8.32 ml) and NaBr (16.5 g). The mixture was stirred at room temperature for 40 minutes, and then added to a cold aqueous sodium chloride solution (500 ml). The obtained precipitates were collected by filtration, and washed with water. The resultant was dissolved in methylene chloride, washed with water and concentrated to give the desired Compound 1b (41.7 g).

$^1$H-NMR (CDCl$_3$) δ: 3.47, 3.61 (2H, AB-q, J=18.2 Hz), 3.99, 4.19 (2H, AB-q J=13.2 Hz), 4.62 (2H, d, J=5.1 Hz), 4.97 (1H, d, J=5.1 Hz), 5.25-5.36 (3H, m), 5.67 (1H, dd, J=4.5, 9.6 Hz), 5.85-5.95 (1H, m), 6.97-7.00 (3H, m), 7.25-7.43 (10H, m), 8.02-8.31 (2H, m)

MS (ESI): 560.2$^+$ (M+H)$^+$

Compound 1b→Compound 1c

To a solution of Compound 1b (47 g) in methylene chloride (200 ml) were added successively anisole (17.4 ml) and TFA (40 ml), and the mixture was reacted at room temperature for 2 hours. The mixture was concentrated under reduced pressure, and thereto was added isopropyl ether (500 ml) for pulverization. The resultant was collected by filtration, and recrystallized from methylene chloride/ethanol to give Compound 1c (30.57 g).

$^1$H-NMR (d$_6$-DMSO) δ: 3.52, 3.72 (2H, AB-q, J=18.0 Hz), 4.29, 4.34 (2H, AB-q, J=12.9 Hz), 4.52 (2H, d, J=5.1 Hz), 5.11 (2H, d, J=6.6 Hz), 8.40 (1H, d, J=8.4 Hz), 8.56 (2H, d, J=6.6),

MS (ESI): 408.2$^+$ (M+H)$^+$

Compound 1c→Compound 1d

To a suspension of Compound 1c (15 g) in methylene chloride (300 ml) were added pyridine (2.76 ml) at room temperature, then added thereto dimethoxybenzylamine (6.15 g) to give a solution. WSCD (9.53 g) was added thereto, and the mixture was stirred for 40 minutes. The resultant was concentrated under reduced pressure to give crystals. The obtained crystals were cooled to −20° C., and the precipitated crystals were collected by filtration, and washed with ether to give crystals of Compound 1d (12.3 g).

$^1$H-NMR (d$_6$-DMSO) δ: 3.47, 3.56 (2H, AB-q, J=16.8 Hz), 3.73 (3H, s), 4.17, 4.43 (2H, AB-q, J=12.9 Hz), 2.48 (2H, d, J=5.7 Hz), 4.53 (2H, d, J=5.4 Hz), 4.99 (1H, d, J=4.5 Hz), 5.18-5.37 (3H, m), 5.87-5.96 (1H, m), 6.42 (1H, dd, J=2.7, 8.7 Hz), 6.53 (1H, d, J=2.1 Hz), 7.18 (1H, d, J=8.1 Hz), 7.26-7.29 (2H, m), 8.29-8.31 (2H, m), 8.40 (1H, d, J=9.3 Hz), 8.61 (1H, bs)

MS (ESI): 557.4$^+$ (M+H)$^+$

Compound 1d→Compound 1e

To a suspension of Compound 1d (557 mg) in methylene chloride (15 ml) was added pyridine (264 µl) under ice-cooling, and then added thereto PCl$_5$ (208 mg). The mixture was stirred at room temperature for one hour, and further thereto was added pyridine (240 al), and then added MeOH (122 µl), and the mixture was further stirred at room temperature for 15 minutes. To the mixture was added trimethylsilyl azide (398 µl), and the mixture was reacted at room temperature for 15 hours, washed with water and purified by silica gel chromatography to give Compound 1e (220 mg).

$^1$H-NMR (CDCl$_3$) δ: 3.39, 3.59 (2H, AB-q, J=18.0 Hz), 3.76 (3H, s), 3.81 (3H, s), 4.61 (2H, d, J=5.7 Hz), 4.86 (1H, d, J=4.8 Hz), 5.23-5.62 (5H, m), 5.85-5.95 (1H, m), 6.43 (2H, d,

J=1.2 Hz), 6.94-7.05 (2H, m), 7.04 (1H, d, J=8.7 Hz), 8.33-8.38 (2H, m)

MS (ESI): 582.4$^+$ (M+H)$^+$

Compound 1e→Compound 1f

To a solution of Compound 1e (1.20 g) in methylene chloride (24 ml) was added dimedone (866 mg), and further thereto were added Ph$_3$P (100 mg) and Pd(PPh$_3$)$_4$ (100 mg), and the mixture was reacted for 40 minutes. The mixture was washed successively with aqueous NaHCO$_3$ solution and water, and the residue was purified by silica gel chromatography to give Compound 1f (572 mg).

$^1$H-NMR (CDCl$_3$) δ: 3.26-3.39 (2H, m), 3.26-3.80 (2H, m), 3.74 (3H, s), 3.80 (3H, s), 4.65 (1H, d, J=4.8 Hz), 4.89 (1H, d, J=5.4 Hz), 5.49 (2H, s), 6.42-6.47 (2H, m), 6.97 (2H, dd, J=1.8, 4.8 Hz), 7.14 (1H, d, J=8.1 Hz), 8.36 (2H, dd, J=1.8, 4.8 Hz),

MS (ESI): 498.4$^+$ (M+H)$^+$

Compound 1f+Compound 1g→Compound 1h

To a solution of Compound 1f (500 mg) and Compound 1g (430 mg) in methylene chloride (10 ml) was added WSCD (0.25 g), and the mixture was stirred under ice-cooling for 20 minutes. The mixture was diluted with ethyl acetate and washed with an aqueous sodium chloride solution. The mixture was concentrated, and the residue was purified by silica gel chromatography to give Compound 1h (574 mg).

$^1$H-NMR (CDCl$_3$) δ: 1.39 (9H, s), 1.55 (9H, s), 1.58 (3H, s), 1.63 (3H, s), 3.33-4.80 (2H, m), 3.36, 3.57 (2H, AB-q, J=13.8 Hz), 3.75 (3H, s), 3.77 (3H, s), 4.92 (1H, d, J=4.2 Hz), 5.52 (2H, s), 5.90 (1H, dd, J=4.8, 8.7 Hz), 6.44-6.47 (2H, m), 6.99-7.01 (2H, m), 7.01 (1H, d, J=8.7 Hz), 7.26-7.31 (2H, m), 8.31-8.50 (3H, m)

MS (ESI): 909.5$^+$ (M+H)$^+$

Synthesis of Compounds I-1, I-2, I-3

[Formula 87]

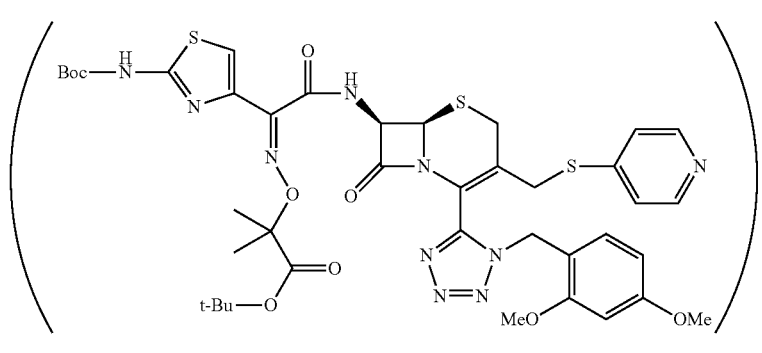

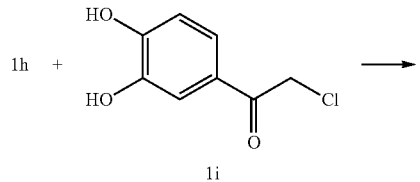

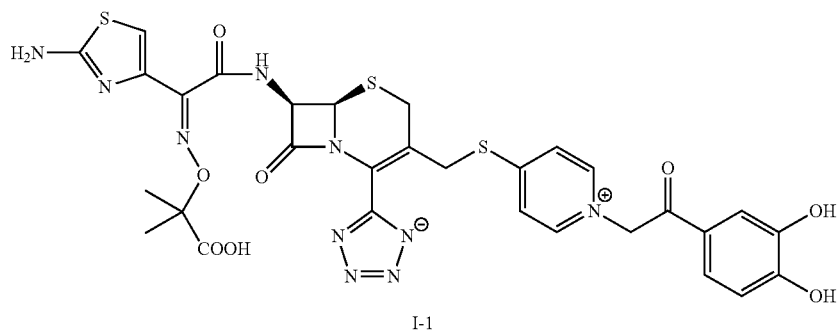

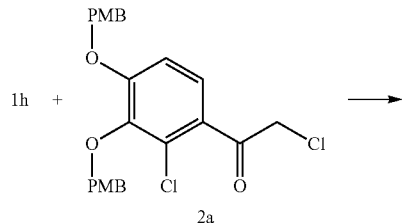

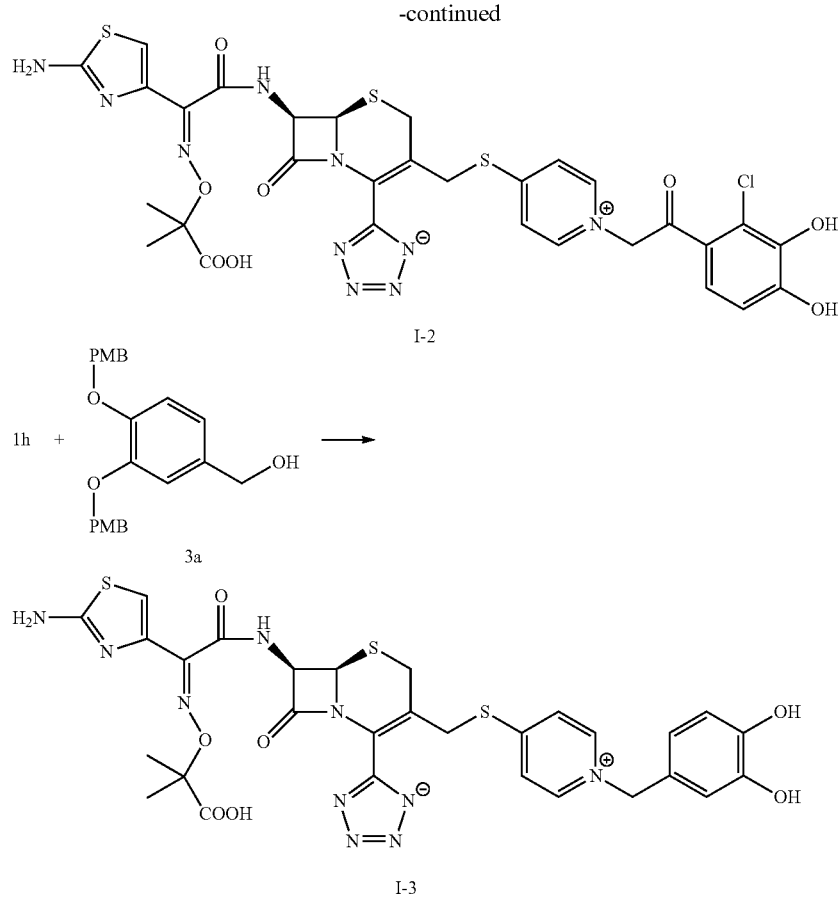

Example 1

Compound I-1

Compound 1h+Compound 1i→Compound I-1

To a solution of Compound 1i (200 mg)/DMF (1.5 ml) was added BSA (0.16 ml), and the mixture was stirred at room temperature for 10 minutes. To this solution were added Compound 1h (200 mg) and NaBr (90 mg), and the mixture was stirred at room temperature for 4 hours. To the mixture was added 2 mol/l hydrochloric acid (0.5 ml), and the mixture was stirred for 5 minutes. The mixture was poured into aqueous sodium chloride solution, and the resulting precipitates were collected by filtration, dissolved in methylene chloride, washed with water, dried and concentrated. The residue was dissolved in methylene chloride (5 ml), and thereto were added anisole (0.25 ml) and TFA (2 ml), and the mixture was stirred at room temperature for 1.5 hour. The resultant was treated in a conventional manner, and purified by HP-20 chromatography, and lyophilized to give Compound I-1 (92 mg).

$^1$H-NMR (d$_6$-DMSO) δ: 1.43 (3H, s), 1.46 (3H, s), 3.55, 3.73 (2H, AB-q, J=17.4 Hz), 4.34, 4.68 (2H, AB-q, J=13.8 Hz), 5.31 (1H, d, J=5.1 Hz), 5.64 (1H, dd, J=4.5, 8.1 Hz), 6.07 (2H, bs), 6.74 (1H, s), 6.83 (1H, d, J=8.1 Hz), 7.28 (2H, bs), 7.37-7.42 (2H, m), 7.79 (2H, d, J=6.6 Hz), 8.49 (2H, d, J=6.9 Hz)

MS (ESI): 753.3$^+$ (M+H)$^+$

IR (KBr) cm$^{-1}$: 3124, 1770, 1671, 1630

Example 2

Compound I-2

Compound 1h+Compound 2a→Compound I-2

To a solution of Compound 1h (250 mg) in DMF (2 ml) were added Compound 2a (165 mg) and NaBr (110 mg), and the mixture was stirred at room temperature for 2 hours, and then stirred at 8° C. for 15 hours. The mixture was poured into an aqueous sodium chloride solution, and the resulting precipitates were collected by filtration, dissolved in methylene chloride, washed with water, and concentrated to give a residue (0.40 g). The obtained residue was dissolved in methylene chloride (5 ml), and thereto was added anisole (0.65 ml), and further added TFA (4 ml), and the mixture was stirred at room temperature for 1.5 hour. The resultant was treated in a conventional manner, purified by HP-20 column chromatography, and lyophilized to give Compound I-2 (99 mg).

$^1$H-NMR (d$_6$-DMSO) δ: 1.20 (3H, s), 1.34 (3H, s), 3.33, 3.52 (2H, AB-q, J=16.5 Hz), 4.16, 4.46 (2H, AB-q, J=12.9 Hz), 5.09 (1H, d, J=5.1 Hz), 5.52-5.56 (1H, m), 5.83 (2H, d, J=6.6 Hz), 6.92 (1H, s), 8.23 (2H, d, J=6.6 Hz), 9.36 (1H, bs)

MS (ESI): 787.3$^+$ (M+H)$^+$

IR (KBr) cm$^{-1}$: 321, 3123, 1770, 1670, 1630

Example 3

Compound I-3

Compound 1h+Compound 3a→Compound I-3

To a suspension of Compound 3a (380 mg)/methylene chloride (10 ml) was added triethylamine (154 μl). Under ice-cooling, methanesulfonyl chloride (84 μl) was added thereto, and the mixture was stirred under ice-cooling for 40 minutes, and further stirred at room temperature for 30 minutes. To this reaction solution were added a solution of Compound 1h (300 mg)/DMF (4 ml) and NaI (450 mg), and the mixture was stirred at room temperature for 2 hours, and then stirred at 40° C. for 2 hours. The mixture was poured into an aqueous sodium chloride solution, and the resulting precipitates were collected by filtration, dissolved in methylene chloride, washed with water, dried and concentrated. The residue was dissolved in methylene chloride (10 ml), and thereto were added anisole (0.8 ml) and TFA (6 ml), and the mixture was stirred at room temperature for 2 hours, and allowed to stand at 8° C. for 15 hours. The mixture was treated in a conventional manner, purified by HP-20 chromatography, and lyophilized to give I-3 (69 mg).

$^1$H-NMR (d$_6$-DMSO) δ: 1.26 (3H, s), 1.27 (3H, s), 3.30, 3.45 (2H, AB-q, J=17.4 Hz), 4.09, 4.37 (2H, AB-q, J=12.9 Hz), 4.99 (1H, d, J=4.8 Hz), 5.50 (1H, dd, J=4.8, 8.7 Hz), 6.50-6.60 (3H, m), 6.90 (2H, bs), 7.30 (1H, s), 7.54-7.42 (2H, d, J=6.9 Hz), 8.44 (2H, d, J=6.9 Hz), 9.09 (2H, d, J=9.3 Hz)

MS (ESI): 725.5$^+$ (M+H)$^+$

IR (KBr) cm$^{-1}$: 3117, 1767, 1672, 1625

Example 4

Compound I-4

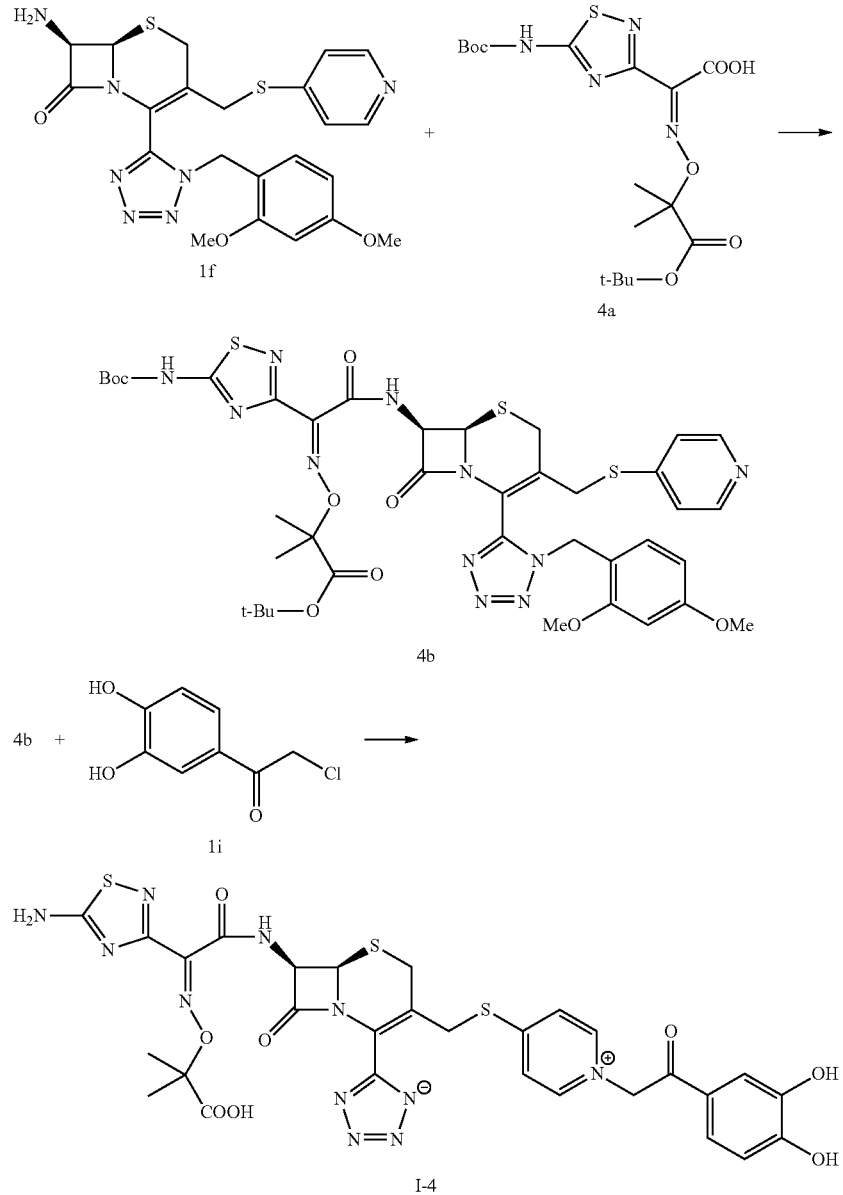

[Formula 88]

Compound 1f+Compound 4a→Compound 4b

To a solution of Compound 1f (303 mg) and Compound 4a (290 mg) in methylene chloride (5 ml) was added WSCD (0.14 g), and the mixture was stirred under ice-cooling for 30 minutes. The mixture was diluted with ethyl acetate, and washed with an aqueous sodium chloride solution. The mixture was concentrated, and the residue was purified by silica gel chromatography to give Compound 4b (602 mg).

$^1$H-NMR (CDCl$_3$) δ: 1.40-1.68 (24H, m), 3.38, 3.58 (2H, AB-q, J=18.6 Hz), 3.70-3.81 (2H, m), 3.81 (3H, s), 3.742 (31H, s), 4.95 (2H, d, J=5.1 Hz), 5.51 (2H, s), 5.99 (1H, dd, J=5.1, 9.0 Hz), 6.44-6.47 (2H, m), 7.00-7.07 (3H, m), 8.40-8.42 (2H, m)

MS (ESI): 910.4$^+$ (M+H)$^+$

Compound 4b+Compound 1i→Compound I-4

To a solution of Compound 1i (137 mg)/DMF (2 ml) was added BSA (0.33 ml), and the mixture was stirred at room temperature for 15 minutes. To this solution was added a solution of 4b (602 mg)/NaBr (251 mg)/DMF (3 ml), and the mixture was stirred at room temperature for 2.5 hours, and then stirred at 40° C. for 1.5 hour. The mixture was poured into an aqueous sodium chloride solution containing 2 mol/l hydrochloric acid (2 ml), and the resulting precipitates were collected by filtration, dissolved in methylene chloride, washed with water, dried and concentrated. The residue (0.79 g) was dissolved in methylene chloride (20 ml), and thereto was added anisole (0.54 ml) at −20° C., then further thereto was added 2M AlCl$_3$/MeNO$_2$ solution, and the mixture was stirred at a temperature of from −20° C. to 0° C. for 40 minutes. The mixture was treated in a conventional manner, purified by HP-20 chromatography, and lyophilized to give Compound I-4 (150 mg).

$^1$H-NMR (d$_6$-DMSO) δ: 1.44 (3H, s), 1.46 (3H, s), 3.53, 3.72 (2H, AB-q, J=18.0 Hz), 4.31, 4.65 (2H, AB-q, J=13.5 Hz), 5.28 (1H, d, J=4.2 Hz), 5.75 (1H, dd, J=4.2, 8.7 Hz), 6.06 (2H, bs), 6.90 (1H, d, J=8.1 Hz), 7.36-7.41 (3H, m), 7.78 (2H, d, J=6.9 Hz), 8.18 (2H, bs), 8.48 (2H, d, J=6.9 Hz)

MS (ESI): 754.2$^+$ (M+H)$^+$

Example 5

Compound I-5

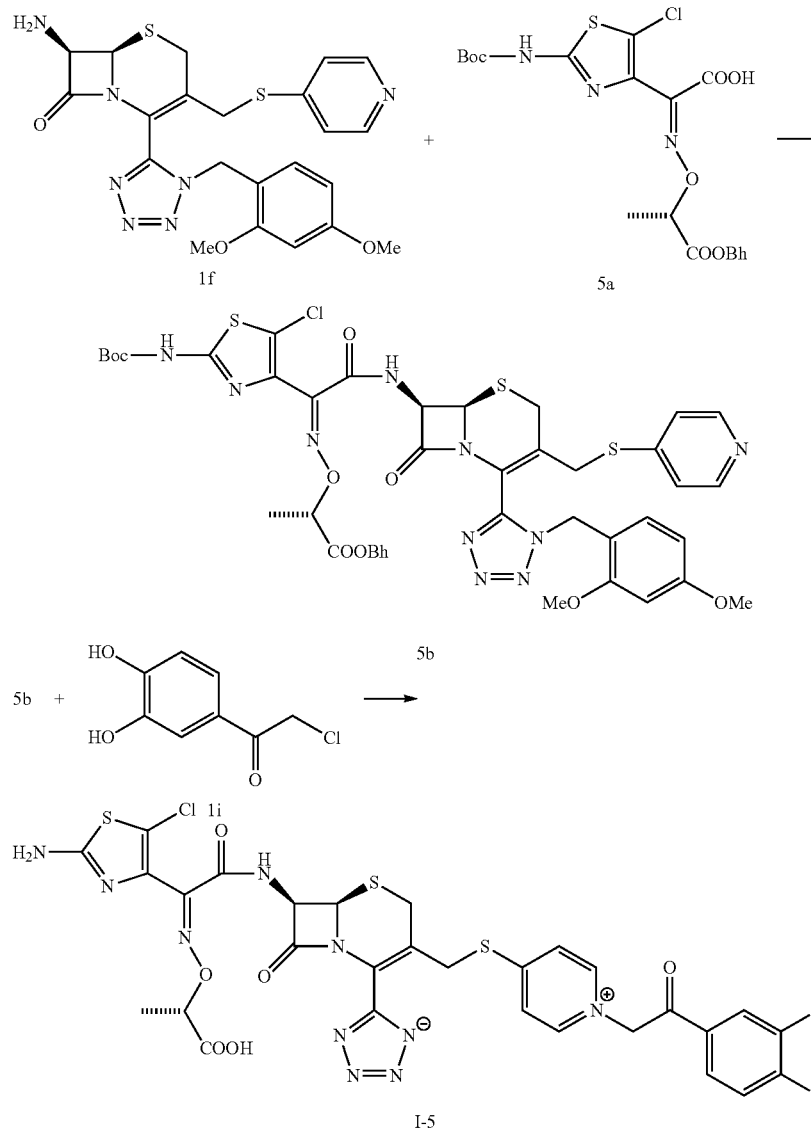

[Formula 89]

Compound 1f+Compound 5a→Compound 5b

To a solution of Compound 1f (250 mg) and Compound 5a (280 mg) in methylene chloride (6 ml) was added WSCD (0.12 g), and the mixture was stirred under ice-cooling for 30 minutes. The mixture was diluted with ethyl acetate, washed with an aqueous sodium chloride solution and concentrated. The residue was purified by silica gel chromato to give Compound 5b (348 mg).

$^1$H-NMR (CDCl$_3$) δ: 1.52 (9H, s), 1.57 (9H, s), 1.62 (3H, d, J=7.2 Hz), 3.22, 3.52 (2H, AB-q, J=18.0 Hz), 3.67-3.82 (2H, m), 3.81 (3H, s), 3.77 (3H, s), 4.90 (1H, d, J=5.1 Hz), 5.33, 5.42 (2H, AB-q, J=15 Hz), 6.39-6.47 (2H, m), 6.87 (1H, s), 6.91-7.31 (14H, m), 8.08 (1H, d, J=8.7 Hz), 8.27 (1H, bs), 8.35-8.39 (2H, m)

Compound 5b+Compound 1i→Compound I-5

To a solution of Compound 1i (76 mg)/DMF (2 ml) was added BSA (60 ul), and the mixture was stirred at room temperature for 15 minutes. To the mixture was further added a solution of Compound 5b (348 mg)/DMF (1 ml) and NaBr (100 mg), and the mixture was allowed to stand at room temperature for 2.5 hours, and then at 8° C. for 15 hours. The mixture was poured into an aqueous sodium chloride solution containing 2 mol/l hydrochloric acid (2 ml), and the resulting precipitates were collected by filtration, dissolved in methylene chloride, washed with water, dried and concentrated. The residue (0.41 g) was dissolved in methylene chloride (5 ml), and thereto was added anisole (0.45 ml), and then added TFA (5 ml), and the mixture was reacted at room temperature for 1.5 hour. The resultant was treated in a conventional manner, purified by HP-20 chromatography, and lyophilized to give Compound I-5 (139 mg).

$^1$H-NMR (d$_6$-DMSO) δ: 1.42 (3H, d, J=6.9 Hz), 13.54, 3.67 (2H, AB-q, J=17.4 Hz), 4.33, 4.59 (2H, AB-q, J=13.2 Hz), 4.60 (1H, q, J=6.9 Hz), 5.29 (1H, d, J=4.8 Hz), 5.76 (1H, dd, J=4.8, 8.7 Hz), 6.07 (2H, bs), 6.97 (1H, d, J=8.1 Hz), 7.38-7.47 (4H, m), 7.79 (2H, d, J=6.6 Hz), 8.50 (2H, d, J=6.6 Hz)

MS (ESI): 773.2$^+$ (M+H)$^+$

Example 6

Compound I-6

[Formula 90]

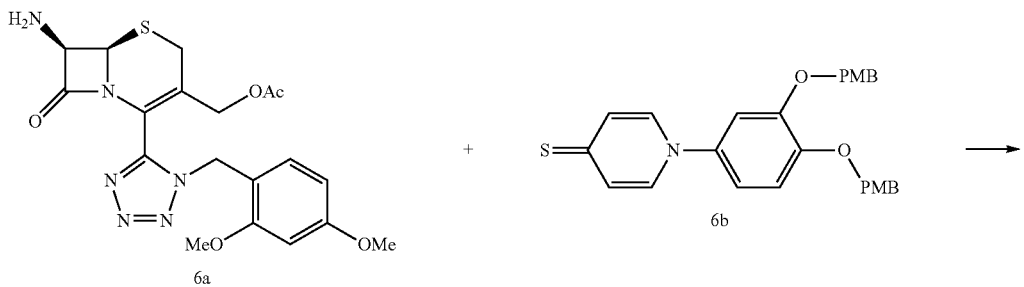

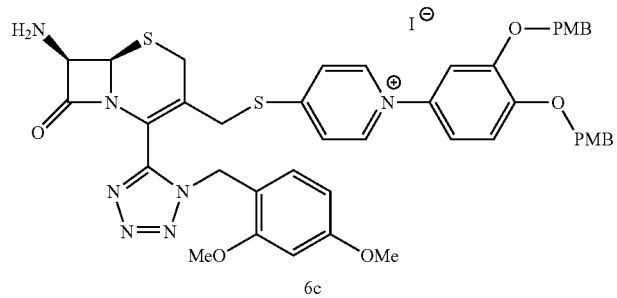

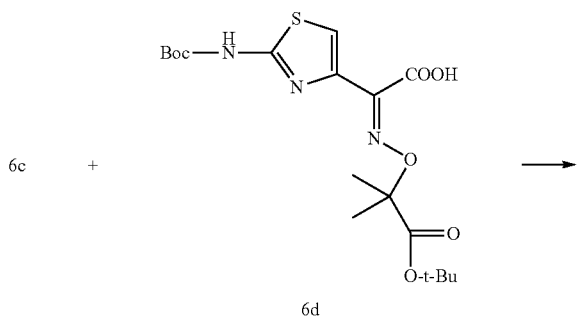

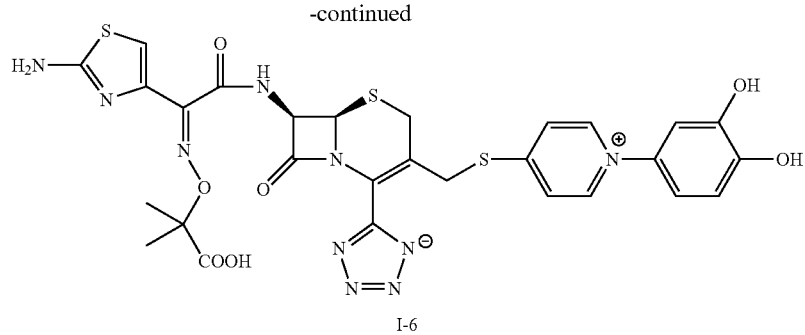

I-6

Compound 6a+Compound 6b→Compound 6c

To a solution of Compound 6a (766 mg)/methylene chloride (6 ml) was added MSTFA (N-methyl-N-trimethylsilyl-trifluoroacetamide) (737 al), and the mixture was stirred at room temperature for 15 minutes, cooled to −20° C., and thereto was added Me$_3$Si—I (0.34 ml). The mixture was stirred at room temperature for 1.5 hour, and thereto was added a solution of Compound 6b (0.67 g)/DMF (5 ml). Methylene chloride was removed by evaporation under reduced pressure, and the resultant was stirred at room temperature for 30 minutes, and poured into an aqueous sodium chloride solution. The resulting precipitates were collected by filtration, dissolved in methylene chloride, washed with water and concentrated to give a crude Compound 6c (1.37 g).

MS (ESI): 816.4$^+$ (M+H)$^+$

Compound 6c+Compound 6d→Compound I-6

To a solution of crude Compound 6c (1.37 g)/methylene chloride (25 ml) was added Compound 6d (0.73 g), and further thereto was added under ice-cooling WSCD (0.41 g), and the mixture was stirred for 20 minutes. The mixture was diluted with ethyl acetate and washed with water. The resulant was concentrated, and the obtained residue was dissolved in methylene chloride (30 ml), and anisole (2 ml) was added thereto. The mixture was cooled to −20° C., and 2M-AlCl$_3$/MeNO$_2$ solution (10 ml) was added thereto. The mixture was stirred under ice-cooling for 40 minutes. The resultant was treated in a conventional manner, purified by HP-20 chromatography, and lyophilized to give Compound I-6 (59 mg).

$^1$H-NMR (d$_6$-DMSO) δ: 1.26 (3H, s), 1.27 (3H, s), 3.30, 3.45 (2H, AB-q, J=17.4 Hz), 4.09, 4.37 (2H, AB-q, J=12.9 Hz), 4.99 (1H, d, J=4.8 Hz), 5.50 (1H, dd, J=4.8, 8.7 Hz), 6.50-6.60 (3H, m), 6.90 (2H, bs), 7.30 (1H, s), 7.54-7.42 (2H, d, J=6.9 Hz), 8.44 (2H, d, J=6.9 Hz), 9.09 (2H, d, J=9.3 Hz)

MS (ESI): 725.5$^+$ (M+H)$^+$

IR (KBr) cm$^{-1}$: 3117, 1769, 1622

Example 7

Compound I-7

[Formula 91]

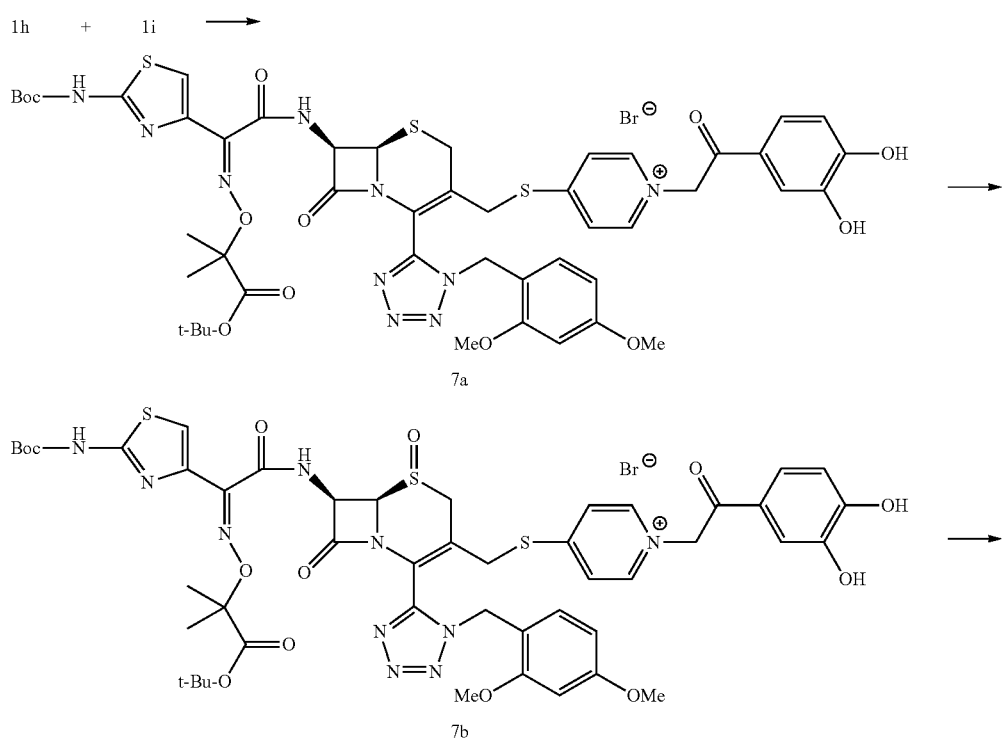

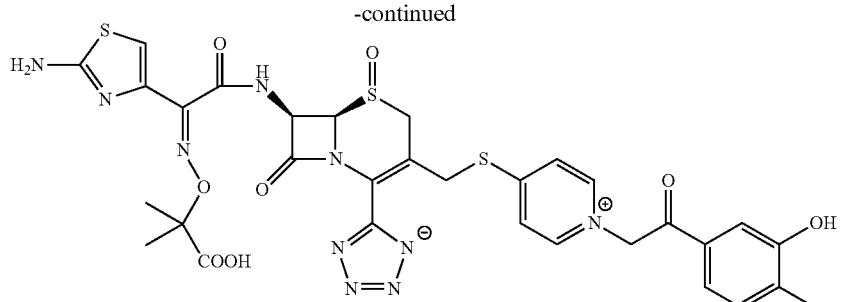

I-7

Compound 1h+Compound 1i→Compound 7a

To a solution of Compound 1i (102 mg) in DMF (2 ml) was added BSA (245 μl), and the mixture was stirred at room temperature for 10 minutes. To the mixture were added Compound 1i (383 mg) and NaBr (173 mg), and the mixture was stirred at room temperature for 3 hours, poured into an aqueous sodium chloride solution containing diluted hydrochloric acid. The resulting precipitates were collected by filtration, dissolved in methylene chloride, washed with water, and concentrated to give crude Compound 7a (437 mg).

Compound 7a→Compound 7b

To a solution of Compound 7a (437 mg) in methylene chloride (10 ml) was added BSA (245 al) under ice-cooling, and 10 minutes thereafter, 70% MCPBA (150 mg) was added thereto, and the mixture was stirred for 20 minutes. The mixture was washed with an aqueous NaHCO$_3$ solution and concentrated to give Compound 7b (0.46 g).

Compound 7b→Compound I-7

Compound 7b (0.46 g) was dissolved in methylene chloride (5 ml), and thereto were added at room temperature anisole (0.5 ml) and TFA (4 ml), and the mixture was stirred for 1.5 hour. The mixture was treated in a conventional manner, purified by HP-20 column chromatography, and lyophilized to give Compound I-7 (53 mg).

$^1$H-NMR (d$_6$-DMSO) δ: 1.42 (3H, s), 1.46 (3H, s), 3.45, 3.93 (2H, AB-q, J=18.3 Hz), 4.26, 4.93 (2H, AB-q, J=13.2 Hz), 5.12 (1H, bs), 5.94 (1H, bs), 6.05 (2H, bs), 6.78 (1H, s), 6.89 (1H, d, J=8.4 Hz), 7.20-7.45 (4H, m), 7.69 (2H, d, J=6.0 Hz), 8.459 (2H, bs) MS (ESI): 769.2$^+$ (M+H)$^+$

Example 8

Compound I-8

[Formula 92]

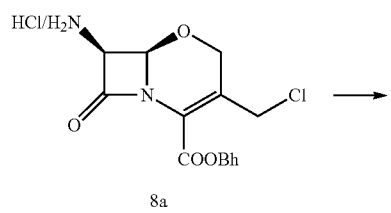

8a

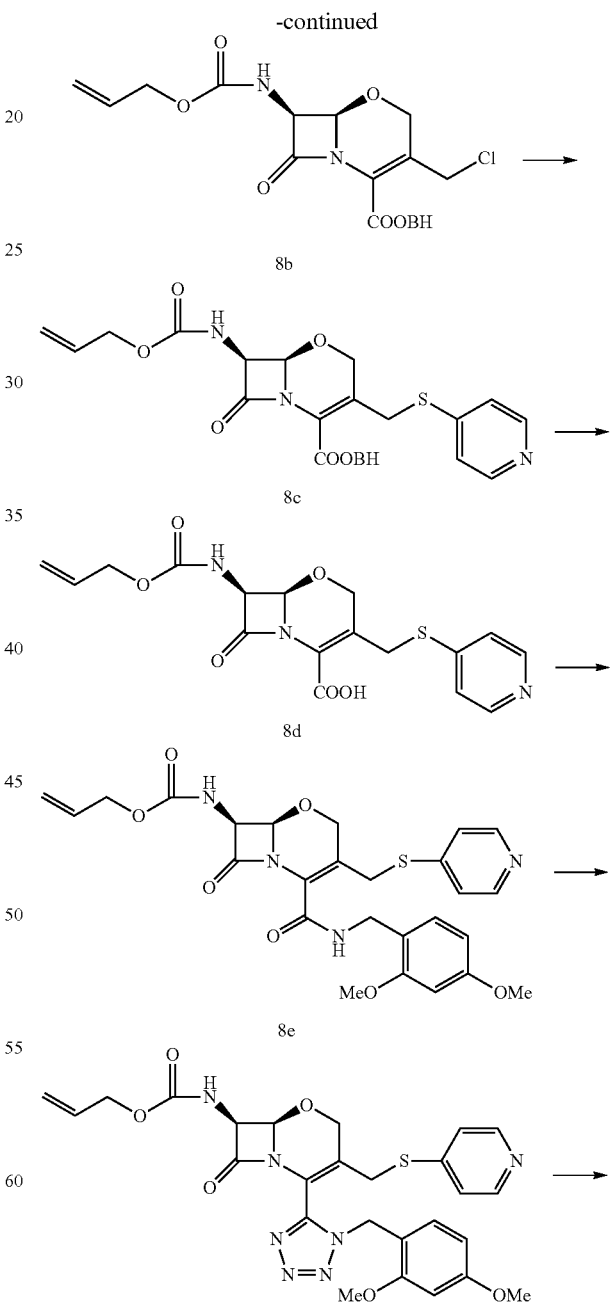

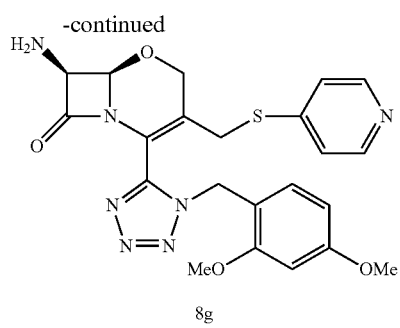

8g

Compound 8a→Compound 8b

A suspension of Compound 8a (7.23 g) in methylene chloride (100 ml) was cooled to −30° C., and thereto was added pyridine (2.92 ml), and further thereto was added allyl chloroformate (2.11 ml). The mixture was stirred at a temperature of from −30° C. to 0° C. for 30 minutes, and washed successively with diluted hydrochloric acid and water, and concentrated under reduced pressure to give Compound 8b (7.53 g).

$^1$H-NMR (CDCl$_3$) δ: 4.46-4.68 (6H, m), 5.09 (1H, d, J=3.6 Hz), 5.23-5.57 (3H, m), 5.82-5.88 (1H, m), 6.93 (1H, s), 7.23-7.52 (10H, m)

Compound 8b→Compound 8c

To a solution of Compound 8b (7.53 g) in DMF (35 ml) were added successively 4-mercaptopyridine (2.3 g), pyridine (1.73 ml), and NaBr (3.42 g). The mixture was stirred at room temperature for 1.5 hour, and poured into water. The resulting precipitates were dissolved in methylene chloride, washed with water, and concentrated to give Compound 8c (8.69 g).

$^1$H-NMR (CDCl$_3$) δ: 4.07, 4.33 (2H, AB-q, J=13.5 Hz), 4.47, 4.56 (2H, AB-q, J=18.0 Hz), 4.61 (2H, d, J=6.6 Hz), 5.03 (1H, d, J=1.5 Hz), 5.21-5.30 (2H, m), 5.48 (1H, s), 5.83-5.95 (1H, m), 6.94 (1H, s), 7.03 (2H, dd, J=1.8, 4.8 Hz), 7.20-7.52 (10H, m), 8.31 (2H, dd, J=1.8, 4.8 Hz)

Compound 8c→Compound 8d

To a solution of Compound 8c (8.69 g)/methylene chloride (50 ml) were added anisole (3.5 ml) and CF$_3$COOH (10 ml), and the mixture was stirred at room temperature for 2 hours. The mixture was concentrated under reduced pressure, and thereto was added ethyl ether for pulverization. The resulting powder was collected by filtration, and recrystallized from methylene chloride/ethanol to give Compound 8d (6.08 g).

$^1$H-NMR (d$_6$-DMSO) δ: 4.26, 4.35 (2H, AB-q, J=12.6 Hz), 4.49 (2H, s), 5.12-5.32 (4H, m), 5.75-5.92 (1H, m), 7.70 (2H, d, J=5.1 Hz), 8.13 (1H, d, J=9.3 Hz), 8.56 (2H, d, J=5.1 Hz),

MS (ESI): 392.2$^+$ (M+H)$^+$

Compound 8d→Compound 8e

To a suspension of Compound 8d (5.13 g) in methylene chloride (50 ml) were added pyridine (0.85 ml) and 2,4-dimethoxybenzylamine (1.87 g). Then, WSCD (water-soluble carbodiimide) (3.26 g) was added thereto at 5° C., and the mixture was stirred for one hour. The mixture was washed with water, and concentrated to give Compound 8e (5.63 g).

$^1$H-NMR (CDCl$_3$) δ: 3.77-3.90 (8H, m), 4.30-4.60 (6H, m), 4.98 (1H, d, J=3.6 Hz), 5.00-5.55 (4H, m), 5.82-5.97 (1H, m), 6.41-6.47 (2H, m), 7.14-7.30 (3H, m), 7.82 (1H, bs), 8.31 (2H, d, J=5.7 Hz),

MS (ESI): 541.3$^+$ (M+H)$^+$

Compound 8e→Compound 8f

To a solution of Compound 8e (5.63 g)/methylene chloride (50 ml) were added pyridine (1.67 ml) and PCl$_5$ (2.6 g) under ice-cooling, and the mixture was stirred for one hour. Then, Me$_3$SiN$_3$ (8.3 ml), pyridine (5.0 ml) and methanol (2.11 ml) were added thereto, and the mixture was stirred at 40° C. for 2 hours. The mixture was washed with water twice, and concentrated under reduced pressure to give crude Compound 8f (5.87 g).

MS (ESI): 566.3$^+$ (M+H)$^+$

Compound 8f→Compound 8g

To a solution of Compound 8f (1.90 g) in methylene chloride (50 ml) were added dimedone (1.34 g), Ph$_3$P (120 mg), and (Ph$_3$P)$_4$Pd (120 mg) at room temperature. The mixture was stirred for 1.5 hour, and washed with aqueous NaHCO$_3$ solution twice, and concentrated to give crude Compound 8g (1.47 g).

MS (ESI): 482.3$^+$ (M+H)$^+$

Synthesis of Compound I-8

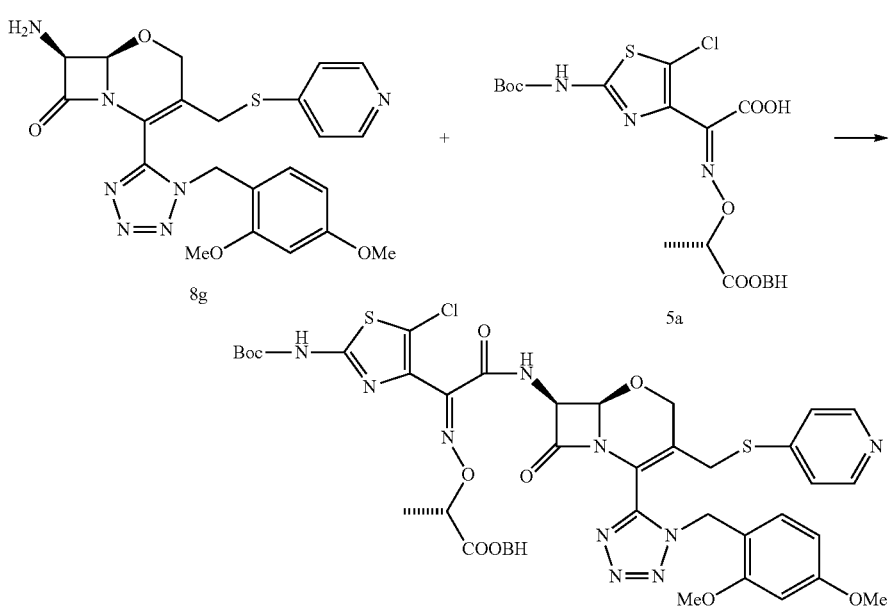

[Formula 93]

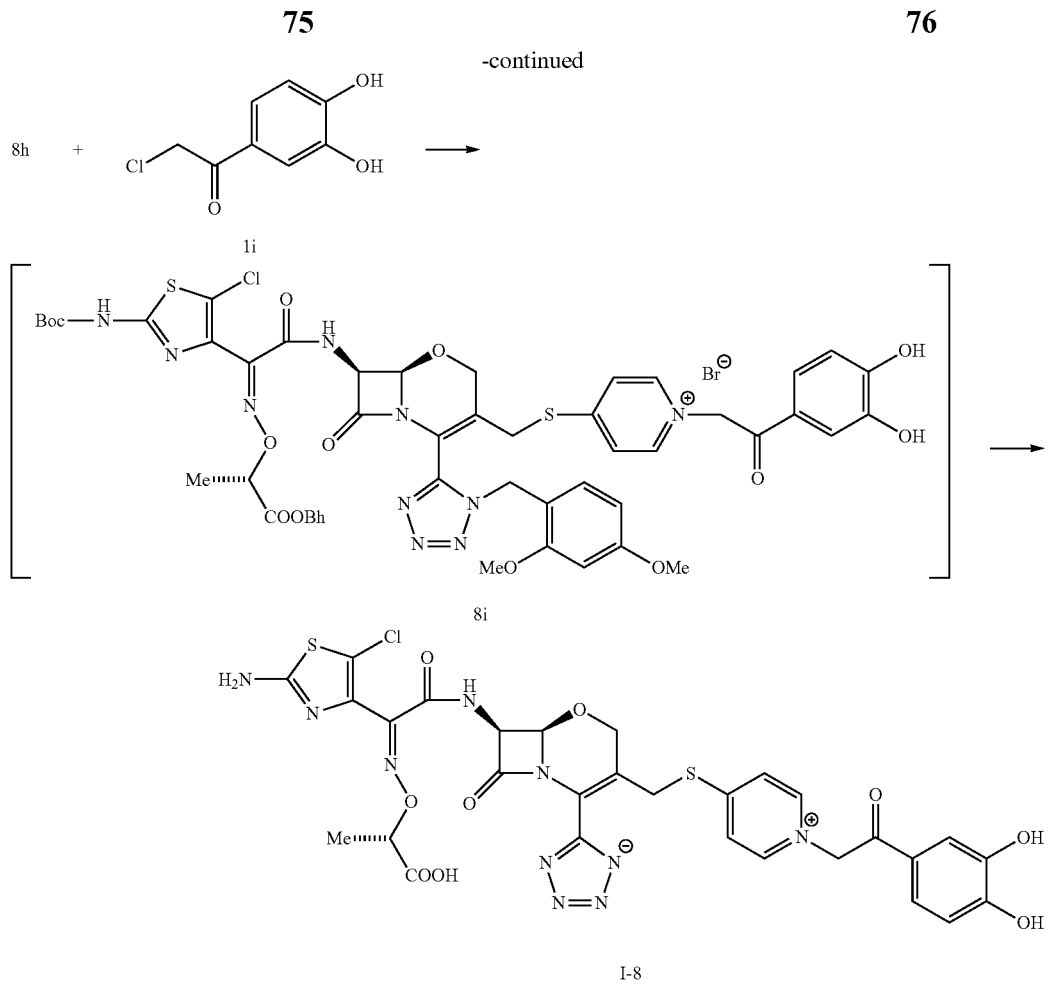

Compound 8g+Compound 5a→Compound 8h

Crude Compound 8g (3.2 g) and Compound 5a (3.36 g) were dissolved in methylene chloride (30 ml), and thereto was added WSCD (1.34 g) under ice-cooling, and the mixture was stirred for 30 minutes. The mixture was diluted with ethyl acetate, and washed with water. The residue was subjected to silica gel chromatography to give crude Compound 8h (1.58 g).

Compound 8h+Compound 1i→Compound I-8

Compound 1i (78 mg) was dissolved in DMF (1.5 ml), and thereto was added BSA (N,O-bis(trimethylsilyl)acetamide) (243 μl), and the mixture was stirred at room temperature for 10 minutes. Then, Compound 8h (288 mg) and NaBr (115 mg) were added thereto, and the mixture was stirred at room temperature for 1.5 hour, and poured into aqueous sodium chloride solution. The resulting precipitates were collected by filtration, dissolved in methylene chloride, washed with water and concentrated. The residual Compound 8i (whole amount) was dissolved in methylene chloride (5 ml), and anisole (0.35 ml) and TFA (2 ml) were added thereto, and the mixture was stirred for 1.5 hour. The mixture was concentrated, and ether was added thereto for pulverization. The obtained powder was collected by filtration, purified by HP-20 column chromatography, and lyophilized to give Compound I-8 (93 mg).

$^1$H-NMR (d$_6$-DMSO) δ: 1.38 (3H, t, J=7.2 Hz), 4.45-4.80 (5H, m), 5.32 (1H, d, J=3.6 Hz), 5.62 (1H, dd, J=3.8, 9.6 Hz), 6.08 (2H, bs), 6.90-6.95 (1H, m), 7.35-7.50 (4H, m), 7.94 (2H, d, J=6.6 Hz), 8.52 (2H, d, J=6.3 Hz)

MS (ESI): 757.2$^+$ (M+H)

Example 9

Synthesis of Compound I-9

[Formula 94]

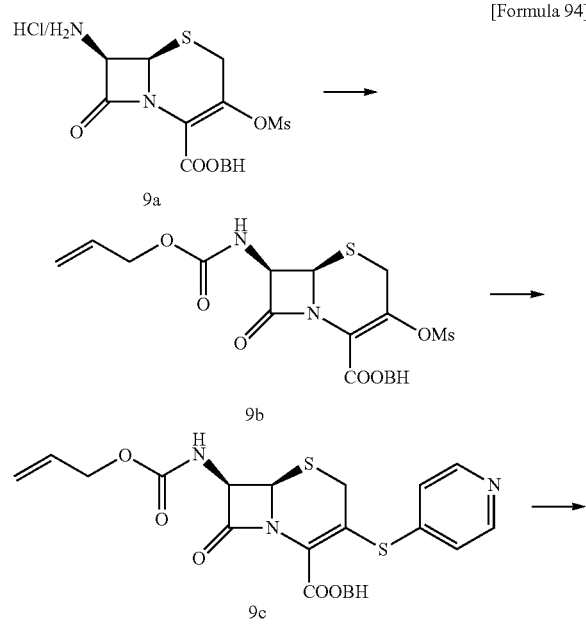

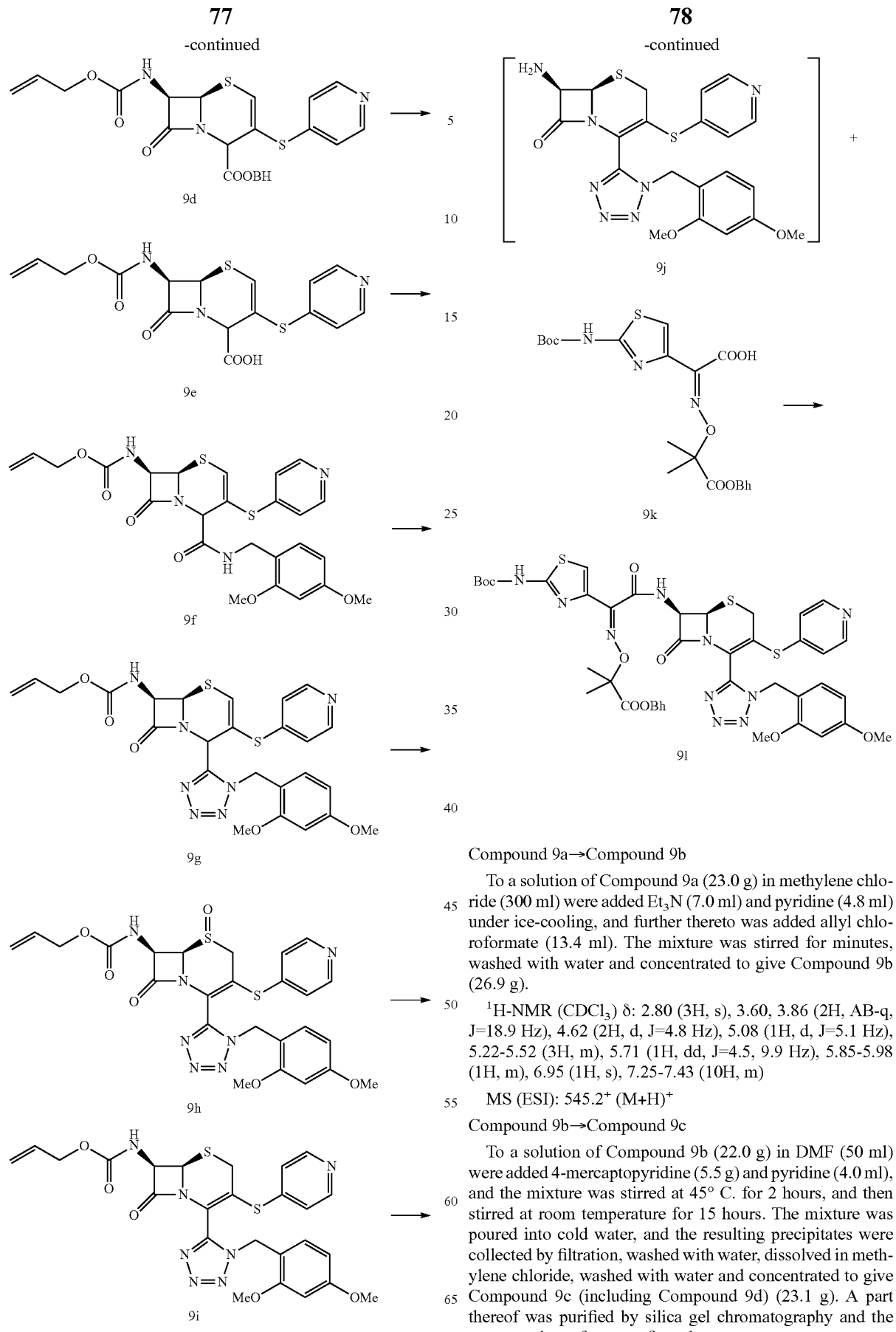

Compound 9a→Compound 9b

To a solution of Compound 9a (23.0 g) in methylene chloride (300 ml) were added Et₃N (7.0 ml) and pyridine (4.8 ml) under ice-cooling, and further thereto was added allyl chloroformate (13.4 ml). The mixture was stirred for minutes, washed with water and concentrated to give Compound 9b (26.9 g).

¹H-NMR (CDCl₃) δ: 2.80 (3H, s), 3.60, 3.86 (2H, AB-q, J=18.9 Hz), 4.62 (2H, d, J=4.8 Hz), 5.08 (1H, d, J=5.1 Hz), 5.22-5.52 (3H, m), 5.71 (1H, dd, J=4.5, 9.9 Hz), 5.85-5.98 (1H, m), 6.95 (1H, s), 7.25-7.43 (10H, m)

MS (ESI): 545.2⁺ (M+H)⁺

Compound 9b→Compound 9c

To a solution of Compound 9b (22.0 g) in DMF (50 ml) were added 4-mercaptopyridine (5.5 g) and pyridine (4.0 ml), and the mixture was stirred at 45° C. for 2 hours, and then stirred at room temperature for 15 hours. The mixture was poured into cold water, and the resulting precipitates were collected by filtration, washed with water, dissolved in methylene chloride, washed with water and concentrated to give Compound 9c (including Compound 9d) (23.1 g). A part thereof was purified by silica gel chromatography and the structure thereof was confirmed.

¹H-NMR (d₆-DMSO) δ: 3.26, 3.62 (2H, AB-q, J=18.0 Hz), 4.62 (2H, d, J=6.0 Hz), 5.11 (1H, d, J=5.4 Hz), 5.23-5.36 (3H, m), 5.76 (1H, dd, J=4.8, 9.3 Hz), 5.82-5.98 (1H, m), 6.21 (1H, d, J=9.9 Hz), 7.00 (1H, s), 7.06 (2H, dd, J=1.2, 4.1 Hz), 7.10-7.35 (10H, m), 8.42 (2H, dd, J=1.2, 4.2 Hz)

MS (ESI): 560.2⁺ (M+H)⁺

Compound 9c→Compound 9d

To a solution of 9c (partially containing Compound 9d) (11.5 g) in methylene chloride (220 ml) was added Et₃N (2.0 ml), and the mixture was stirred for 1.5 hour. The mixture was concentrated under reduced pressure to give 9d (containing 18% of Compound 9c, confirmed by HPLC) (11.6 g), which was used in the subsequent reaction without any further purification and isolation.

MS (ESI): 560.2⁺ (M+H)⁺

Compound 9d→Compound 9e

To a solution of Compound 9d (11.2 g) in methylene chloride (200 ml) were added anisole (11 ml) and TFA (35 ml), and the mixture was stirred at room temperature for 1.5 hour. The mixture was concentrated under reduced pressure, and thereto was added ether for pulverization. The resultant powders were collected by filtration to give Compound 9e (7.89 g).

¹H-NMR (CDCl₃) δ: 4.33 (2H, d, J=5.1 Hz), 4.57 (1H, s), 4.90-5.14 (4H, m), 5.60-5.76 (1H, m), 4.27-7.33 (2H, m), 8.32-8.37 (2H, m)

MS (ESI): 394.2⁺ (M+H)⁺

Compound 9e→Compound 9f

To a solution of Compound 9e (1.01 g) in methylene chloride (10 ml) were added pyridine (0.16 ml) and dimethoxybenzylamine (344 mg), and WSCD (0.48 g) was added thereto under ice-cooling, and the mixture was stirred for 30 minutes. The mixture was diluted with ethyl acetate, washed with water, and the residue was purified by silica gel chromatography to give Compound 9f (0.51 g).

¹H-NMR (CDCl₃) δ: 3.74 (3H, s), 3.80 (3H, s), 4.24 (2H, d, J=5.4 Hz), 4.63 (2H, d, J=5.7 Hz), 4.72 (1H, s), 5.24-5.37 (3H, m), 5.50-5.53 (2H, m), 5.83-6.02 (2H, m), 6.39 (2H, bs), 6.91 (2H, dd, J=1.8, 5.1 Hz), 6.95-7.08 (3H, m), 8.27 (2H, d, J=6.3 Hz)

MS (ESI): 543.2⁺ (M+H)⁺

Compound 9f→Compound 9g

To a solution of Compound 9f (3.40 g) in methylene chloride (50 ml) were added pyridine (1.0 ml) and PCl₅ (1.57 g) under ice-cooling. The mixture was stirred under ice-cooling for 15 minutes, and then stirred at room temperature for 1.5 hour. The mixture was cooled to −30° C., and pyridine (2.41 ml) and methanol (0.91 ml) were added thereto. The mixture was stirred for 20 minutes, and then, Me₃SiN₃ (3.32 ml) and methanol (1.02 ml) were added thereto. The mixture was warmed to room temperature, and stirred for 2.5 hours, and washed with water. The resultant was concentrated, and the residue was purified by silica gel chromatography to give Compound 9g (2.32 g).

¹H-NMR (CDCl₃) δ: 3.60 (3H, s), 3.76 (3H, s), 4.65 (2H, d, J=5.4 Hz), 5.24-5.52 (5H, m), 5.87 (1H, d, J=1.5 Hz), 5.86-6.00 (1H, m), 6.27 (1H, d, J=2.7 Hz), 6.37 (1H, dd, J=2.4, 11.1 Hz), 6.96 (2H, dd, J=1.8, 4.2 Hz), 7.10-7.15 (2H, m), 8.45 (2H, dd, J=1.5, 4.5 Hz)

MS (ESI): 568.3⁺ (M+H)⁺

Compound 9g→Compound 9h

Compound 9g (470 mg) was dissolved in methylene chloride (20 ml), and thereto was added gradually MCPBA (m-chloroperbenzoic acid) (0.36 g) under ice-cooling, and the mixture was washed with Na₂S₂O₃/aqueous NaHCO₃ solution. The mixture was concentrated and the obtained residue was purified by silica gel chromatography to give Compound 9h (266 mg).

MS (ESI): 584.3⁺ (M+H)⁺

Compound 9h→Compound 9i

To a solution of Compound 9h (320 mg) in methylene chloride (10 ml) was added PBr₃ (0.40 ml) at −30° C. The mixture was stirred at −20° C. for 2 hours, and washed with aqueous NaHCO₃ solution. The mixture was concentrated and the residue was purified by silica gel chromatography to give Compound 9i (222 mg).

¹H-NMR (CDCl₃) δ: 3.36, 3.60 (2H, AB-q, J=18.0 Hz), 3.75 (3H, s), 3.83 (3H, s), 4.62 (2H, d, J=6.0 Hz), 4.98 (1H, d, J=5.1 Hz), 5.22-5.60 (4H, m), 5.80-6.00 (2H, m), 8.08 (1H, d, J=6.0 Hz), 8.42 (2H, d, J=5.1 Hz), 8.78 (1H, d, J=6.0 Hz)

MS (ESI): 568.3⁺ (M+H)⁺

Compound 9i→Compound 9j

Compound 9i (220 mg) was dissolved in methylene chloride (5 ml), and thereto were added dimedone (163 mg), Ph₃P (20 mg), and Pd(PPh₃)₄ (20 mg) at room temperature, and the mixture was stirred for 2 hours. The mixture was washed with aqueous NaHCO₃ solution twice, and concentrated to give Compound 9j (205 mg).

MS (ESI): 484.2⁺ (M+H)

Compound 9j→Compound 9k

Compound 9j (205 mg) and Compound 9k (221 mg) were dissolved in methylene chloride (5 ml), and thereto was added WSCD (97 mg) under ice-cooling, and the mixture was stirred for one hour. The mixture was diluted with ethyl acetate, washed with water, concentrated, and the obtained residue was subjected to silica gel chromatography to give Compound 9l (245 mg).

MS (ESI): 1005.8⁺ (M+H)⁺

Synthesis of Compound I-9

[Formula 95]

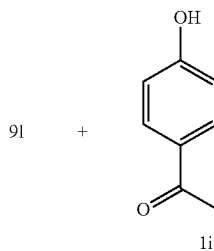

-continued

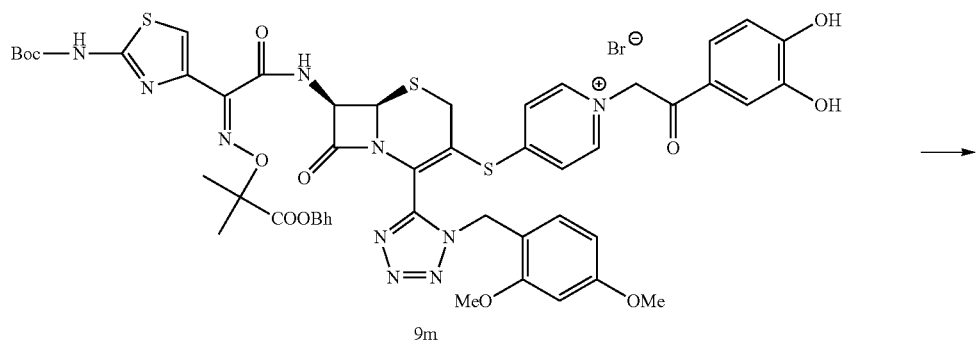
9m

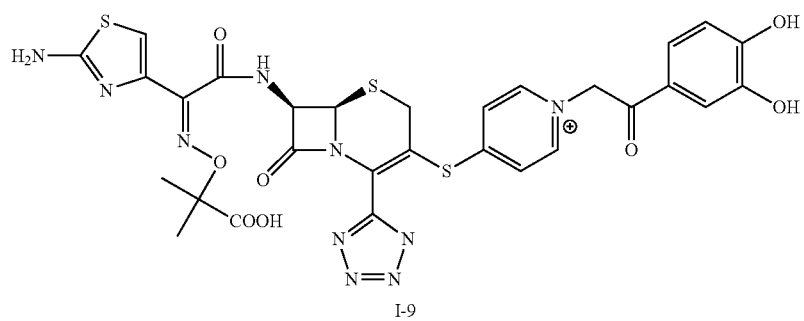
I-9

Compound 9l→Compound 9m

To a solution of Compound 1i (34 mg) in DMF (1.5 ml) was added BSA (26 μl), and the mixture was stirred at room temperature for 10 minutes. The solution was added to a solution of Compound 9l (140 mg) and NaBr (43 mg) in DMF (0.5 ml). The mixture was reacted at room temperature for 4 hours, and further reacted at 8° C. for 15 hours. The reaction mixture was poured into aqueous sodium chloride solution, and the resulting precipitates were collected by filtration, and washed with water. The corrected precipitates were dissolved in methylene chloride, washed with water and concentrated to give crude Compound 9m (179 mg).

MS (ESI): 1155.8$^+$ (M+H)$^+$

Compound 9m→Compound I-9

Compound 9m (179 mg) was dissolved in methylene chloride (1.3 ml), and thereto were added anisole (0.12 ml) and TFA (1.8 ml), and the mixture was stirred at room temperature for 1.5 hour. The mixture was concentrated, and thereto was added ether for pulverization. The obtained powder was collected by filtration, purified by HP-20 column chromatography, and lyophilized to give Compound I-9 (17 mg).

$^1$H-NMR (d$_6$-DMSO) δ: 1.35 (3H, s), 1.39 (3H, s), 3.09, 3.78 (2H, AB-q, J=17.7 Hz), 5.52 (1H, d, J=5.4 Hz), 5.84 (1H, dd, J=5.4, 7.8 Hz), 6.06 (2H, bs), 6.65 (1H, s), 6.86 (1H, d, J=8.1 Hz), 7.20 (1H, bs), 7.30-7.39 (3H, m), 7.77 (2H, d, J=6.9 Hz), 8.53 (2H, d, J=6.9 Hz)

MS (ESI): 739.4$^+$ (M+H)$^+$

Example 10

Synthesis of Compound I-10

[Formula 96]

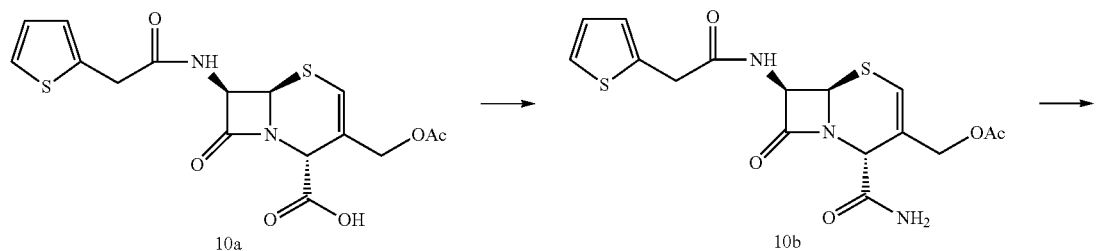

-continued
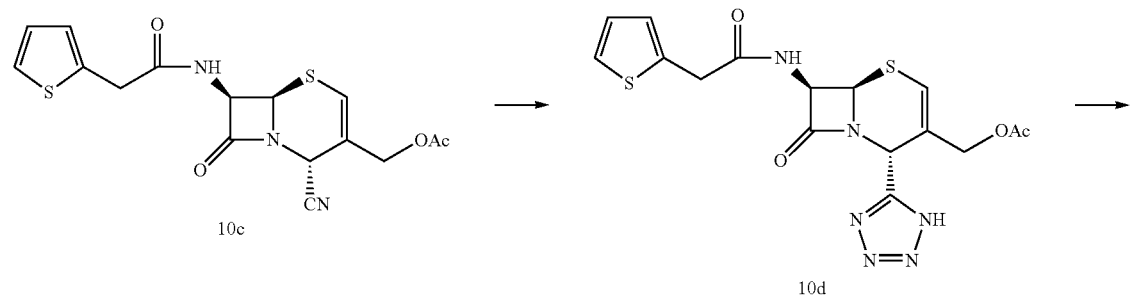
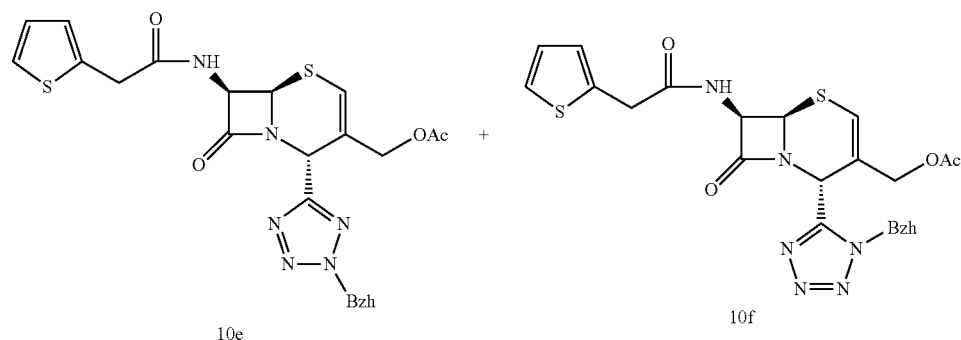
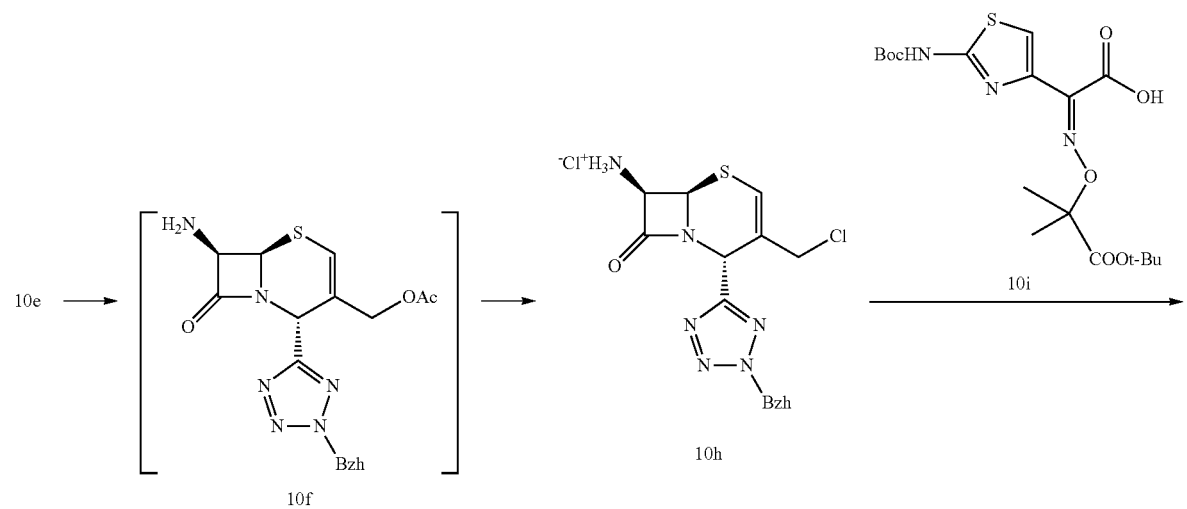
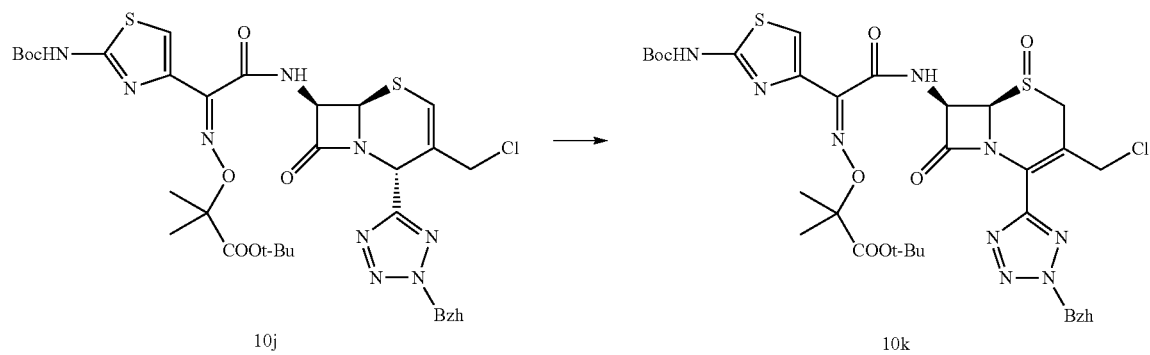

-continued
[Formula 97]
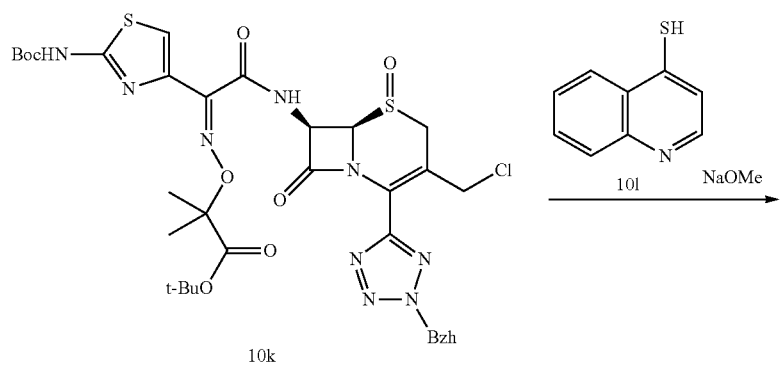
10k
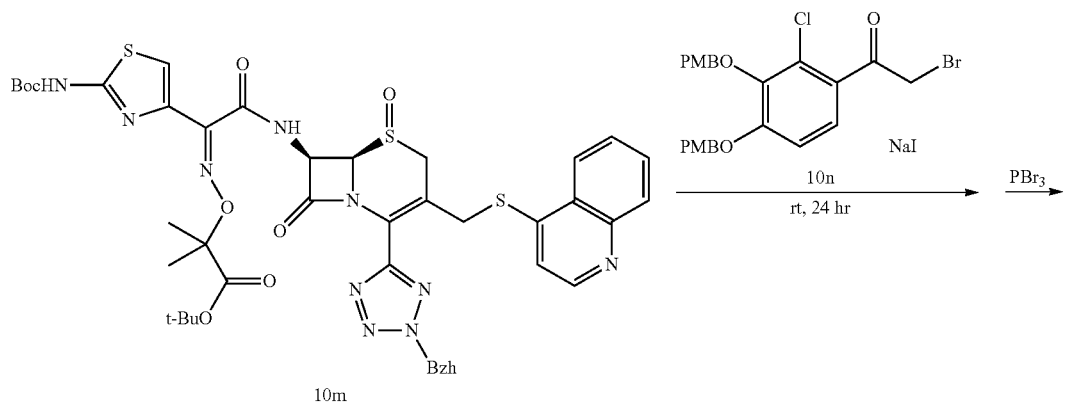
10m
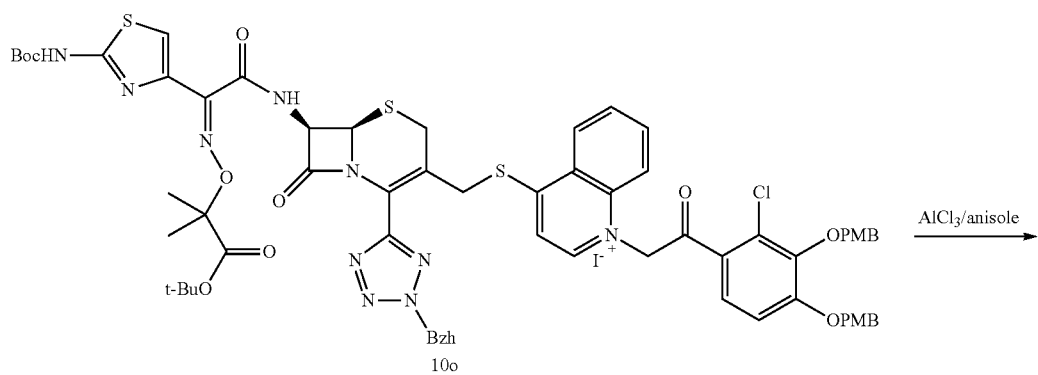
10o
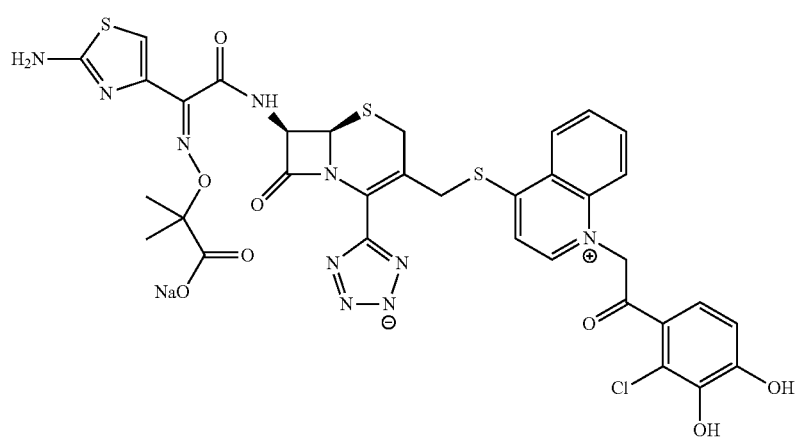
I-10

1) Compound 10a→Compound 10b

A known compound 10a (100 mg, 0.252 mmol) was dissolved in 1,4-dioxane (1 mL), and thereto were added Di-tert-butyl dicarbonate (0.076 mL, 0.328 mmol), ammonium carbonate (30.3 mg, 0.315 mmol), and pyridine (0.010 mL, 0.126 mmol), and then the mixture was stirred at room temperature overnight. The reaction mixture was added purified water, and extracted with a mixture of ethyl acetate and tetrahydrofuran. The organic phase was washed with purified water and brine, and dried over magnesium sulfate anhydride. The drying agent was filter out, and the solvent was removed under reduced pressure. The deposited solid was collected by filtration, and washed with ethyl acetate to give Compound 10b as white solid (75 mg, 75%).

$^1$H-NMR (DMSO-$d_6$) δ: 9.20 (1H, d, J=7.5 Hz), 7.36 (1H, dt, J=5.0, 1.1 Hz), 6.97-6.89 (2H, m), 6.72 (1H, s), 5.43 (1H, dd, J=7.5, 3.7 Hz), 5.15 (1H, d, J=3.7 Hz), 4.90 (1H, s), 4.64 (2H, dd, J=18.1, 12.7 Hz), 3.76 (2H, s), 2.02 (3H, s).

2) Compound 10b→Compound 10c

Compound 10b (13.2 g, 33.4 mmol) was suspended in tetrahydrofuran (135 mL), and cooled at −20° C. The mixture was added pyridine (8.11 mL, 100 mmol) and then added trifluoroacetic anhydride (7.06 mL, 50.1 mmol), and stirred at −20° C. for 30 minutes. The reaction mixture was added purified water, and extracted with ethyl acetate. The organic phase was washed with purified water and brine, dried over magnesium sulfate anhydride. The drying agent was filtered out and the filtrate was concentrated under reduced pressure. The obtained residue was purified by silica gel chromatography to give Compound 10c as an orange form (13.88 g, quantitative).

$^1$H-NMR (CDCl$_3$) δ: 7.29-7.25 (1H, m), 7.02-6.97 (2H, m), 6.53 (1H, d, J=1.1 Hz), 6.32 (1H, d, J=8.2 Hz), 5.72 (1H, dd, J=8.2, 4.1 Hz), 5.26 (1H, d, J=1.1 Hz), 5.11 (1H, d, J=4.1 Hz), 4.73 (1H, d, J=13.2 Hz), 4.61 (1H, d, J=13.2 Hz), 3.87 (2H, s), 2.09 (3H, s).

3) Compound 10c→Compound 10d

Compound 10c (273 mg, 0.723 mmol) was dissolved in 1,4-dioxane, and added trimethylsilylazide (0.192 mL, 1.447 mmol), and then added dibuthylthin oxide (18.01 mg, 0.072 mmol), and the mixture was stirred at 90° C. for one hour and 30 minutes. The reaction mixture was cooled to room temperature, and then concentrated under reduced pressure. The residue was added purified water and extracted with ethyl acetate. The organic phase was washed with purified water and brine, and dried over magnesium sulfate anhydride. The drying agent was filtered out and the filtrate was concentrated under reduced pressure. The obtained residue was purified by silica gel chromatography to give Compound 10d (169.2 mg, 56%).

$^1$H-NMR (DMSO-$d_6$) δ: 9.25 (1H, d, J=7.8 Hz), 7.36 (1H, dd, J=4.9, 1.4 Hz), 6.97-6.85 (3H, m), 5.90 (1H, d, J=1.5 Hz), 5.44 (1H, dd, J=7.8, 4.0 Hz), 5.14 (1H, d, J=4.0 Hz), 4.60 (1H, d, J=12.7 Hz), 4.53 (1H, d, J=12.7 Hz), 3.77 (2H, s), 1.90 (3H, s).

4) Compound 10d→Compound 10e

Compound 10d (85 mg, 0.243 mmol) was dissolved in tetrahydrofuran (1 mL), and added diphenyldiazomethane (47.1 mg, 0.243 mmol) and the mixture was stirred for 3 hours and 30 minutes. Further thereto was added diphenyldiazomethane (11.8 mg, 0.606 mmol) and stirred for 35 minutes. The reaction mixture was concentrated under reduced pressure, and the obtained residue was purified by silica gel chromatography to give Compound 10e (72 mg, 61%) and Compound 10f. The position of diphenylmethyl radical was determined by nuclear Overhauser effect of $^1$H NMR.

Compound 10e (Less Polar One)

$^1$H-NMR (CDCl$_3$) δ: 7.41-7.12 (13H, m), 7.03-6.91 (2H, m), 6.41 (1H, s), 6.37 (1H, d, J=9.1 Hz), 5.80 (1H, s), 5.64 (1H, dd, J=9.1, 4.0 Hz), 5.26 (1H, d, J=4.0 Hz), 4.51 (1H, d, J=12.8 Hz), 4.39 (1H, d, J=12.8 Hz), 3.86 (2H, s), 1.89 (3H, s).

Compound 10f (More Polar One)

$^1$H-NMR (CDCl$_3$) δ: 7.42-7.33 (5H, m), 7.28-7.18 (4H, m), 7.13 (2H, dd, J=6.6, 3.0 Hz), 7.02-6.95 (2H, m), 6.90 (1H, s), 6.57 (1H, d, J=1.4 Hz), 6.30 (1H, d, J=9.1 Hz), 5.80 (1H, d, J=1.4 Hz), 5.01 (1H, dd, J=9.1, 4.0 Hz), 4.64 (1H, d, J=12.8 Hz), 4.58 (1H, d, J=4.0 Hz), 4.51 (1H, d, J=12.8 Hz), 3.82 (2H, s), 1.80 (3H, s).

5) Compound 10e→Compound 10h

Phosphorus pentachloride (9.12 g, 43.8 mmol) was suspended in methylene chloride (130 mL), and the mixture was cooled at 0° C. The suspension was added pyridine (3.90 mL, 48.2 mmol), and then added Compound 10e (12.8 g, 21.9 mmol), and stirred at room temperature for 45 minutes. The reaction mixture was cooled at −40° C., and added methanol (13.3 mL, 328 mmol) at once, and the mixture was allowed to room temperature. The reaction mixture was added purified water (130 mL), and the aqueous phase was extracted with methylene chloride. The methylene chloride phase was washed over saturated aqueous NaHCO$_3$ and brine, and dried over magnesium sulfate anhydrous. The drying agent was filtered out, the organic phase was added 4 mmol/l HCl-1,4-dioxane (27.4 mL, 109 mmol), and stirred at room temperature for 3 hours and 15 minutes. The reaction mixture was added 1,4-dioxane (150 ml), and concentrated under reduced pressure until the total volume was about 30 mL. The obtained solution was added acetonitrile (100 mL), and added seed crystals and stirred at room temperature. The precipitated crystals were collected by filtration to give Compound 10h (7.92 g, 73%). (The seed crystals were obtained by the treatment that the jellied crude product 10h, as the condensed residue which was similarly obtained by above handling, was suspended in acetonitrile, and triturated with a spatula.)

$^1$H-NMR (DMSO-$d_6$) δ: 8.82 (2H, br s), 7.72 (1H, s), 7.45-7.26 (11H, m), 7.00 (1H, d, J=1.2 Hz), 5.94 (1H, d, J=1.2 Hz), 5.19 (1H, d, J=4.2 Hz), 4.94 (1H, d, J=4.2 Hz), 4.48 (1H, d, J=11.8 Hz), 4.16 (1H, d, J=11.8 Hz).

6) Compound 10h→Compound 10j

Compound 10h was suspended in ethylene chloride (40 ml) and cooled to −40° C. The suspension was added Compound 10i (3.54 g, 8.24 mmol), phenyl dichlorophospate (1.85 mL, 12.36 mmol), and added dropwise N-methylmorpholine (3.62 mL, 33.0 mmol), and stirred at −40° C. for 30 minutes. The reaction mixture was added purified water and extracted with ethyl acetate. The obtained organic phase was washed with purified water and brine, and dried over magnesium sulfate anhydrite. The drying agent was filtered out, the filtrate was concentrated under reduced pressure to give Compound 10j (7.8 g, quantitative).

$^1$H-NMR (CDCl$_3$) δ: 8.32 (1H, d, J=8.5 Hz), 7.41-7.15 (16H, m), 6.46 (1H, s), 5.99 (1H, s), 5.79 (1H, dd, J=8.5, 4.0 Hz), 5.37 (1H, d, J=4.0 Hz), 5.29 (1H, s), 4.15-4.01 (2H, m), 1.63 (3H, s), 1.60 (3H, s), 1.52 (9H, s), 1.42 (9H, s).

7) Compound 10j→Compound 10k

Compound 10j (2.30 g, 2.7 mmol) was dissolved in methylene chloride (25 mL), and cooled to −40° C. The solution was added m-chloro perbenzoic acid (788 mg, 2.97 mmol) and stirred at −40° C. for one hour and 15 minutes. The reaction mixture was added sodium hydrogen sulfite solution, and then methylene chloride was removed under reduced pressure. The condensed solution was extracted with ethyl acetate, then the organic phase was washed with sodium bicarbonate water, purified water and brine, and dried over magnesium sulfate anhydride. The drying agent was filtered out, and the filtrate was concentrated under reduced pressure. The obtained residue was purified by silica gel chromatography to give Compound 10k (1.41 g, 60%). Compound 10k was suspended in ethanol and triturated with a spatula to give its crystal.

$^1$H-NMR (CDCl$_3$) δ: 8.08 (1H, br s), 7.90 (1H, d, J=9.9 Hz), 7.39-7.18 (20H, m), 6.29 (1H, dd, J=9.7, 5.0 Hz), 5.13 (1H, d, J=12.4 Hz), 4.73 (1H, d, J=4.9 Hz), 4.29 (1H, d, J=12.1 Hz), 3.90 (1H, d, J=19.0 Hz), 3.50 (1H, d, J=19.0 Hz), 1.59 (6H, d, J=7.1 Hz), 1.56 (9H, s), 1.38 (10H, s).

8) Compound 10k→Compound 10m

A solution of Compound 10l (195 mg, 1.21 mmol) in methanol (5 ml) was added 1 mol/l NaOMe methanol solution (1.1 ml, 1.10 mmol) under ice-cooling, and stirred at room temperature for 30 minutes. After methanol was evaporated, the residue was dissolved in N,N-dimethylformamide and added to a solution of Compound 10k (953 mg, 1.10 mmol) in N,N-dimethylformamide (5 mL). After the reaction mixture was stirred at room temperature for 30 minutes, the reaction mixture was added saturated aqueous ammonium chloride and extracted with ethyl acetate. The organic phase was washed with water and brine, and dried over magnesium sulfate. The condensed residue was purified by preparative liquid chromatography to give Compound 10m (1.1 g, 100%).

MS: m/z=991.41 [M+H]

$^1$H-NMR (CDCl$_3$) δ: 1.40 (9H, s), 1.53 (9H, s), 1.59 (3H, s), 1.61 (3H, s), 3.45 (1H, d, J=15.9 Hz), 3.94 (1H, d, J=11.9 Hz), 4.00 (1H, d, J=15.9 Hz), 4.63 (1H, d, J=2.4 Hz), 4.80 (2H, d, J=11.9 Hz), 6.22 (1H, dd, J=9.9, 4.9 Hz), 6.81 (1H, d, J=4.9 Hz), 7.23-7.41 (13H, m), 7.52 (1H, t, J=7.6 Hz), 7.71 (1H, t, J=7.6 Hz), 7.86 (1H, d, J=9.9 Hz), 8.07 (1H, t, J=7.6 Hz), 8.41 (1H, d, J=4.9 Hz).

10) Compound 10o→Compound I-10

The obtained whole Compound 10o (1.11 mmol suitability) was dissolved in dichloromethane (15 ml) and cooled to −15° C., then added anisole (1.82 ml, 16.7 mmol) and 2 mol/l aluminium chloride/nitromethane solution (8.33 ml, 16.7 mmol) and stirred at 0° C. for one hour. The reaction mixture was dissolved in water, 2 mol/l aqueous hydrochloride and acetonitrile then washed with diisopropyl ether. The aqueous phase was added HP20-2S resin and distilled out acetonitrile. The obtained mixed liquid was subjected to HP20-SS column chromatography and eluted with water/acetonitrile. The obtained solution was concentrated under reduced pressure, and then lyophilized to give Compound I-10 (250.0 mg, 26%) as white powder.

MS: m/z=837.24 [M+H]

$^1$H-NMR (DMSO-D6) δ: 1.42 (3H, s), 1.48 (3H, s), 3.62 (1H, d, J=17.1 Hz), 3.80 (1H, d, J=17.1 Hz), 4.60 (1H, d, J=12.2 Hz), 4.73 (1H, d, J=12.2 Hz), 5.35 (1H, d, J=4.8 Hz), 5.80 (1H, dd, J=7.7, 4.8 Hz), 6.52 (1H, d, J=17.2 Hz), 6.75 (1H, s), 6.76 (1H, d, J=17.2 Hz), 6.85 (1H, d, J=8.2 Hz), 7.25 (2H, brs), 7.49 (1H, d, J=8.5 Hz), 7.76 (1H, d, J=7.3 Hz), 7.86 (1H, t, J=7.3 Hz), 8.05-8.11 (2H, m), 8.40 (1H, d, J=8.2 Hz), 9.13 (1H, d, J=7.3 Hz), 10.09 (1H, brs).

Elemental analysis: C34H28ClN10O8S3Na(H2O)4

Calculated: C, 43.85; H, 3.90; Cl, 3.81; N, 15.04; S, 10.33; Na, 2.47(%).

Found: C, 44.10; H, 4.04; Cl, 4.07; N, 14.77; S, 10.12; Na, 1.55(%).

Example 11

Compound I-11

Compound I-11 was synthesized in a similar manner as described for Compound I-10.

[Formula 98]

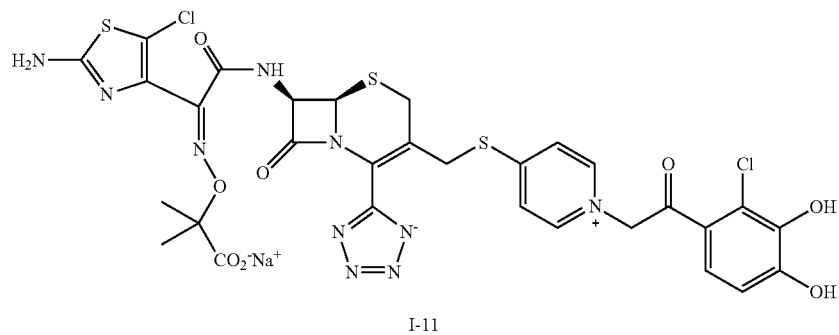

I-11

9) Compound 10m→Compound 10o

A solution of Compound 10m (1.1 g, 1.11 mmol) in N,N-dimethylformamide (5 mL) was added Compound 10n (561 mg, 1.11 mmol) and stirred at 55° C. for 8 hours. The reaction mixture was cooled to −40° C. and added PBr$_3$ (0.21 ml, 2.22 mmol) and stirred at −40° C. for 30 minutes. The reaction mixture was added 5% aqueous sodium chloride and extracted with ethyl acetate. The organic phase was washed with water and brine, and dried over magnesium sulfate. Compound 10o was used in the subsequent reaction without any further purification.

$^1$H-NMR (D$_2$O) δ: 8.38-8.38 (m, 2H), 7.57-7.56 (m, 2H), 6.97-6.96 (m, 2H), 5.86-5.86 (m, 1H), 5.38-5.37 (m, 1H), 4.53-4.49 (m, 1H), 4.12-4.09 (m, 1H), 3.89-3.85 (m, 1H), 3.65-3.61 (m, 1H), 1.51 (s, 3H), 1.48 (s, 3H).

MS (m+1)=778.91

Example 12

Compound I-12

Compound I-12 was synthesized in a similar manner as described for Compound I-10.

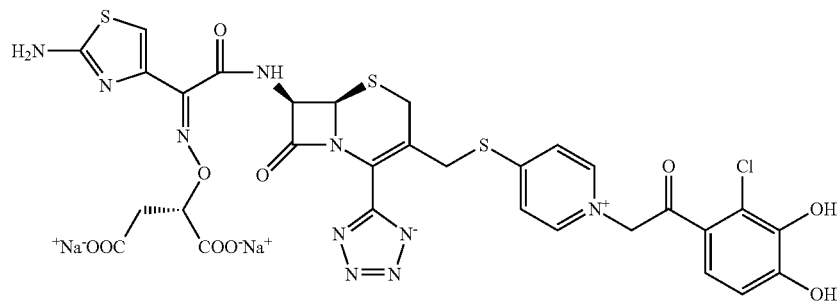
I-12
$^1$H-NMR (D$_2$O) δ: 8.25 (d, J=6.8 Hz, 2H), 7.54-7.45 (m, 3H), 6.99 (s, 1H), 6.94 (d, J=8.8 Hz, 1H), 5.81 (d, J=4.8 Hz, 1H), 5.36 (d, J=4.8 Hz, 1H), 4.97 (dd, J=9.5, 3.6 Hz, 1H), 4.50 (d, J=14.0 Hz, 1H), 4.11 (d, J=14.0 Hz, 1H), 3.87 (d, J=17.8 Hz, 1H), 3.64 (d, J=17.8 Hz, 1H), 2.72 (d, J=9.2 Hz, 2H).
MS (m+1)=816.89
Example 13
Compound I-13
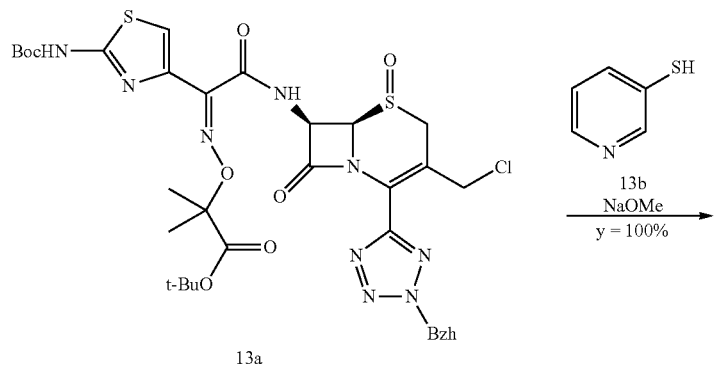
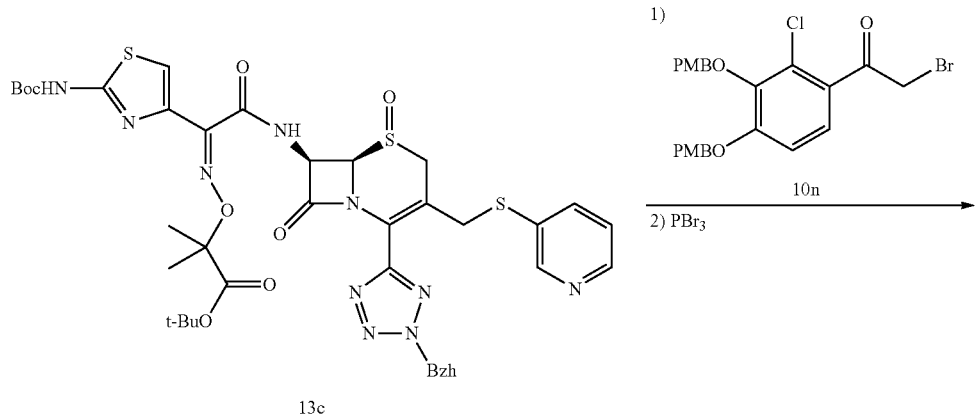

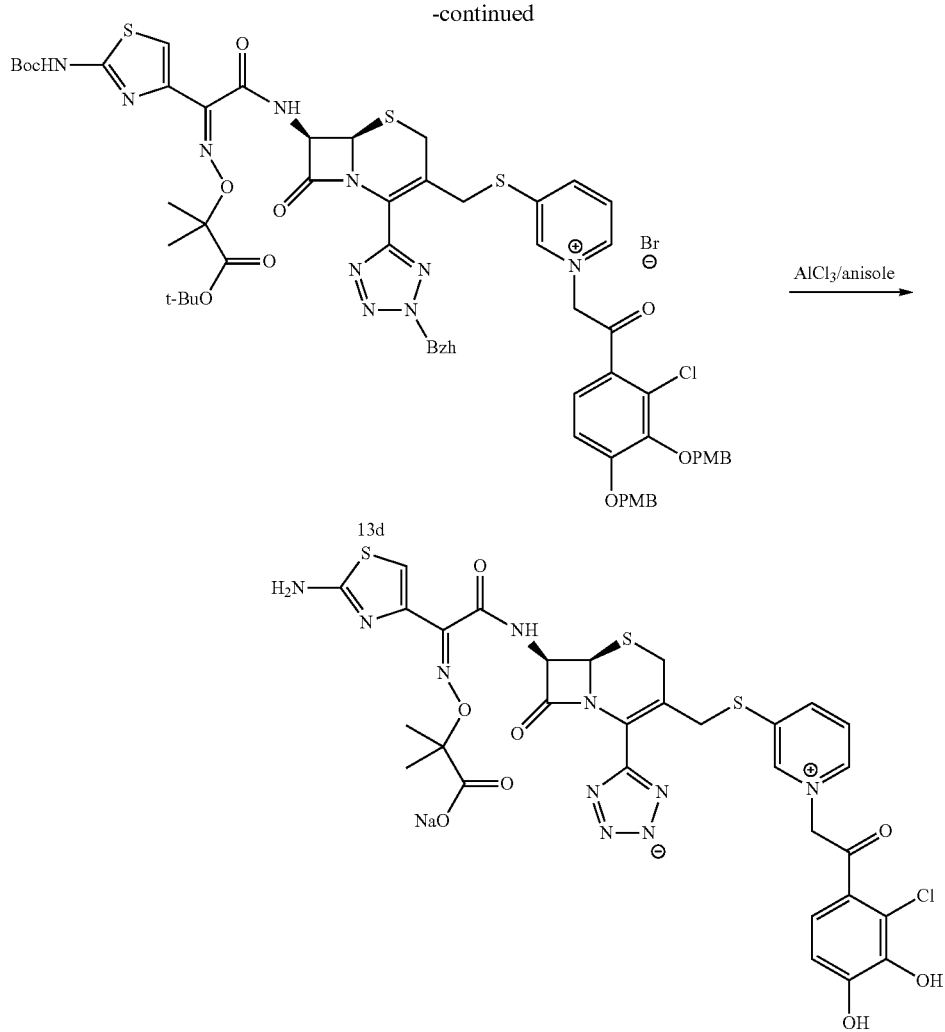

I-13

1) Compound 13a→Compound 13c

A solution of compound 13b (171 mg, 1.54 mmol) in methanol (5 ml) was added 1 mol/l NaOMe methanol solution (1.1 ml, 1.10 mmol) under ice-cooling and stirred for 30 minutes at room temperature. After methanol was removed, the residue was dissolved in N,N-dimethylformamide (2 ml) and added a solution of compound 13a (953 mg, 1.10 mmol) in N,N-dimethylformamide (5 ml). The mixture was stirred at room temperature for 30 minutes, the reaction solution was added saturated aqueous ammonium chloride and extracted with ethyl acetate. The organic phase was washed with water and brine, and dried over magnesium sulfate. The condensed residue was purified by preparative liquid chromatography to give Compound 13c (1.0 g, 100%).

MS: m/z=941.23 [M+H]

$^1$H-NMR (CDCl$_3$) δ: 1.42 (9H, s), 1.59 (3H, s), 1.61 (3H, s), 1.63 (9H, s), 3.50 (1H, d, J=17.5 Hz), 3.73 (1H, d, J=14.2 Hz), 4.00 (1H, d, J=17.5 Hz), 4.54 (1H, d, J=14.2 Hz), 4.65 (1H, d, J=4.6 Hz), 6.23 (1H, dd, J=9.9, 4.6 Hz), 6.74 (1H, dd, J=7.9, 4.6 Hz), 7.25-7.28 (4H, m), 7.35-7.41 (9H, m), 7.90 (1H, d, J=9.9 Hz), 8.17 (1H, d, J=4.8 Hz), 8.21 (1H, brs), 8.44 (1H, d, J=2.1 Hz).

2) Compound 13c→Compound 13d

A solution of compound 13c (1.1 g, 1.17 mmol) in N,N-dimethylformamide (5 mL) was added compound 10n (591 mg, 1.17 mmol) and stirred at room temperature for 18 hours. The reaction solution was cooled at −40° C. and added PBr$_3$ (0.22 ml, 2.34 mmol) and stirred at −40° C. for 30 minutes. The reaction solution was added 5% aqueous sodium chloride and extracted with ethyl acetate. The organic phase was washed with water and brine and then dried over magnesium sulfate. The compound 13d was used in the subsequent reaction without any further purification.

3) Compound 13d→Compound I-13

The whole amount of compound 13d thus obtained (1.17 mmol equivalent) was dissolved in dichloromethane (15 ml) and cooled to −15° C., then added anisole (1.92 ml, 17.6 mmol) and 2 mol/l alminium chloride/nitromethane solution (8.78 ml, 17.6 mmol) sequentially, and stirred at 0° C. for one hour. The reaction solution was dissolved in water, 2 mol/l hydrochloric acid and acetonitrile, and then washed with diisopropyl ether. The aqueous phase was added HP20-SS resin, and actonitrile was removed under reduced pressure. The obtained mixed liquid was subjected to HP20-SS column chromatography, and eluted with water/acetonitrile. The obtained solution was concentrated under reduced pressure, and then lyophilized to give compound I-13 (320.0 mg, 34%) as white powder.

MS: m/z=787.30 [M+H]

$^1$H-NMR (DMSO-D6) δ: 1.38 (3H, s), 1.45 (3H, s), 3.42 (1H, d, J=17.4 Hz), 3.62 (1H, d, J=17.4 Hz), 4.20 (1H, d, J=12.8 Hz), 4.32 (1H, d, J=12.8 Hz), 5.25 (1H, d, J=5.0 Hz), 5.74 (1H, dd, J=7.1, 5.0 Hz), 6.05 (1H, d, J=14.9 Hz), 6.25 (1H, d, J=14.9 Hz), 6.72 (1H, s), 6.76 (1H, d, J=8.7 Hz), 7.23 (2H, brs), 7.37 (1H, d, J=8.7 Hz), 7.95 (1H, t, J=7.2 Hz), 8.47 (1H, d, J=8.7 Hz), 8.90 (1H, d, J=5.9 Hz), 9.26 (1H, s), 10.52 (1H, brs).
Elemental analysis: C30H26ClN10O8S3Na(H2O)4.7
Calculated: C, 40.31; H, 3.99; Cl, 3.97; N, 15.67; S, 10.76; Na, 2.57(%).
Found: C, 40.30; H, 4.06; Cl, 3.83; N, 15.92; S, 10.72; Na, 1.80(%).
Example 14
Synthesis of Compound I-14
[Chemical formula 101]
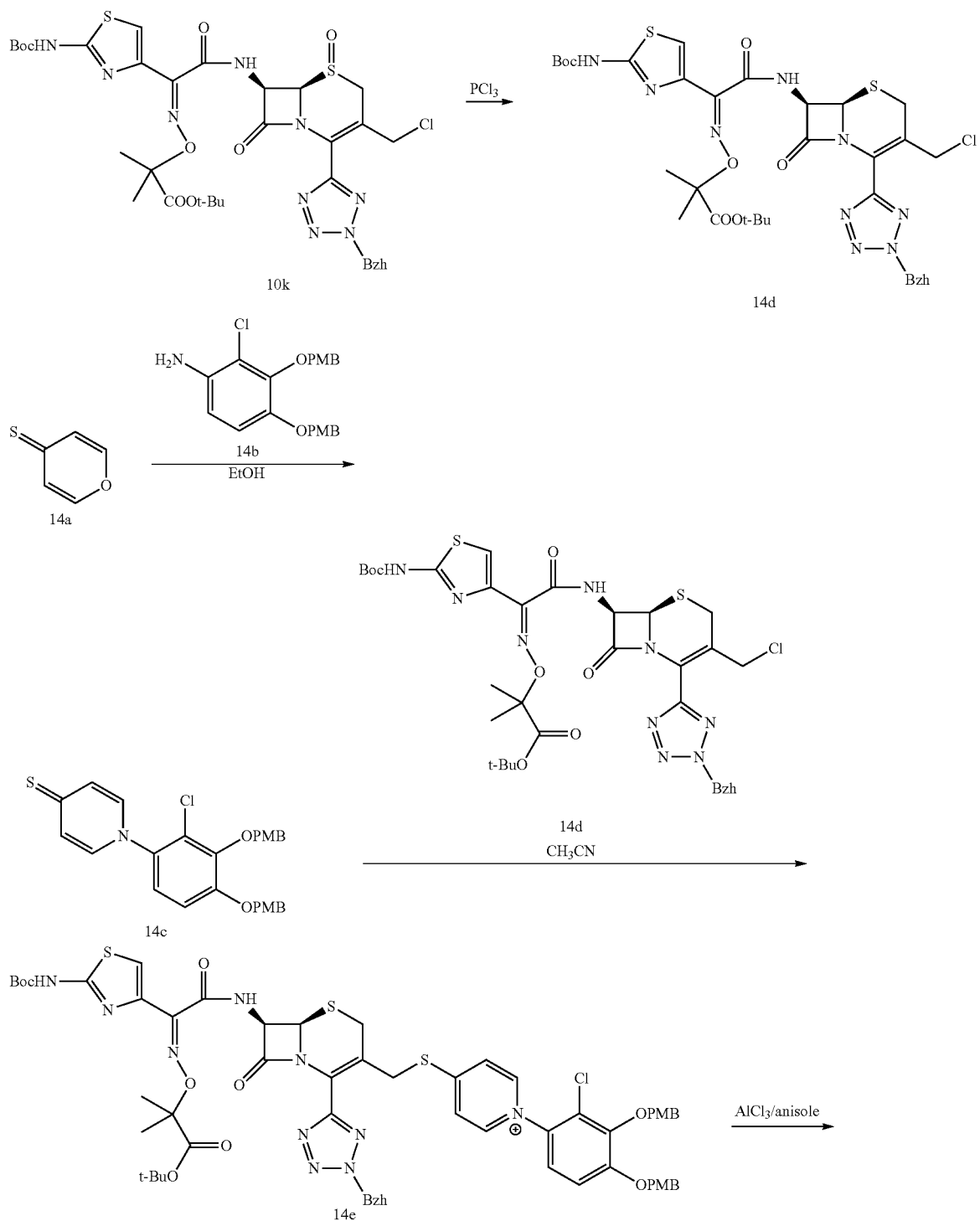

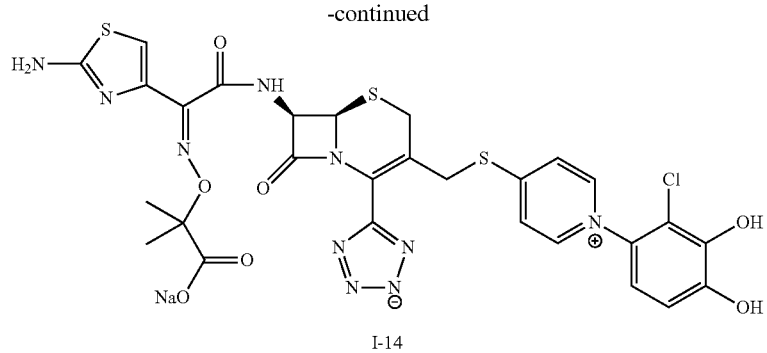

I-14

1) Compound 10k→Compound 14d

Compound 10k was dissolved in N,N-dimethylformamide (60 mL), and the solution was cooled to −78° C. The solution was added phosphorus trichloride (1.92 g, 14.0 mmol) and stirred at −78° C. for 30 minutes. The reaction solution was added water and extracted with ethyl acetate, and the organic phase was washed with purified water and brine, and dried over anhydrous magnesium sulfate. The drying agent was filtered out, and the solvent was removed under reduced pressure. The obtained residue was purified with silica-gel chromatography to give Compound 14d (yield 5.90 g, yield constant 99%).

$^1$H-NMR (CDCl$_3$) δ: 1.39 (9H, s), 1.53 (9H, s), 1.59 (3H, s), 1.63 (3H, s), 3.55 (1H, d, J=18.0 Hz), 3.75 (1H, d, J=18.0 Hz), 4.41 (1H, d, J=11.9 Hz), 4.59 (1H, d, J=11.9 Hz), 5.22 (1H, d, J=5.0 Hz), 6.07 (1H, dd, J=8.8, 5.0 Hz), 7.27-7.39 (12H, m), 8.07 (1H, s), 8.11 (1H, d, J=8.8 Hz).

2) Compound 14a→Compound 14c

A solution of Compound 14a (224 mg, 2.00 mmol) in ethanol (5 ml) was added compound 14b (880 mg, 2.20 mmol) and stirred at 100° C. for 3 days with dehydration. After ethanol was removed, the concentrated residue was purified by preparative liquid chromatography to give Compound 14c (512 mg, yield constant 52%).

MS: m/z=494.17 [M+H]

$^1$H-NMR (CDCl$_3$) δ: 3.85 (3H, s), 3.89 (3H, s), 5.08 (2H, s), 5.17 (2H, s), 6.89 (2H, d, J=8.6 Hz), 6.99 (2H, d, J=8.6 Hz), 7.07 (2H, d, J=8.6 Hz), 7.13 (2H, d, J=8.6 Hz), 7.36 (2H, d, J=8.6 Hz), 7.41 (2H, d, J=8.6 Hz), 7.54 (2H, dd, J=5.5, 1.5 Hz).

3) Compound 14c→Compound 14e

A solution of compound 14c (0.87 g, 1.76 mmol) in acetonitrile (10 mL) was added compound 14d (1.5 g, 1.76 mmol) and stirred at room temperature for 18 hours. Acetonitrile was removed under reduced pressure, and the solvent was dried under reduced pressure. Compound 14e was used in the subsequence step without any further purification.

4) Compound 14e→Compound I-14

The obtained compound 14e (1.31 g, 1.00 mmol equivalent) was dissolved in dichloromethane (15 mL) and cooled to −15° C. and added anisole (1.64 ml, 15.0 mmol) and 2 mol/l aluminum chloride/nitromethane solution (7.50 ml, 15.9 mmol) sequentially, and stirred at 0° C. for one hour. The reaction mixture was dissolved in water, 2 mol/l hydrochloride in water and acetonitrile, and then washed with diisopropy ether. The aqueous phase was added HP20-SS resin, and actonitrile was removed under reduced pressure. The obtained mixed liquid was purified by HP20-SS column chromatography and eluted with water/acetonitrile. The obtained liquid was concentrated under reduced pressure, and then lyophilized to give compound I-14 (290.0 mg, 37%) as white powder.

MS: m/z=745.26 [M+H]

$^1$H-NMR (DMSO-D6) δ: 1.40 (3H, s), 1.48 (3H, s), 3.45 (1H, d, J=12.4 Hz), 3.47 (1H, d, J=12.4 Hz), 4.47 (1H, d, J=12.4 Hz), 4.68 (1H, d, J=12.4 Hz), 5.32 (1H, d, J=4.4 Hz), 5.78-5.85 (1H, m), 6.77 (1H, s), 6.91 (1H, d, J=8.6 Hz), 7.01 (1H, d, J=8.6 Hz), 7.24 (2H, s), 7.99 (2H, d, J=6.9 Hz), 8.75 (2H, d, J=6.9 Hz), 10.61 (1H, brs).

Elemental analysis: C28H24ClN10O7S3Na(H2O)5.0

Calculated: C, 39.23; H, 4.00; Cl, 4.14; N, 16.34; S, 11.22; Na, 2.68(%).

Found: C, 39.28; H, 4.04; Cl, 4.12; N, 16.27; S, 11.19; Na, 1.90(%).

Example 15

Synthesis of Compound I-15

Compound I-15 was synthesized in a similar manner as described for compound I-14.

[Chemical formula 102]

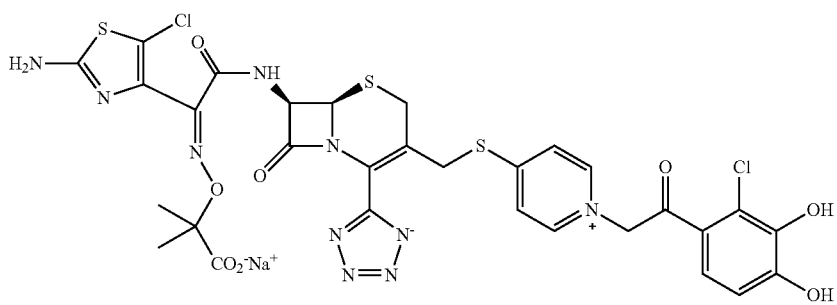

I-15

$^1$H-NMR (D$_2$O) δ: 8.23-8.20 (m, 2H), 7.45-7.38 (m, 3H), 6.81-6.78 (m, 1H), 5.85-5.83 (m, 1H), 5.37-5.35 (m, 1H), 4.44-4.39 (m, 2H), 4.06-3.58 (m, 4H), 1.52-1.48 (m, 6H).

MS (m+1)=820.92

Example 16

Synthesis of Compound I-16

Compound I-16 was synthesized in a similar manner as described for compound I-14.

[Chemical formula 103]

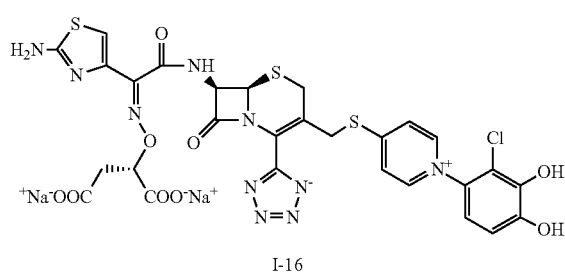

I-16

$^1$H-NMR (D$_2$O) δ: 8.53 (d, J=7.0 Hz, 2H), 7.90 (d, J=7.0 Hz, 2H), 7.20 (s, 1H), 7.11 (d, J=8.8 Hz, 1H), 7.02 (d, J=8.8 Hz, 1H), 5.82 (d, J=4.8 Hz, 1H), 5.49 (d, J=4.8 Hz, 1H), 5.29 (dd, J=7.3, 4.7 Hz, 1H), 4.46 (dd, J=22.3, 13.4 Hz, 2H), 3.95 (d, J=18.2 Hz, 1H), 3.76 (d, J=18.1 Hz, 1H), 3.19-3.07 (m, 2H).

MS (m+1)=774.84

Example 17

Synthesis of Compound I-17

Compound I-17 was synthesized in a similar manner as described for compound I-14.

[Chemical formula 104]

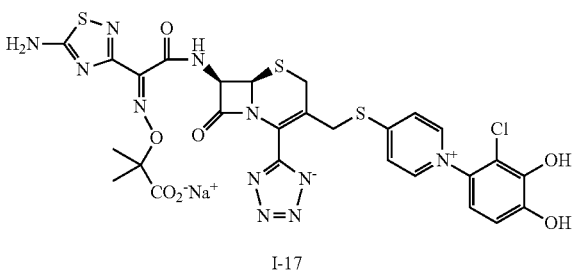

I-17

$^1$H-NMR (D$_2$O) δ: 8.41 (2H, d, J=6.8 Hz), 7.57 (2H, d, J=6.8 Hz), 6.98 (2H, s), 5.90 (1H, d, J=4.6 Hz), 5.42 (1H, d, J=4.6 Hz), 4.54 (1H, d, J=14.1 Hz), 4.11 (1H, d, J=14.1 Hz), 4.11 (1H, s), 4.11 (1H, s), 3.93 (1H, d, J=17.8 Hz), 3.67 (1H, d, J=17.8 Hz), 1.55 (3H, s), 1.53 (3H, s).

MS (m+1)=746.00

Example 18

Synthesis of Compound I-18

[Chemical Formula 105]

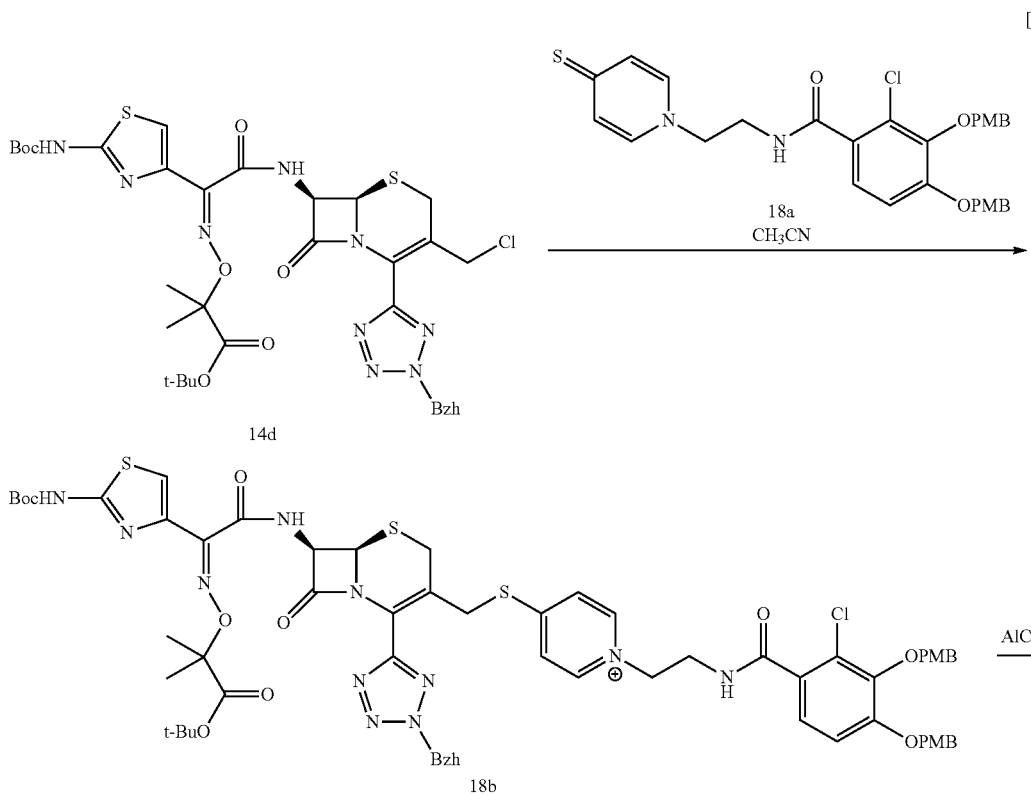

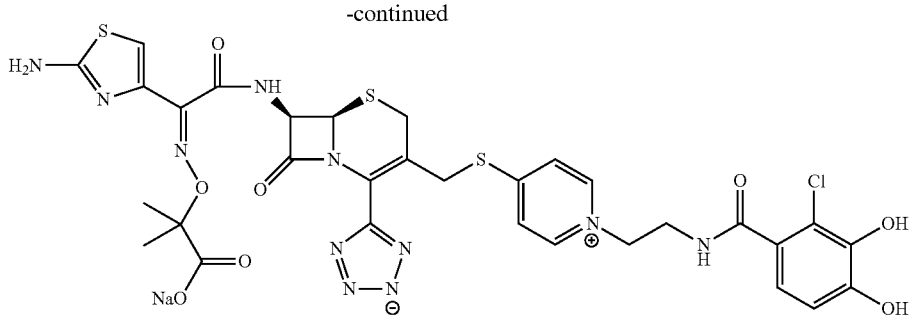

I-18

1) Compound 14d→Compound 18b

A solution of compound 14d (1.23 g, 1.45 mmol) in acetonitrile (10 mL) was added compound 18a (0.82 g, 1.45 mmol) and stirred at room temperature for 18 hours. Acetonitrile was removed under reduced pressure, and the solvent was dried under reduced pressure. Compound 18b was used in the subsequent reaction without any further purification.

2) Compound 18b→Compound I-18

The obtained compound 18b (1.10 g, 0.80 mmol equivalent) was dissolved in dichloromethane (15 ml) and cooled to −15° C., and added anisole (1.31 ml, 12.0 mmol) and 2 mol/l aluminum chloride/nitromethane solution (6.00 ml, 12.0 mmol) sequentially, and stirred at 0° C. for one hour. The reaction mixture was dissolved in water, 2 mol/l hydrochloride in water and acetonitrile, and then washed with diisopropyl ether. The aqueous phase was added HP20-SS resin and actonitrile was removed under reduced pressure. The obtained mixed liquid was subjected to HP20-SS column chromatography and eluted with water/acetonitrile. The obtained solution was concentrated under reduced pressure, and then lyophilized to give compound I-18 (310.0 mg, 46%) as white powder.

MS: m/z=816.26 [M+H]

$^1$H-NMR (DMSO-D6) δ: 1.34 (3H, s), 1.45 (3H, s), 3.45 (1H, d, J=17.2 Hz), 3.65 (1H, d, J=17.2 Hz), 3.78-3.81 (2H, m), 4.44-4.48 (3H, m), 4.56 (1H, s), 5.25 (1H, d, J=5.0 Hz), 5.81-5.84 (1H, m), 6.52 (1H, d, J=7.6 Hz), 6.74 (1H, s), 6.82 (1H, d, J=7.6 Hz), 7.20 (2H, s), 8.01-8.05 (2H, m), 8.20 (1H, s), 8.60 (2H, d, J=6.9 Hz), 10.23 (1H, s).

Elemental analysis: C31H29ClN11O8S3Na(H2O)3.9

Calculated: C, 40.98; H, 4.08; Cl, 3.90; N, 16.96; S, 10.59; Na, 2.53(%).

Found: C, 41.02; H, 4.20; Cl, 3.82; N, 17.08; S, 10.32; Na, 1.57(%).

Example 19

Synthesis of Compound I-19

[Chemical formula 106]

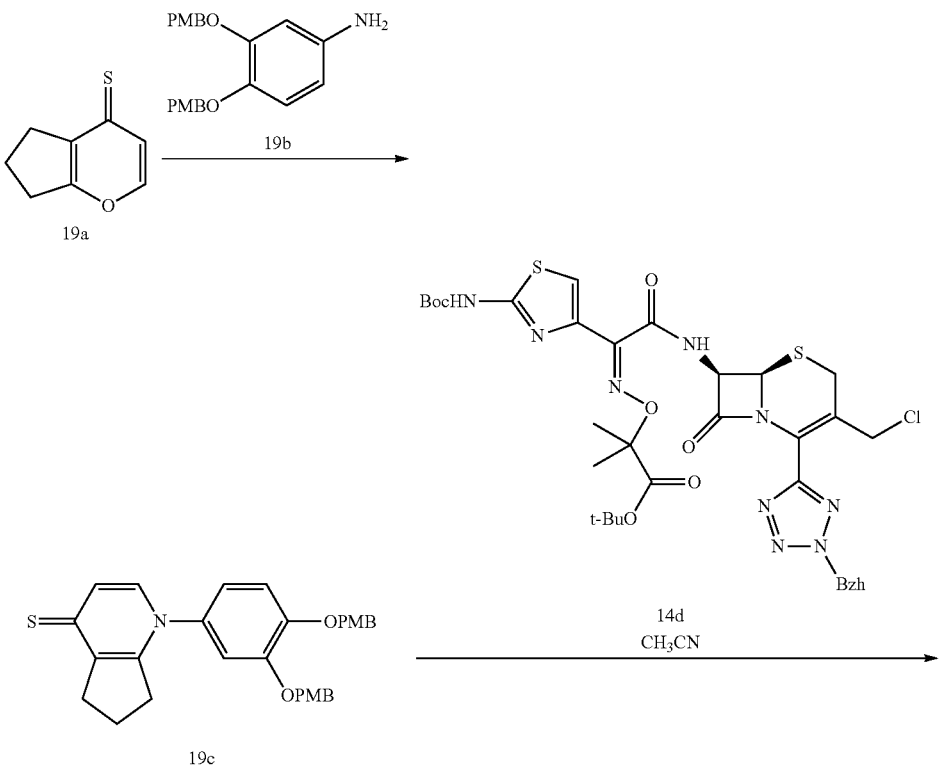

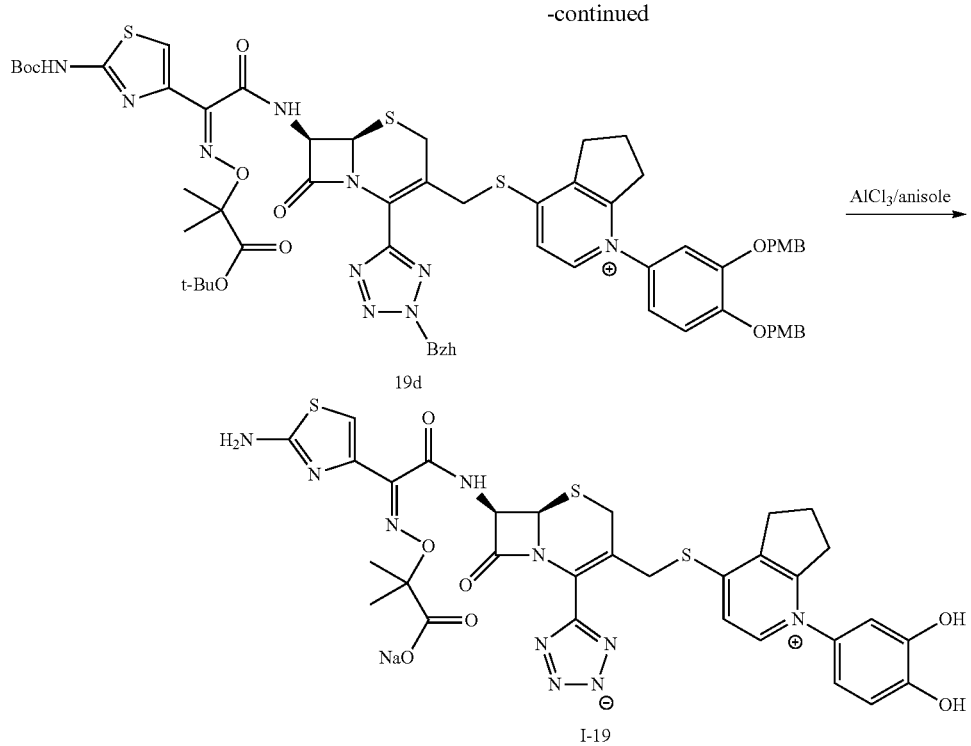

1) Compound 19a→Compound 19c

A solution of compound 19a (1.1 g, 7.23 mmol) in ethanol (5 mL) was added compound 19b (2.64 g, 7.23 mmol) and stirred at 110° C. for 16 hours with dehydration. After ethanol was removed, the concentration residue was purified by preparative liquid chromatography to give compound 19c (1.2 g, yield constant 33%).

MS: m/z=500.45 [M+H]

$^1$H-NMR (CDCl$_3$) δ: 1.99 (2H, t, J=7.8 Hz), 2.53 (2H, t, J=7.8 Hz), 3.05 (2H, t, J=7.8 Hz), 3.81 (3H, s), 3.83 (3H, s), 5.11 (2H, s), 5.13 (2H, s), 6.72 (1H, d, J=2.6 Hz), 6.74 (1H, d, J=2.6 Hz), 6.77 (1H, d, J=2.4 Hz), 6.86-6.94 (4H, m), 6.98 (1H, d, J=8.4 Hz), 7.07 (1H, d, J=7.0 Hz), 7.30 (2H, d, J=8.8 Hz), 7.34-7.39 (2H, m).

2) Compound 19c→Compound 19d

A solution of compound 19c (0.88 g, 0.90 mmol) in acetonitrile (10 mL) was added compound 14d (1.5 g, 1.76 mmol) and stirred at room temperature for 18 hours. Acetonitrile was removed under reduced pressure, and the solvent was dried under reduced pressure. Compound 19d was used in the subsequent reaction without any further purification.

3) Compound 19d→Compound I-19

The obtained compound 19d (1.10 g, 0.90 mmol equivalent) was dissolved in dichloromethane (15 ml) and cooled to −15° C., and added anisole (1.48 ml, 13.5 mmol) and 2 mol/l aluminum chloride/nitromethane solution (6.75 ml, 13.5 mmol) sequentially, and stirred at 0° C. for one hour. The reaction solution was dissolved in water, 2 mol/l hydrochloride in water and acetonitrile, and then washed with diisopropyl ether. The aqueous phase was added HP20-SS resin and acetonitrile was removed under reduced pressure. The obtained mixed liquid was subjected to HP20-SS column chromatography and eluted with water/acetonitrile. The obtained solution was concentrated under reduced pressure, and then lyophilized to give compound I-19 (220.0 mg, 24%) as white powder.

MS: m/z=751.28 [M+H]

$^1$H-NMR (DMSO-D6) δ: 1.37 (3H, s), 1.46 (3H, s), 2.15 (2H, t, J=7.3 Hz), 2.96 (4H, t, J=7.3 Hz), 3.54 (1H, d, J=16.8 Hz), 3.67 (1H, d, J=16.8 Hz), 4.44-4.57 (1H, m), 4.67-4.82 (1H, m), 5.30 (1H, d, J=4.9 Hz), 5.75 (1H, dd, J=7.5, 4.9 Hz), 6.72 (1H, s), 6.88 (2H, s), 7.09 (1H, s), 7.22 (2H, s), 8.39 (1H, d, J=6.9 Hz), 9.43-9.48 (1H, m).

Elemental analysis: C31H29ClN10O7S3Na(H2O)4.7

Calculated: C, 43.42; H, 4.51; N, 16.33; S, 11.22; Na, 2.68(%).

Found: C, 43.53; H, 4.62; N, 16.45; S, 11.14; Na, 1.81(%).

Test Example 1

The compound (I) of the present invention was evaluated for in vitro antimicrobial activity thereof.

(Method)

Measurement of Minimum Inhibitory Concentration (MIC: μg/mL) was conducted according to CLSI (Clinical and Laboratory Standards Institute) method, and the amount of bacteria for inoculation was 5×10$^5$ cfu/mL, and cation-adjusted Mueller Hinton broth containing human apo-transferrin was used as a test medium, and the experiment was conducted using broth microdilution method. The bacteria used are listed below.

TABLE 1

| No. | Species | Strain Name | Enzyme Produced | Strain Type |
|---|---|---|---|---|
| 1 | P. aeruginosa | SR24 | None | Ceftazidime resistance strain |
| 2 | P. aeruginosa | SR27060 | IMP-1 | MBL producing strain (carbapenem resistance strain) |
| 3 | P. aeruginosa | SR24837 | PER-1 | ESBL producing strain |
| 4 | A. baumannii | SR27323 | OXA-23, OXA-58 | OXA-type carbapenemase producing strain (carbapenem |

TABLE 1-continued

| No. | Species | Strain Name | Enzyme Produced | Strain Type |
|---|---|---|---|---|
| 5 | K. pneumoniae | ATCCBAA-1705 | KPC-2 | resistance strain) KPC-type carbapenemase producing strain (carbapenem resistance strain) |
| 6 | E. coli | ATCCBAA-199 | SHV-3 | ESBL producing strain |
| 7 | E. coli | ATCCBAA-200 | SHV-4 | ESBL producing strain |

Comparative Compound 1 (Compound 23a disclosed in Bioorganic & Medicinal Chemistry, vol. 4, 1996, pp. 2135-2149) of the following formula was used as a comparative compound.

[Formula 107]

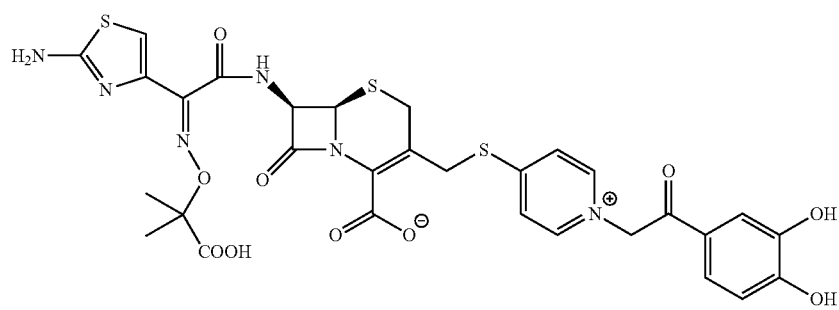

(Results)

The test results are shown in Tables 2 and 3. The values of inhibitory activity are expressed in microgram/mL (μg/ml).

TABLE 2

| Compound | P. aeruginosa SR24 | A. baumannii SR27060 | K. pneumoniae ATCC BAA-1705 | E. coli ATCC BAA-199 | E. coli ATCC BAA-200 |
|---|---|---|---|---|---|
| | | SR27323 | | | |
| Comparative Compound 1 | 0.25 | >32 | 0.5 | 0.25 | 1 | 2 |
| Compound I-1 | 0.25 | 1. | 1 | ≤0.031 | ≤0.031 | ≤0.031 |
| Compound I-2 | 0.063 | 0.5 | ≤0.031 | ≤0.031 | ≤0.031 | ≤0.031 |
| Compound I-4 | 0.125 | 2. | 1 | ≤0.031 | 0.125 | 0.25 |
| Compound I-5 | 0.125 | 1. | 0.5 | ≤0.031 | ≤0.031 | 0.063 |
| Compound I-6 | 0.063 | 0.5 | 0.125 | ≤0.031 | ≤0.031 | ≤0.031 |
| Compound I-7 | 0.5 | 4. | 2 | ≤0.031 | ≤0.031 | ≤0.031 |
| Compound I-8 | 0.25 | 16. | 2 | ≤0.031 | 0.063 | 0.25 |

TABLE 3

| Compound | P. aeruginosa SR24 | SR27060 | K. pneumoniae ATCC BAA-1705 | E. coli ATCC BAA-199 | E. coli ATCC BAA-200 |
|---|---|---|---|---|---|
| Compound I-10 | 0.25 | 2 | ≤0.031 | 0.063 | 0.125 |
| Compound I-19 | 0.125 | 4. | ≤0.031 | 0.125 | 0.125 |

Test Example 2

The compound (I) of the present invention was evaluated for in vitro antimicrobial activity thereof.

(Method)

Measurement of Minimum Inhibitory Concentration (MIC: μg/mL) was conducted according to CLSI (Clinical and Laboratory Standards Institute) method, and the amount of bacteria for inoculation was $5 \times 10^5$ cfu/mL, and cation-adjusted iso-sensitest broth containing human apo transferrin was used as a test medium, and the experiment was conducted using broth microdilution method. The bacteria used are listed below.

TABLE 4

| No. | Species | Strain Name | Enzyme Produced | Strain Type |
|---|---|---|---|---|
| 1 | E. coli | ATCCBAA-196 | TEM-10 | ESBL producing strain |
| 2 | E. coli | ATCCBAA-200 | SHV-4 | ESBL producing strain |
| 3 | E. cloacae | NCTC13464 | CTX-M group 9 | ESBL producing strain |
| 4 | K. pnuemoniae | ATCC700603 | SHV18 | ESBL producing strain |

(Result)

The test results are shown in Table 5. The values of inhibitory activity are expressed in microgram/mL (μg/ml).

TABLE 5

| Compound | E. coli ATCC BAA-196 | E. coli ATCC BAA-200 | E. cloacae NCTC 13464 | K. pneumoniae ATCC 700603 |
|---|---|---|---|---|
| Compound I-11 | ≤0.031 | ≤0.031 | ≤0.031 | ≤0.031 |
| Compound I-12 | ≤0.031 | ≤0.031 | ≤0.031 | ≤0.031 |
| Compound I-13 | 0.063 | 0.063 | 0.125 | ≤0.031 |
| Compound I-14 | 0.063 | 0.063 | 0.125 | ≤0.031 |
| Compound I-15 | ≤0.031 | ≤0.031 | 0.125 | ≤0.031 |
| Compound I-16 | ≤0.031 | ≤0.031 | ≤0.031 | ≤0.031 |
| Compound I-17 | 0.125 | 0.125 | 0.063 | 0.063 |
| Compound I-18 | 0.063 | 0.063 | 0.25 | ≤0.031 |

As shown in the above results, the compounds (I) of the present invention have been shown to have a wide antimicrobial spectrum, in particular, potent antimicrobial spectrum against Gram negative bacteria, and/or effectiveness against multidrug-resistant bacteria, and further to exhibit high stability against beta-lactamase producing Gram negative bacteria.

Formulation Example 1

Powder of a compound of the present invention is formulated to prepare an injecting agent.

INDUSTRIAL APPLICABILITY

The compounds of the present invention have a wide antimicrobial spectrum against Gram negative bacteria and Gram positive bacteria, and are effective as an antimicrobial drug having high stability against beta-lactamase producing Gram negative bacteria. Moreover, the present compounds have good disposition, and high water solubility, and thus particularly effective as an injecting agent.

The invention claimed is:
1. A compound of the formula:

[Formula 1]

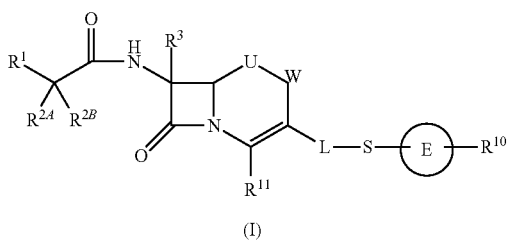

(I)

or an amino-protected compound when the amino group is present on the ring in the 7-side chain, or a pharmaceutically acceptable salt thereof, wherein W is —CH$_2$;

U is —S—, —S(=O)— or —O—;

L is a single bond, an optionally substituted lower alkylene group, an optionally substituted lower alkenylene group or an optionally substituted alkynylene group;

R$^1$ is an optionally substituted carbocyclic group or an optionally substituted heterocyclic group;

with regard to R$^{2A}$ and R$^{2B}$,

R$^{2A}$ and R$^{2B}$ are taken together to form an optionally substituted methylidene group or an optionally substituted hydroxyimino group;

R$^3$ is a hydrogen atom, —OCH$_3$ or —NH—CH(=O);

R$^{11}$ is

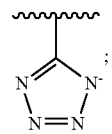

ring E is an optionally substituted pyridinium ring or an optionally substituted fused ring containing pyridinium ring;

R$^{10}$ is a group represented by the formula:

[Formula 3]

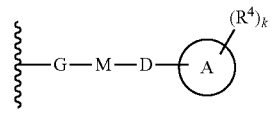

wherein ring A is a benzene ring, or a 6-membered aromatic heterocyclic group having 1-3 nitrogen atoms;

k is an integer from 2 to 5;

each R$^4$ is independently a hydrogen atom, halogen, hydroxyl group, —CN, —C(=O)—R$^5$, —C(=O)—OH, —C(=O)—OR$^5$, or —OR$^5$;

R$^5$ is a lower alkyl group or halo(lower)alkyl group; and

G is a single bond, an optionally substituted lower alkylene group, an optionally substituted alkenylene group or an optionally substituted alkynylene group;

M is a single bond or a 5- or 6-membered heterocyclic group containing at least 1 nitrogen atom;

D is a single bond, —CO—, —O—CO—, —CO—O—, —NR$^6$—, —NR$^6$—CO—, —CO—NR$^6$—, —NR$^6$—CO—NR$^6$—, —O—, —S—, —SO—, —SO$_2$—NR$^6$—, —NR$^6$—SO$_2$—, —CH$_2$—NR$^6$—CO— or —SO$_2$—;

each R$^6$ is independently a hydrogen atom or an optionally substituted lower alkyl group;

with the proviso that at least two R$^4$ are hydroxyl groups which bind respectively to adjacent carbon atoms on ring A.

2. The compound or an amino-protected compound when the amino group is present on the ring in the 7-side chain, or a pharmaceutically acceptable salt thereof according to claim 1, wherein G is a single bond, —CH$_2$—, —CH$_2$—CH$_2$—, —CH$_2$—CH$_2$—CH$_2$—, —CH=CH—, —CH=CH—CH$_2$—, —CH$_2$—CH=CH—, —CH$_2$—CH(CH$_3$)—, —CH$_2$—CH($^i$Pr)- or —CH$_2$—CH(Ph)- wherein $^i$Pr is isopropyl group and Ph is phenyl group.

3. The compound or an amino-protected compound when the amino group is present on the ring in the 7-side chain, or a pharmaceutically acceptable salt thereof according to claim 1, wherein M is a single bond or a group represented by the formula:

[Formula 5]

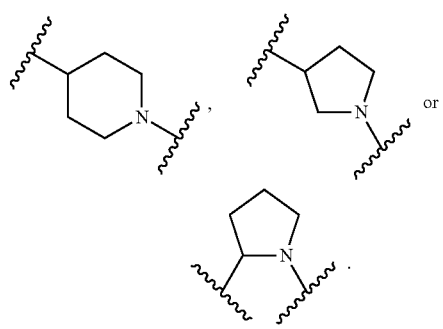

wherein the bond of the left side is attached to G and the bond of the right side is attached to D.

4. The compound or an amino-protected compound when the amino group is present on the ring in the 7-side chain, or a pharmaceutically acceptable salt thereof according to claim 1, wherein D is a single bond, —CO—, —O—CO—, —CO—O—, —NR$^6$—, —NR$^6$—CO—NR$^6$—, —NR$^6$—CO— or —CO—NR$^6$— wherein R$^6$ is as defined in claim 1.

5. The compound or an amino-protected compound when the amino group is present on the ring in the 7-side chain, or a pharmaceutically acceptable salt thereof according to claim 1, wherein the formula:

[Formula 6]

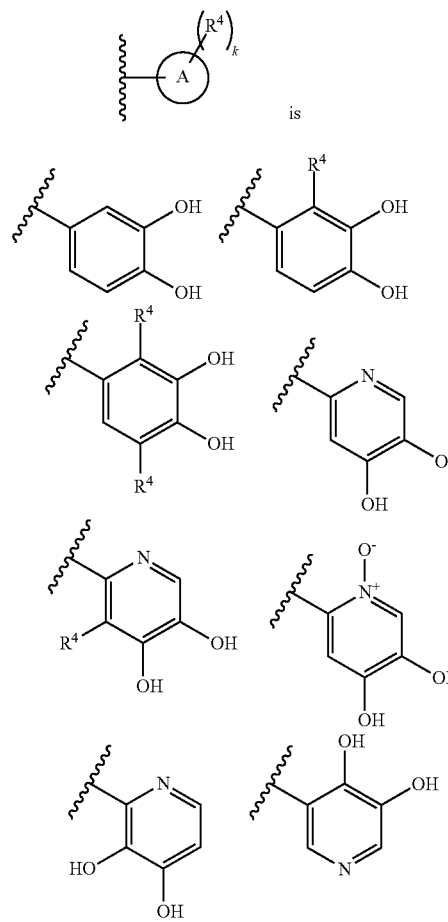

is

[Formula 7]

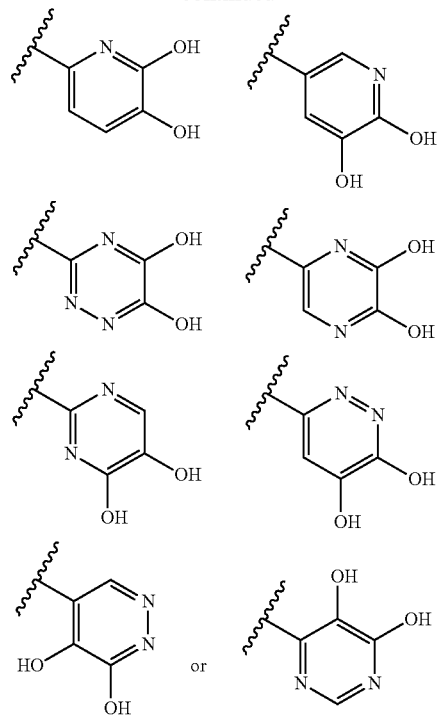

wherein each R$^4$ is independently hydrogen, halogen, hydroxyl group, —CN, —C(=O)—R$^5$, —C(=O)—OH, —C(=I)—OR$^5$ or —OR$^5$; and R$^5$ is as defined in claim 1.

6. The compound or an amino-protected compound when the amino group is present on the ring in the 7-side chain, or a pharmaceutically acceptable salt thereof according to claim 5, wherein the formula:

[Formula 8]

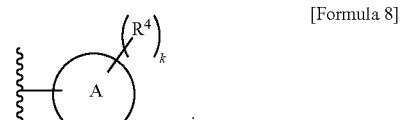

is

[Formula 9]

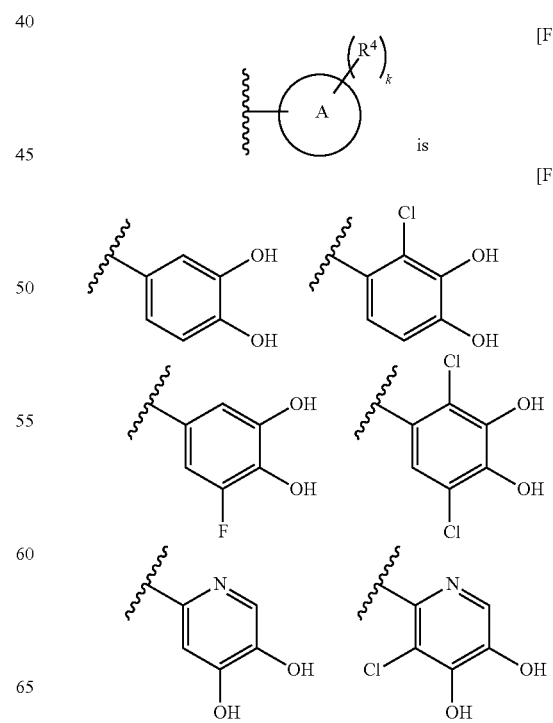

-continued

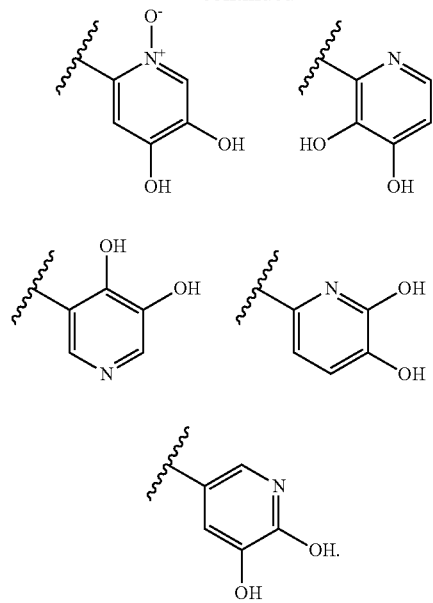

7. The compound or an amino-protected compound when the amino group is present on the ring in the 7-side chain, or a pharmaceutically acceptable salt thereof according to claim 5, wherein the formula:

[Formula 10]

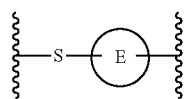 is

[Formula 11]

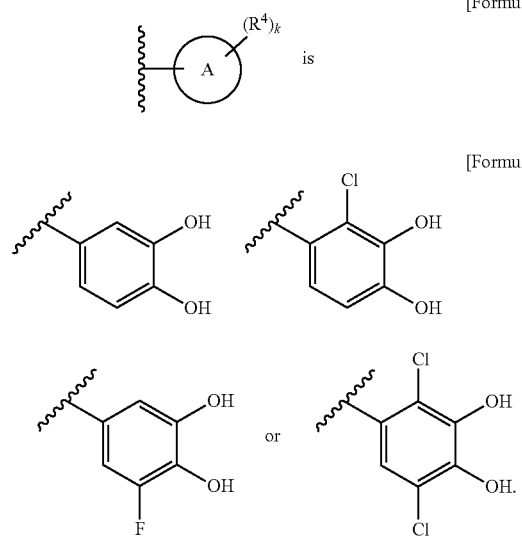

8. The compound or an amino-protected compound when the amino group is present on the ring in the 7-side chain, or a pharmaceutically acceptable salt thereof according to claim 1, wherein the formula:

[Formula 12]

is selected from

[Formula 13]

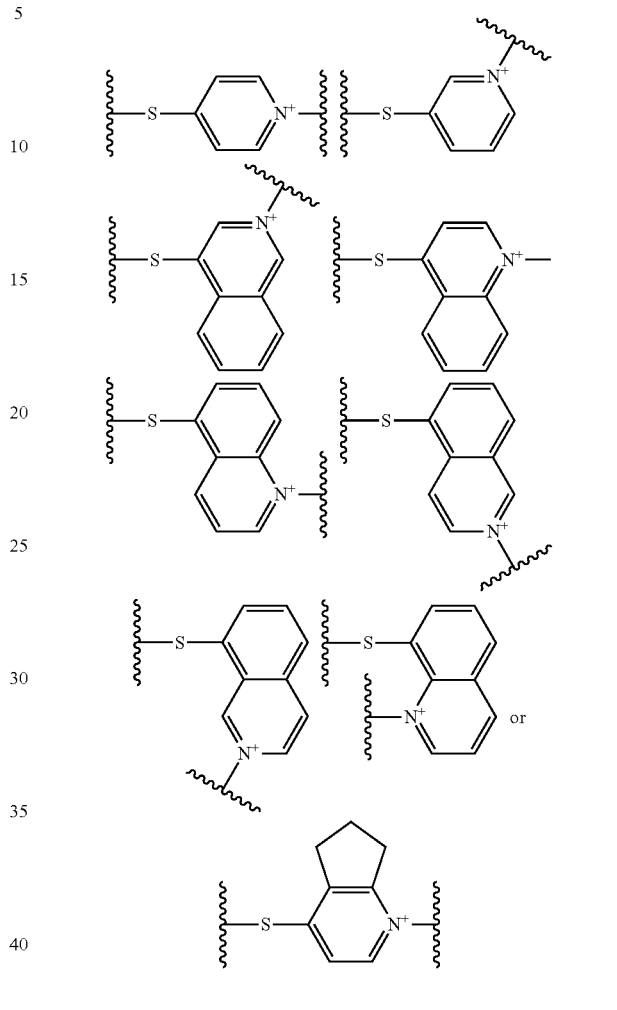

wherein the ring is optionally substituted.

9. The compound or an amino-protected compound when the amino group is present on the ring in the 7-side chain, or a pharmaceutically acceptable salt thereof according to claim 8, wherein the formula:

[Formula 14]

is selected from

[Formula 15]

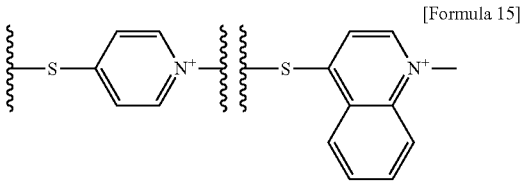

-continued

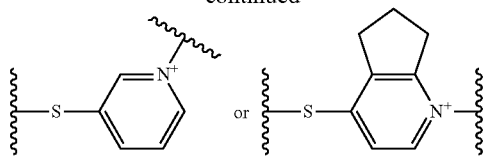

wherein the ring is optionally substituted.

10. The compound or an amino-protected compound when the amino group is present on the ring in the 7-side chain, or a pharmaceutically acceptable salt thereof according to claim 8, wherein the formula:

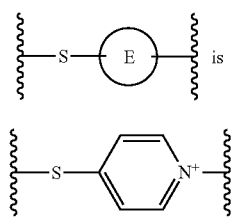

wherein the ring is optionally substituted.

11. The compound or an amino-protected compound when the amino group is present on the ring in the 7-side chain, or a pharmaceutically acceptable salt thereof according to claim 1, wherein U is —S—.

12. The compound or an amino-protected compound when the amino group is present on the ring in the 7-side chain, or a pharmaceutically acceptable salt thereof according to claim 1, wherein $R^3$ is a hydrogen atom or —OCH$_3$.

13. The compound or an amino-protected compound when the amino group is present on the ring in the 7-side chain, or a pharmaceutically acceptable salt thereof according to claim 1, wherein $R^1$ is an optionally substituted phenyl.

14. The compound or an amino-protected compound when the amino group is present on the ring in the 7-side chain, or a pharmaceutically acceptable salt thereof according to claim 1, wherein $R^1$ is represented by the formula:

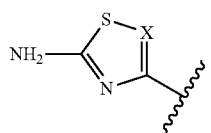

wherein X is N, C(—H) or C(—Cl).

15. The compound or an amino-protected compound when the amino group is present on the ring in the 7-side chain, or a pharmaceutically acceptable salt thereof according to claim 14, wherein X is N.

16. The compound or an amino-protected compound when the amino group is present on the ring in the 7-side chain, or a pharmaceutically acceptable salt thereof according to claim 14, wherein X is C(—H) or C(—Cl).

17. The compound or an amino-protected compound when the amino group is present on the ring in the 7-side chain, or a pharmaceutically acceptable salt thereof according to claim 1, wherein with regard to $R^{2A}$ and $R^{2B}$, b) $R^{2A}$ and $R^{2B}$ are taken together to form a substituted methylidene group shown below:

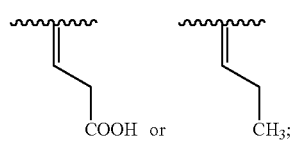

or
a substituted hydroxyimino group shown below:

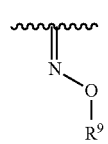

wherein $R^9$ is an optionally substituted lower alkyl group.

18. The compound or an amino-protected compound when the amino group is present on the ring in the 7-side chain, or a pharmaceutically acceptable salt thereof according to claim 1, wherein with regard to $R^{2A}$ and $R^{2B}$, b) $R^{2A}$ and $R^{2B}$ are taken together to form a substituted hydroxyimino group shown below:

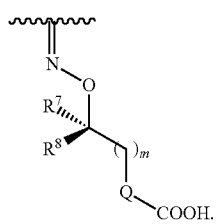

wherein $R^7$ and $R^8$ are each independently a hydrogen atom, halogen, hydroxyl group, carboxyl group, an optionally substituted lower alkyl group, an optionally substituted carbocyclic group, or an optionally substituted heterocyclic group, or $R^7$ and $R^8$ may be taken together with a neighboring atom to form an optionally substituted carbocyclic group or an optionally substituted heterocyclic group;
Q is a single bond, an optionally substituted carbocyclic group or an optionally substituted heterocyclic group; and
m is an integer from 0 to 3.

19. The compound or an amino-protected compound when the amino group is present on the ring in the 7-side chain, or a pharmaceutically acceptable salt thereof according to claim 1, wherein L is a single bond, —CH$_2$—, —CH=CH— or —CH—CH—CH$_2$—.

20. The compound or an amino-protected compound when the amino group is present on the ring in the 7-side chain, or a pharmaceutically acceptable salt thereof according to claim 1, wherein L is a single bond or —CH$_2$—.

21. A pharmaceutical composition, which comprises a compound or an amino-protected compound when the amino group is present on the ring in the 7-side chain, or a pharmaceutically acceptable salt thereof according to claim 1.

* * * * *